(12) United States Patent
Ott

(10) Patent No.: US 10,583,106 B2
(45) Date of Patent: Mar. 10, 2020

(54) METHOD OF TREATING CANCER BY ORAL ADMINISTRATION OF ACETATE COMPOSITION COMPRISING MAGNESIUM ACETATE, CALCIUM ACETATE OR ETHYLACETATE

(71) Applicant: David Michael Ott, Berkeley, CA (US)

(72) Inventor: David Michael Ott, Berkeley, CA (US)

( * ) Notice: Subject to any disclaimer, the term of this patent is extended or adjusted under 35 U.S.C. 154(b) by 0 days.

(21) Appl. No.: 15/950,877

(22) Filed: Apr. 11, 2018

(65) Prior Publication Data

US 2018/0228756 A1    Aug. 16, 2018

Related U.S. Application Data

(62) Division of application No. 15/251,880, filed on Aug. 30, 2016, now Pat. No. 9,968,580.

(60) Provisional application No. 62/283,462, filed on Sep. 2, 2015.

(51) Int. Cl.
| | |
|---|---|
| A61K 31/32 | (2006.01) |
| A23L 33/10 | (2016.01) |
| A61K 31/19 | (2006.01) |
| A61K 31/22 | (2006.01) |
| A61K 9/48 | (2006.01) |

(52) U.S. Cl.
CPC .............. *A61K 31/22* (2013.01); *A23L 33/10* (2016.08); *A61K 31/19* (2013.01); *A23V 2002/00* (2013.01); *A61K 9/4858* (2013.01)

(58) Field of Classification Search
CPC ..... A23L 33/10; A23V 2002/00; A61K 31/19; A61K 31/22; A61K 9/4858
See application file for complete search history.

(56) References Cited

U.S. PATENT DOCUMENTS 8,609,724 B2    12/2013   Michelakis et al.

OTHER PUBLICATIONS

Poirier et al (Cancer Research 43, 4575-4581, Oct. 1983).*
Poirier et al. (Cancer research 44, 1520-1522, Apr. 1984.*
Schafer et al. Drug Discovery Today 2008, 13 (21/22), 913-916.*
Horig et al. Journal of Translational Medicine 2004, 2(44).*
Hait, N. et al.., "Active, phosphorylated fingolimod inhibits histone deacetylases and facilitates fear extinction memory," Nat. Neuroscience, Jul. 2014, pp. 971-980, vol. 17, No. 7, with Online Methods, 3 pgs., Nature America, Inc.
Hamilton, A. et al., "A species of Small Antisense RNA in Post-transcriptional Gene Silencing in Plants," Sci., Oct. 28, 1999, pp. 950-952, vol. 286, No. 5441.

(Continued)

*Primary Examiner* — Savitha M Rao

(57) ABSTRACT

Genetic and epigenetic diseases and disorders are treated with FDA approved dietary compositions in the form of dietary supplements and nutraceuticals. The diseases and disorders to be treated include Rett syndrome, trinucleotide repeat diseases such as Fragile X syndrome, memory impairment, chronic inflammation, pre-cancerous conditions which involve cancer stem cells, and post-cancerous conditions which involve cancer stem cells which have survived in spite of cancer treatment. Treatment options include prophylactic treatment which is initiated prior to the development of the symptoms of the disease or disorder.

25 Claims, 16 Drawing Sheets
(4 of 16 Drawing Sheet(s) Filed in Color)

(56) References Cited

OTHER PUBLICATIONS

Han, J. et al., "Promoter-associated RNA is required for RNA-directed transcriptional gene silencing in human cells." PNAS, Jul. 24, 2007, pp. 12422-12427, vol. 104, No. 30.

Hanberry, B. et al., "High-dose vitamin B1 reduces proliferation in cancer cell lines analogous to dichloroacetate." Can. Chemother. Pharmacol., 2014, pp. 585-594, vol. 73, No. 3, Springer.

Haugrud, A. et al., "Dichloroacetate enhances apoptotic cell death via oxidative damage and attenuates lactate production in metformin-treated breast cancer cells," Breast Can. Res. Treat., 2014, pp. 539-550, vol. 147, No. 3, Springer.

Hinnebusch, B. et al., "The Effects of Short-Chain Fatty Acids on Human Colon Cancer Cell Phenotype Are Associated with Histone Hyperacetylation," J. Nutr., 2002, pp. 1012-1017, vol. 132, No. 5, American Society for Nutritional Sciences.

Ho, N. et al., "Pyruvate dehydrogenase kinase expression and metabolic changes following dichloroacetate exposure in anoxic human colorectal cancer cells," Exp. Cell Res., 2015, pp. 73-81, vol. 331, No. 1, Elsevier Inc.

Hollstein, M. et al., "p53 Mutations in Human Cancers," Sci Jul. 5, 1991, pp. 49-53, vol. 253, No. 5015.

Hong, S-E. et al., "Inhibition of S6K1 enhances dichloroacetate-induced cell death," J. Cancer Res. Clin. Oncol., 2015, pp. 1171-1179, vol. 141, No. 7, Springer.

Inden, M.et al., "Effect of Selective Serotonin Reuptake Inhibitors via 5-HT1A Receptors on L-DOPA-Induced Rotational Behavior in a Hemiparkinsonian Rat Model," J. Pharmacol. Sci., 2012, pp. 10-19, vol. 119, No. 1, The Japanese Pharmacological Society.

Johnson, R. et al., "7, 8-dihydroxyflavone exhibits therapeutic efficacy in a mouse model of Rett syndrome," J. Appl. Physiol., 2012, pp. 704-710, vol. 112, The American Physiological Society.

Juan, L-J. et al., "Histone Deacetylases Specifically Down-regulate p53-dependent Gene Activation," J. Biol. Chem., Jul. 7, 2000, pp. 20436-20443, vol. 275, No. 27, The American Society for Biochemistry and Molecular Biology, Inc.

Kailavasan, M. et al., "NMR-based evaluation of the metabolic profile and response to dichloroacetate of human prostate cancer cells," NMR in Biomed., 2014, pp. 610-616, vol. 27, No. 5, John Wiley & Sons, Ltd.

Kaufmann, W. et al., "Histone modifications in Rett syndrome lymphocytes: a preliminary evaluation," Brain Develop., 2005, pp. 331-339, vol. 27, No. 5, Elsevier B.V.

Khwaja, O. et al., "Safety, pharmacokinetics, and preliminary assessment of efficacy of mecasermin (recombinant human IGF-1) for the treatment of Rett syndrome," PNAS, Mar. 25, 2014, pp. 4596-4601, vol. 111, No. 12.

Kline, D. et al., "Exogenous Brain-Derived Neurotrophic Factor Rescues Synaptic Dysfunction in Mecp2-Null Mice," J. Veurosci., Apr. 14, 2010, pp. 5303-5310, vol. 30, No. 15.

Kolaja, K. et al., "Dose dependence of phenobarbital promotion of preneoplastic hepatic lesions in F344 rats and B6C3F1 mice: effects on DNA synthesis and apoptosis," Carcinogenesis, 1996, pp. 947-954, vol. 17, No. 5, Oxford University Press.

Kondo, T. et al., "Vinegar Intake Reduces Body Weight, Body Fat Mass, and Serum Triglyceride Levels in Obese Japanese Subjects," Biosci. Biotechnol. Biochem., 2009, pp. 1837-1843, vol. 73, No. 8.

Kotti, T. et al., "Brain cholesterol turnover required for geranylgeraniol production and learning in mice," PNAS, Mar. 7, 2006, pp. 3869-3874, vol. 103, No. 10.

Krajnc, N. "Severe Respiratory Dysrhythmia in Rett Syndrome Treated with Topiramate," J. Child Neurol., 2014, pp. NP118-NP121, vol. 29, No. 10.

Kron, M. et al., "Brain Activity Mapping in Mecp2 Mutant Mice Reveals Functional Deficits in Forebrain Circuits, Including Key Nodes in the Default Mode Network, that are Reversed with Ketamine Treatment." J. Neurosci., Oct. 3, 2012, pp. 13860-13872, vol. 32, No. 40.

Kumar, A. et al., "Novel molecular mechanisms of antitumor action of dichloroacetate against T cell lymphoma: Implication of altered glucose metabolism, pH homeostasis and cell survival regulation," Chemico-Biological Interactions, 2012, pp. 29-37, vol. 199, No. 1, Elsevier Ireland Ltd.

Kumar, A. et al., "Antitumor and chemosensitizing action of dichloroacetate implicates modulation of tumor microenvironment: A role of reorganized glucose metabolism, cell survival regulation and macrophage differentiation," Toxicol. Appl. Pharmacol., 2013, pp. 196-208, vol. 273, No. 1, Elsevier Inc.

Kunio, M. et al., "Comparison of Genomic and Epigenomic Expression in Monozygotic Twins Discordant for Rett Syndrome." PLoS One, Jun. 2013, pp. 1-9, vol. 8, No. 6, e66729.

Lin, Y-C. et aL, "Statins Increase p21 through Inhibition of Histone Deacetylase Activity and Release of Promoter-Associated HDAC1/2," Cancer Res., Apr. 1, 2008, pp. 2375-2383, vol. 68, No. 7.

Lin, G. et al., "Dichloroacetate induces autophagy in colorectal cancer cells and tumours," Br. J. Cancer, 2014, pp. 375-385, vol. 111, No. 2, Cancer Research UK.

Liston, C. et al., "Memory enhancement in early childhood," Nature, Oct. 31, 2002, p. 896, vol. 419, with Correction, Feb. 6, 2003, p. 600, vol. 421, Nature Publishing Group.

Lopez-Alt, "Chicken Bouillabaisse," Cook's Illustrated, 2009, 3 pgs., Natural Health Ltd. Partners, Brookline, MA, downloaded Jun. 17, 2017 from https://www.cooksillustrated.com/recipes/4952-chicken-bouillabaisse.

Ma, W. et al., "A pivotal role for p53: balancing aerobic respiration and glycolysis," J. Bioenerg. Biomembr., 2007, pp. 243-246, vol. 39, No. 3, Springer.

Madhok et al., "Dichloroacetate induces apoptosis and cell-cycle arrest in colorectal cancer cells." Br. J. Cancer, 2010, pp. 1746-1752, vol. 102, No. 12, Cancer Research UK.

Madiraju, P. et al., "Mitochondrial acetylcarnitine provides acetyl groups for nuclear histone acetylation," Epigenetics, Aug. 16, 2009, pp. 399-403, vol. 4, No. 6, Landes Bioscience.

Mariadason , J.et al., "Genetic Reprogramming in Pathways of Colonic Cell Maturation Induced by Short Chain Fatty Acids: Comparison with Trichostatin A, Sulindac, and Curcumin and Implications for Chemoprevention of Colon Cancer," Cancer Res., Aug. 15, 2000, pp. 4561-4572, vol. 60, No. 16, American Association for Cancer Research.

Matoba, S. et al., "p53 Regulates Mitochondrial Respiration," Sci., Jun. 16, 2006, pp. 1650-1653, vol. 312, No. 5780.

McCampbell, A. et al., "Histone deacetylase inhibitors reduce polyglutamine toxicity," PNAS, Dec. 18, 2001, pp. 15179-15184, vol. 98, No. 26.

McGowan, P. et al., "Diet and the epigenetic (re)programming of phenotypic differences in behavior," Brain Res., 2008, pp. 12-24, vol. 1237, Elsevier B.V.

Michelakis, E. et al., "Metabolic Modulation of Glioblastoma with Dichloroacetate." Sci. Translat. Med., May 12, 2010, pp. 1-8, vol. 2, No. 31, 31ra34.

Morris, K. "RNA-Directed Transcriptional Gene Silencing and Activation in Human Cells," Oligonucleotides, 2009, pp. 299-305, vol. 19, No. 4, Mary Ann Liebert, Inc.

Morris, K. "Modulation of gene-specific epigenetic states and transcription by non-coding RNAs," Clin. Epigenet., 2011, pp. 433-437, vol. 2, Springer.

Na, E. et al., "A Mouse Model for MeCP2 Duplication Syndrome: MeCP2 Overexpression Impairs Learning and Memory and Synaptic Transmission," J. Neurosci., Feb. 29, 2012, pp. 3109-3117, vol. 32, No. 9.

Na, E. et al., "The Impact of MeCP2 Loss- or Gain-of-Function on Synaptic Plasticity," Neuropsychopharmacology, 2013, pp. 212-219, vol. 38, No. 1, Nature Publishing Group.

Nashun, B. et al., "Reprogramming of cell fate: epigenetic memory and the erasure of memories past," EMBO J., 2015, pp. 1296-1308, vol. 34, No. 10.

Neul, J. et al., "Specific mutations in Methyl-CpG-Binding Protein 2 confer different severity in Rett syndrome," Neurology, 2008, pp. 1313-1321, vol. 70, No. 16, AAN Enterprises, Inc.

Ogier, M. et al., "Brain-Derived Neurotrophic Factor Expression and Respiratory Function Improve After Ampakine Treatment in a Mouse Model of Rett Syndrome," J. Neurosci., Oct. 3, 2007, pp. 10912-10917, vol. 27, No. 40, Society for Neuroscience.

(56) References Cited

OTHER PUBLICATIONS

Ookubo, M. et al., "Antidepressants and mood stabilizers effects on histone deacetylase expression in C57BL/6 mice: Brain region specific changes," J. Psychiatric Res., 2013, pp. 1204-1214, vol. 47, No. 9.

Orey, "Fat Burning Vinegar," The Healing Powers of Vinegar: A Complete Guide to Nature's Most Remarkable Remedy, 2006, 16 pgs., Kensington Books, New York, NY.

Paik, W. et al., "Nonenzymatic Acetylation of Histones with Acetyl-CoA." Biochim. Biophys. Acta, 1970, pp. 513-522, vol. 213, No. 2.

Park, M. et al., "Anaplerotic Triheptanoin Diet Enhances Mitochondrial Substrate Use to Remodel the Metabolome and Improve Lifespan, Motor Function, and Sociability in MeCP2-Null Mice," PLoS One, Oct. 2014, pp. 1-22, vol. 9, No. 10, e109527.

Peleg, S. et al., "Altered Histone Acetylation Is Associated with Age-Dependent Memory Impairment in Mice," Sci., May 7, 2010, pp. 753-756, vol. 328, No. 5979, with Erratum, Jun. 25, 2010, p. 1.

Penney, J. et al., "Histone deacetylases in memory and cognition," Sci. Signaling, Dec. 9, 2014, pp. 1-7, vol. 7, No. 355, re12.

Pruitt, K. et al., "Inhibition of SIRT1 Reactivates Silenced Cancer Genes without Loss of Promoter DNA Hypermethylation," PLoS Genetics, Mar. 2006, pp. 0344-0352, vol. 2, No. 3, e40.

Reus, G. et al., "Ketamine and imipramine in the nucleus accumbens regulate histone deacetylation induced by maternal deprivation and are critical for associated behaviors," Behavioural Brain Res., 2013, pp. 451-456, vol. 256, Elsevier B.V.

Roux, J-C. et al., "Treatment with desipramine improves breathing and survival in a mouse model for Rett syndrome," Euro. J. Neurosci., 2007, pp. 1915-1922, vol. 25, No. 7, Federation of European Neuroscience Societies and Blackwell Publishing Ltd.

Sandberg, G. et al., "Effect of in vitro promoter methylation and CGG repeat expansion on FMR-1 expression," Nuc. Acids Res., 1997, pp. 2883-2887, vol. 25, No. 14, Oxford University Press.

Sando, R. et al., "HDAC4 Governs a Transcriptional Program Essential for Synaptic Plasticity and Memory," Cell, Nov. 9, 2012, pp. 821-834, vol. 151, No. 4, with Supplemental Information, pp. S1-S13, Elsevier Inc.

Schaevitz, L. et al., "Acetyl-L-Carnitine Improves Behavior and Dendritic Morphology in a Mouse Model of Rett Syndrome," PLoS One, Dec. 2012, pp. 1-13, vol. 7, No. 12.

Shahbazian, M. et al., "Insight into Rett syndrome: MeCP2 levels display tissue- and cell-specific differences and correlate with neuronal maturation," Human Mol. Genet., 2002, pp. 1151-124, vol. 11, No. 2, Oxford University Press.

Shapira, J. et al., "Current Research on Regenerative Food Systems," Committee on Space Research (COSPAR), Eleventh Annual Meeting, Tokyo, Japan, May 9-21, 1968, pp. 1-8, Paper No. L.5.2, Working Group V, May 16, 1968, Ames Research Center, NASA, Moffett Field, CA.

Shen, H. et al., "Dual-targeting of aberrant glucose metabolism in glioblastoma," J. Exp. Clin. Cancer Res., 2015, pp. 1-11, vol. 34, No. 14, BioMed Central.

Shroads, A. et al., "Age-Dependent Kinetics and Metabolism of Dichloroacetate: Possible Relevance to Toxicity." JPET, 2008, pp. 1163-1171, vol. 324, No. 3, The American Society for Pharmacology and Experimental Therapeutics.

Signorini, C. et al., "Altered erythrocyte membrane fatty acid profile in typical Rett syndrome: Effects of omega-3 polyunsaturated fatty acid supplementation," Prostaglandins, Leukotrienes and Essential Fatty Acids, 2014, pp. 183-193, vol. 91, No. 5, Elsevier Ltd.

Soragni, E. et al., "Long intronic GAA.TTC repeats induce epigenetic changes and reporter gene silencing in a molecular model of Friedreich ataxia," Nuc. Acids Res., Sep. 2008, pp. 6056-6065, vol. 36, No. 19.

Stacpoole, P. et al., "Chronic Toxicity of Dichloroacetate: Possible Relation to Thiamine Deficiency in Rats," Fundament. Appl. Toxicol., 1990, pp. 327-337, vol. 14, No. 2, Society of Toxicology.

Sun, L. et al., "Insulin-Like Growth Factor-I Stimulates Histone H13 and H4 Acetylation in the Brain in Vivo," Endocrinol., 2006, pp. 5480-5490, vol. 147, No. 11, The Endocrine Society.

Sun, R. et al., "Reversal of the glycolytic phenotype by dichloroacetate inhibits metastatic breast cancer cell growth in vitro and in vivo," Breast Cancer Res. Treat., 2010, pp. 253-260, vol. 120, No. 1, Springer.

Suzuki, S. et al., "Brain-Derived Neurotrophic Factor Regulates Cholesterol Metabolism for Synapse Development," J. Neurosci., Jun. 13, 2007, pp. 6417-6427, vol. 27, No. 24, Society of Neuroscience.

Szczesna, K. et al., "Improvement of the Rett Syndrome Phenotype in a Mecp2 Mouse Model Upon Treatment with Levodopa and a Dopa-Decarboxylase Inhibitor," Neuropsychopharmacol., 2014, pp. 2846-2856, vol. 39, No. 12, Nature Publishing Group.

Tabolacci, E. et al., "Epigenetics, Fragile X Syndrome and Transcriptional Therapy," Am. J. Med. Genet. Part A, 2013, pp. 2797-2808, vol. 161A, No. 11, Wiley Periodicals, Inc.

Takahashi, S. et al., "Skewed X chromosome inactivation failed to explain the normal phenotype of a carrier female with MECP2 mutation resulting in Rett syndrome," Clin. Genet., 2008, pp. 257-261, vol. 73, No. 3, Blackwell Munksgaard, Singapore.

Tao, J. et al., "Phosphorylation of MeCP2 at Serine 80 regulates its chromatin association and neurological function," PNAS, Mar. 24, 2009, pp. 4882-4887, vol. 106, No. 12.

Tropea, D. et al., "Partial reversal of Rett Syndrome-like symptoms in MeCP2 mutant mice," PNAs, Feb. 10, 2009, pp. 2029-2034, vol. 106, No. 6.

Van Der Graaf, A. et al., Efficacy and safety of fluvastatin in children and adolescents with heterozygous familial hypercholesterolaemia., Acta Paediatrica, 2006, pp. 1461-1466, vol. 95, No. 11, Taylor & Francis Group.

Vater, I. et al., "The mutational pattern of primary lymphoma of the central nervous system determined by whole-exome sequencing," Leukemia, 2015, pp. 677-685, vol. 29, No. 3, Nature Publishing Group.

Vecsler, M. et al., "MeCP2 deficiency down-regulates specific nuclear proteins that could be partially recovered by valproic acid in vitro," Epigenet., Jan. 1, 2010, pp. 61-67, vol. 5, No. 1, Landes Bioscience.

Vella, S. et al., "Dichloroacetate inhibits neuroblastoma growth by specifically acting against malignant undifferentiated cells," Int. J. Cancer, 2012, pp. 1484-1493, vol. 130, No. 7, UICC.

Ventura, A. et al., "Restoration of p53 function leads to tumour regression in vivo," Nature, Feb. 8, 2007, pp. 661-665, vol. 445, No. 7128, Nature Publishing Group.

Visco, C. et al., "Comprehensive gene expression profiling and immunohistochemical studies support application of immunophenotypic algorithm for molecular subtype classification in diffuse large B-cell lymphoma: a report from the International DLBCL Rituximab-CHOP Consortium Program Study," Leukemia, 2012, pp. 2103-2113, vol. 26, No. 9, Nature Publishing Group.

Weaver, I. et al., "Epigenetic programming by maternal behavior," Nat. Neurosci., Aug. 2004, pp. 847-854, vol. 7, No. 8, Nature Publishing Group.

Weinberg, M. et al., "Long Non-Coding RNA Targeting and Transcriptional De-Repression." Nuc. Acid Ther., 2013, pp. 9-14, vol. 23, No. 1, Mary Ann Liebert, Inc.

Weinert, B. et al., "Acetyl-Phosphate Is a Critical Determinant of Lysine Acetylation in E. coli," Mol. Cell, Jul. 25, 2013, pp. 265-272, vol. 51, No. 2, Elsevier Inc.

Weng, S-M. et al., "Synaptic plasticity deficits in an experimental model of rett syndrome: long-term potentiation saturation and its pharmacological reversal," Neurosci., 2011, pp. 314-321, vol. 180, Elsevier Ltd.

Wolfe, A., "The Acetate Switch," Microbiol. Mol. Biol. Rev., Mar. 2005, pp. 12-50, vol. 69, No. 1, American Society for Microbiology.

Yamaguchi, H. et al., "p53 Acetylation Is Crucial for Its Transcription-Independent Proapoptotic Functions," J. Biol. Chem., Apr. 24, 2009, pp. 11171-11183, vol. 284, No. 17, The American Society for Biochemistry and Molecular Biology, Inc.

Zhang, J. et al., "Genetic heterogeneity of diffuse large B-cell lymphoma," PNAS, Jan. 22, 2013, pp. 1398-1403, vol. 110, No. 4.

(56) References Cited

OTHER PUBLICATIONS

Zhou, Z. et al., "Brain-Specific Phosphorylation of MeCP2 Regulates Activity-Dependent Bdnf Transcription, Dendritic Growth, and Spine Maturation," Neuron, Oct. 19, 2006, pp. 255-269, vol. 52, No. 2.
Zhou, X. et al., "Dichloroacetate restores drug sensitivity in paclitaxel-resistant cells by inducing citric acid accumulation," Mol. Cancer, 2015, pp. 1-12, vol. 14, No. 63, BioMed Central.
Hazar-Rethinam, M. et al., "RacGAP1 Is a Novel Downstream Effector of E2F7-Dependent Resistance to Doxorubicin and Is Prognostic for Overall Survival in Squamous Cell Carcinoma," Mol. Cancer Ther., 2015, pp. 1939-1950, vol. 14, No. 8, AACR.
Abildgaard, C. et al., "Bioenergetic modulation with dichloroacetate reduces the growth of melanoma cells and potentiates their response to BRAFV600E inhibition," J. Transl Med., 2014, pp. 1-12, vol. 12, No. 247, BioMed Central Ltd.
Agnoletto, C. et al., "Sodium dichloroacetate exhibits anti-leukemic activity in B-chronic lymphocytic leukemia (B-CLL) and synergizes with the p53 activator Nutlin-3," Oncotarget, 2014, pp. 4347-4360, vol. 5, No. 12.
Amir, R. et al., "Rett syndrome is caused by mutations in X-linked MECP2, encoding methyl-CpG-binding protein 2," Nat. Genet., Oct. 1999, pp. 185-188, vol. 23, No. 2, Nature America, Inc.
Bensaad, K. et al., "TIGAR, a p53-Inducible Regulator of Glycolysis and Apoptosis." Cell, Jul. 14, 2006, pp. 107-120, vol. 126, No. 1.
Ben-Zeev, B. et al., "Glatiramer acetate (GA, Copolymer-1) an hypothetical treatment option for Rett syndrome," Med. Hypotheses, 2011, pp. 190-193, vol. 76.
Biacsi, R. et al., "SIRT1 Inhibition Alleviates Gene Silencing in Fragile X Mental Retardation Syndrome," PLoS Genet., 2008, pp. 1-9, vol. 4, No. 3, e1000017.
Boffa, L. et al., "Suppression of Histone Deacetylation in Vivo and in Vitro by Sodium Butyrate," J. Biol. Chem., May 25, 1978, pp. 3364-3366, vol. 253, No. 10.
Bonnet, S. et al., "A Mitochondria-K+ Channel Axis Is Suppressed in Cancer and Its Normalization Promotes Apoptosis and Inhibits Cancer Growth," Can. Cell, Jan. 2007, pp. 37-51, vol. 11, No. 1, Elsevier Inc.
Buchovecky et al., "A suppressor screen in Mecp2 mutant mice implicates cholesterol metabolism in Rett syndrome," Nat. Genet., Sep. 2013, pp. 1013-1020, vol. 45, No. 9, with Online Methods, 2 pgs., Nature America, Inc.
Cairns, R. et al., "Metabolic targeting of hypoxia and HIF1 in solid tumors can enhance cytotoxic chemotherapy," PNAS, May 29, 2007, pp. 9445-9450, vol. 104, No. 22.
Caku, A. et al., "Effect of Lovastatin on Behavior in Children and Adults with Fragile X Syndrome: An Open-Label Study," Am. J. Med. Genet. Part A, 2014, pp. 2834-2842, vol. 164A, No. 11, Wiley Periodicals, Inc.
Cattoretti, G. et al., "Deregulated BCL6 expression recapitulates the pathogenesis of human diffuse large B cell lymphomas in mice," Can. Cell, May 2005, pp. 445-455, vol. 7, No. 5.
Cerniglia, G. et al., "The PI3K/Akt Pathway Regulates Oxygen Metabolism via Pyruvate Dehydrogenase (PDH)-E1alpha Phosphorylation," Mol. Can. Ther., Aug. 2015, pp. 1928-1938, vol. 14, No. 8, American Association for Cancer Research.
Cervoni, N. et al., "Demethylase Activity Is Directed by Histone Acetylation," J. Biol. Chem., Nov. 2, 2001, pp. 40778-40787, vol. 276, No. 44, The American Society for Biochemistry and Molecular Biology, Inc.
Chapkin, R. et al., "Mechanisms by which docosahexaenoic acid and related fatty acids reduce colon cancer risk and inflammatory disorders of the intestine," Chem. Phys. Lipids, 2008, pp. 14-23, vol. 153, No. 1.
Chen, R. et al., "Deficiency of methyl-CpG binding protein-2 in CNS neurons results in a Rett-like phenotype in mice," Nat. Genet., Mar. 2001, pp. 327-331, vol. 27, No. 3, Nature Publishing Group.
Chen, W. et al., "Derepression of BDNF Transcription Involves Calcium-Dependent Phosphorylation of MeCP2," Sci., Oct. 3, 2003, pp. 885-889, vol. 302, No. 5646.

Chow, J. et al., "Silencing of the Mammalian X Chromosome," Annu. Rev. Genomics Hum. Genet., 2005, pp. 69-92, vol. 6, with Drawing pp. C1-C3, Annual Reviews.
Clark, W., "In defense of self: how the immune system really works in managing health and disease," ISBN: 978-0-19-531126-6, 2007, pp. 1-265, Oxford University Press, USA.
Comerford, S. et al., "Acetate Dependence of Tumors," Cell, Dec. 18, 2014, pp. 1591-1602, vol. 159, No. 7.
Compagno, M. et al., "Mutations of multiple genes cause deregulation of NF-kappaB in diffuse large B-cell lymphoma," Nat., Jun. 4, 2009, pp. 717-721, vol. 459, No. 7247, Macmillan Publishers Limited.
Condorelli, F. et al., "Inhibitors of histone deacetylase (HDAC) restore the p53 pathway in neuroblastoma cells," Br. J. Pharmacol., 2008, pp. 657-668, vol. 153, No. 4.
Cousens, L. et al., "Different Accessibilities in Chromatin to Histone Acetylase," J. Biol. Chem., Mar. 10, 1979, pp. 1716-1723, vol. 254, No. 5.
Csankovszki, G. et al., "Synergism of Xist RNA, DNA Methylation, and Histone Hypoacetylation in Maintaining X Chromosome Inactivation," J. Cell Biol., May 14, 2001, pp. 773-783, vol. 153, No. 4, The Rockefeller University Press.
Davidson, L. et al., "Chemopreventive n-3 Polyunsaturated Fatty Acids Reprogram Genetic Signatures During Colon Cancer Initiation and Progression in the Rat," Can. Res., Sep. 15, 2004, pp. 6797-6804, vol. 64, No. 18.
De Felice, C. et al., "Systemic oxidative stress in classic Rett syndrome," Free Rad. Biol. Med., 2009, pp. 440-448, vol. 47, No. 4, Elsevier Inc.
De Felice, C. et al., "Partial rescue of Rett syndrome by omega-3 polyunsaturated fatty acids (PUFAs) oil," Genes Nutr., 2012, pp. 447-458, vol. 7, No. 3, Springer.
De Felice, C. et al., "Effects of omega-3 polyunsaturated fatty acids on plasma proteome in Rett syndrome," Mediat. Inflamm., 2013, pp. 1-9, vol. 2013, Article ID 723269, Hindawi Publishing Corporation.
De Felice, C. et al., "Oxidative brain damage in Mecp2-mutant murine models of Rett syndrome," Neurobiol. Dis., 2014, pp. 66-77, vol. 68, Elsevier Inc.
Delaney, L. et al., "Dichloroacetate affects proliferation but not survival of human colorectal cancer cells," Apoptosis, 2015, pp. 63-74, vol. 20, No. 1.
Deogracias, R. et al., "Fingolimod, a sphingosine-1 phosphate receptor modulator, increases BDNF levels and improves symptoms of a mouse model of Rett syndrome," PNAS, Aug. 28, 2012, pp. 14230-14235, vol. 109, No. 35.
Detich, N. et al., "Valproate Induces Replication-Independent Active DNA Demethylation," J. Biol. Chem., Jul. 25, 2003, pp. 27586-27592, vol. 278, No. 30, The American Society for Biochemistry and Molecular Biology, Inc.
Di Magno, L. et al., "Druggable glycolytic requirement for Hedgehog-dependent neuronal and medulloblastoma growth," Cell Cycle, Nov. 1, 2014, pp. 3404-3413, vol. 13, No. 21, Taylor & Francis Group, LLC.
Dinarello, C. et al., "Histone Deacetylase Inhibitors for Treating a Spectrum of Diseases Not Related to Cancer," Mol. Med., May-Jun. 2011, pp. 333-352, vol. 17, Nos. 5-6.
Dragich, J. et al., "Differential Distribution of the Mecp2 Splice Variants in the Postnatal Mouse Brain," J. Comp. Veurol., 2007, pp. 526-542, vol. 501, No. 4, Wiley-Liss, Inc.
Duan, Y. et al., "Antitumor activity of dichloroacetate on C6 glioma cell: in vitro and in vivo evaluation," OncoTarg Ther., 2013, pp. 189-198, vol. 6, Dove Press.
Dunbar, E. et al., "Phase 1 trial of dichloroacetate (DCA) in adults with recurrent malignant brain tumors" Invest. New Drugs, 2014, pp. 452-464, vol. 32, No. 3, Springer.
Ellaway, C. et al., "Rett Syndrome: Randomized Controlled Trial of L-Carnitine," J. Child Neurol., 1999, pp. 162-167, vol. 14, No. 3.
Eyal, S. et al., "The Activity of Antiepileptic Drugs as Histone Deacetylase Inhibitors," Epilepsia, 2004, pp. 737-744, vol. 45, No. 7.
Fitzsimmons, P. et al., "Kinetics and effects of dichloroacetic acid in rainbow trout," Aquat. Toxicol., 2009, pp. 186-194, vol. 94, No. 3, Elsevier B.V.

(56) References Cited

OTHER PUBLICATIONS

Fiume, M., "Final Report on the Safety Assessment of Triacetin," Internat. J. Toxicol., 2003, pp. 1-10, vol. 22, Suppl. 2.

Flavin, D. "Non-Hodgkin's Lymphoma Reversal with Dichloroacetate," J. Oncol., Jul. 2010, pp. 1-4, vol. 2010, Article ID 414726, Hindawi Publishing Corporation.

Fong, L. et al., "alpha-Difluoromethylornithine Induction of Apoptosis: A Mechanism Which Reverses Pre-established Cell Proliferation and Cancer Initiation in Eosphageal Carcinogenesis in Zinc-deficient Rats," Can. Epidem., Biomark. Prevent., Mar. 2001, pp. 191-199, vol. 10, No. 3.

Fraga, M. et al., "A Mouse Skin Multistage Carcinogenesis Model Reflects the Aberrant DNA Methylation Patterns of Human Tumors," Can. Res., Aug. 15, 2004, pp. 5527-5534, vol. 64, No. 16, American Association for Cancer Research.

Gang, B. et al., "Targeting of two aspects of metabolism in breast cancer treatment," Can. Biol. Ther., Nov. 2014, pp. 1533-1541, vol. 15, No. 11.

Gibson, J. et al., "X chromosome inactivation patterns in brain in Rett syndrome: implications for the disease phenotype," Brain Devel., 2005, pp. 266-270, vol. 27, No. 4, Elsevier B.V.

Gold, W. et al., "MeCP2 deficiency is associated with reduced levels of tubulin acetylation and can be restored using HDAC6 inhibitors," J. Mol. Med., 2015, pp. 63-72, vol. 93, No. 1, Springer.

Grillo, E. et al., "Revealing the Complexity of a Monogenic Disease: Rett Syndrome Exome Sequencing." PLoS one, Feb. 2013, pp. 1-9, vol. 8, No. 2, e56599.

Guo, W. et al., "VPA Alleviates Neurological Deficits and Restores Gene Expression in a Mouse Model of Rett Syndrome," PLoS One, Jun. 2014, pp. 1-9, vol. 9, No. 6, e100215.

Guy, J. et al., "Reversal of Neurological Defects in a Mouse Model of Rett Syndrome," Sci., Feb. 23, 2007, pp. 1143-1147, vol. 315, No. 5815.

\* cited by examiner

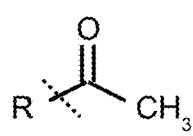
Acetyl Group
*Fig. 1A*
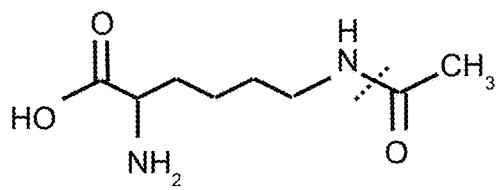
Acetylated Lysine
*Fig. 1B*
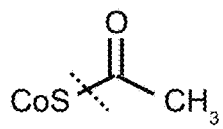
Acetyl-CoA
*Fig. 1C*
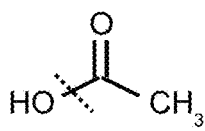
Acetic Acid (vinegar)
*Fig. 1D*
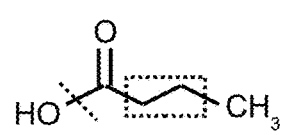
Butyrate
*Fig. 1E*
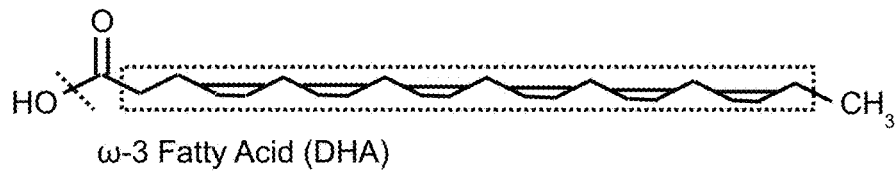
ω-3 Fatty Acid (DHA)
*Fig. 1F*
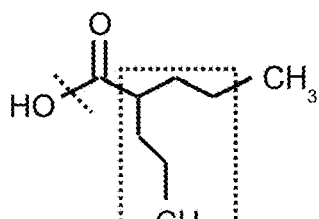
Valproic Acid
*Fig. 1G*
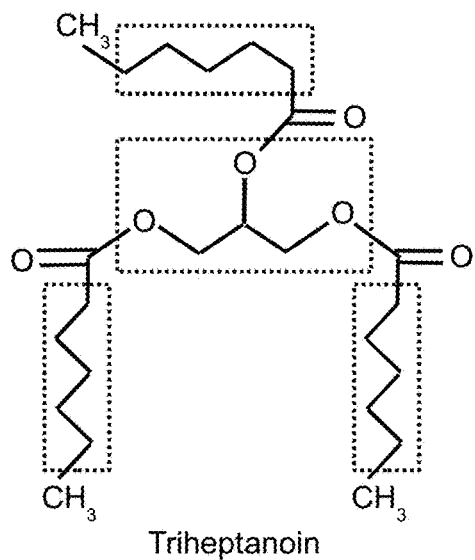
Triheptanoin
*Fig. 1H*
*Fig. 1*

The role of the SQLE enzyme in cholesterol synthesis

RTT symptoms vary with age for MeCP2 null mice

Acetylcarnitine can enter nucleus to form Acetyl-CoA

Butyrate treatment inhibits HDAC enzyme activity

HDACi activity of various short chain fatty acids

Histone acetylation due to short chain fatty acids

Tubastatin A, and HDACi, increases gene expression

Butyrate plus ω-3 is additive, but ω-6 is subtractive

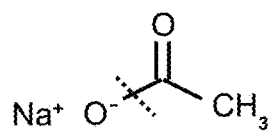
Sodium Acetate
*Fig. 10A*
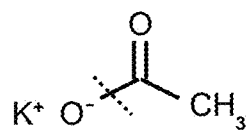
Potassium Acetate
*Fig. 10B*
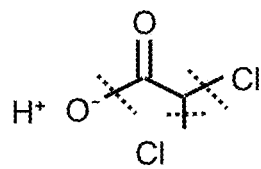
Dichloroacetate
*Fig. 10C*
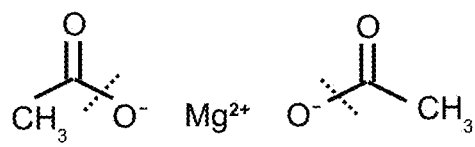
Magnesium Acetate
*Fig. 10D*
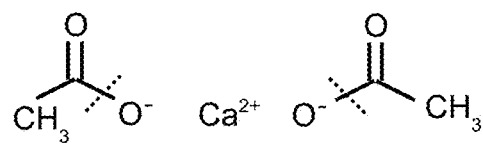
Calcium Acetate
*Fig. 10E*
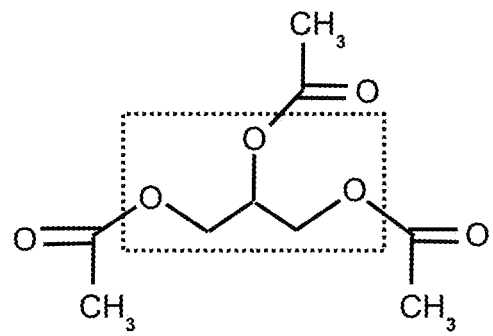
Glycerin Triacetate
*Fig. 10F*
*Fig. 10* p53-null (-/-) cells use glycolysis for ATP production

Genes affected by mutation in at least three PCNSL

Valproic acid demethylated CpG sites

Cell viability after HDACi treatments

Gene reactivation from HDACi treatment

METHOD OF TREATING CANCER BY ORAL ADMINISTRATION OF ACETATE COMPOSITION COMPRISING MAGNESIUM ACETATE, CALCIUM ACETATE OR ETHYLACETATE

CROSS REFERENCE TO RELATED APPLICATIONS

This application claims priority to U.S. Ser. No. 15/251,880, filed Aug. 30, 2016, which claims priority to U.S. provisional application No. 62/283,462, filed Sep. 2, 2015, the disclosures of which are hereby incorporated by reference in their entirety.

FIELD OF THE INVENTION

The invention relates to the therapeutic use of dietary supplements and nutraceuticals which have an epigenetic effect on gene expression. Various diseases and disorders involve inappropriate levels of gene expression which can be corrected epigenetically. Examples include Rett Syndrome, various trinucleotide repeat diseases, and cancerous and pre-cancerous cells in which tumor suppressor genes that have been epigenetically silenced. The use of dietary supplements and nutraceuticals which have an epigenetic effect can beneficially improve the gene expression profile for those who have these diseases and disorders.

BACKGROUND OF THE INVENTION

1. Definitions, Glossary, and Abbreviations

Administration of a compound: Causing a compound to enter into the body of an animal, either orally, by injection, or by any other means.

Chromatin: An organized structure of the DNA (and its attached RNA and proteins) of a single chromosome that controls the compactness and accessibility of the DNA.

CpG dinucleotide (CpG): A pair of nucleotides within a strand of DNA consisting of a cytosine followed by a guanine in the forward reading direction of the DNA strand. Due to C:G and G:C base paring, each CpG dinucleotide on one strand will be base paired with a (reverse reading) CpG island on the other "antisense" strand of double stranded DNA (which is read in the reverse direction from the "sense" strand that codes for proteins).

CpG island: A region of DNA where the density of CpG dinucleotides is high. A typical CpG island could be 1000 nucleotides long, with a CpG dinucleotide every 10 nucleotides (on average). A CpG dinucleotide is considered to be methylated if most (e.g. 80%) of its CpGs are methylated, or demethylated if few (e.g. 20%) of its CpGs are methylated.

CpG methylation: A CpG where the cytosine is methylated (forming 5-methyl cytosine).

Dietary supplement [FDA definition]: A dietary supplement is a product taken by mouth that contains a "dietary ingredient" intended to supplement the diet. The "dietary ingredients" in these products may include vitamins, minerals, herbs or other botanicals, amino acids, and substances such as enzymes, organ tissues, glandulars, and metabolites. Dietary supplements can also be extracts or concentrates, and may be found in many forms such as tablets, capsules, softgels, gelcaps, liquids, or powders. They can also be in other forms such as a bar, but if they are, information on their label must not represent the product as a conventional food or a sole item of a meal or diet.

DNA Methyltransferase (DNMT): An enzyme that binds to DNA and can methylate a CpG site. DNMT1 is considered to be the key maintenance methyltransferase in mammals (e.g. keeping CpG islands methylated that were already methylated). DNMT3 enzymes can methylate CpG sites that were not already methylated (de novo methylation). In practice they are both involved in establishing and maintaining the methylation state of CpG sites (e.g. in the absence of DNMT1 or DMNT3, demethylation can occur).

Ectopic: In an abnormal place or position. For example, if a specific CpG island on a particular type of cell's DNA is not normally significantly methylated, a cell of that type in which that CpG island is significantly methylated would be said to have an ectopically methylated CpG island.

Ectopic acetylation: Acetylation in a place or position that would not normally be acetylated.

Ectopic deacetylation: Deacetylation in a place or position that would normally be acetylated.

Ectopic methylation: Methylation in a place or position that would not normally be methylated.

Ectopic demethylation: Demethylation in a place or position that would normally be methylated.

Epigenetics: The study of cellular and physiological phenotypic trait variations that are caused by heritable DNA modifications that switch genes on and off and affect how cells read genes, instead of being caused by changes in the DNA sequence itself. Epigenetics literally means "above" or "on top of" genetics. Epigenetic DNA modifications typically involve attachments to the DNA, for example a methyl group attached to a cytosine nucleotide, or a nucleosome that has the DNA wound upon it.

Epigenetic marker: A general term for the state of a site associated with gene expression that can have more than one state, resulting in more or less gene expression as a result of the state of the marker. For example, a lysine on a specific histone affecting the expression of a gene on a chromosome in a cell may have the alternatives of acetylation, methylation, or no modification at all. These are three alternatives states for that epigenetic marker.

Epigenetic pattern: The pattern of epigenetic markers that results in a pattern of gene expression for that cell. Each type of cell will have a set of epigenetic patterns that are appropriate for that type of cell.

FCC Grade: The Food Chemicals Codex (FCC) is a compendium of standards used internationally for the quality and purity of food ingredients like preservatives, flavorings, colorings and nutrients. FCC grade ingredients are approved for use in foods, dietary supplements, and cosmetics.

Food additive: A compound that is listed in the "Everything Added to Foods in the United States (EAFUS)" FDA database.

Fortify (food): To increase the nutritive value of food, especially with micronutrients.

Histone acetylation (HAc): The attachment of an acetyl group to a lysine located on the amino-terminal tail of a histone. The shorthand code "H3K9Ac" indicates that Lysine (K) 9 of histone 3 is acetylated.

Histone acetyl transferase (HAT): An enzyme that acetylates histones, typically at their amino-tail lysine residues. The acetyl group donor for HAT enzymes is Acetyl-CoA.

Histone Deacetylase Inhibitor (HDACi): A compound that inhibits the activity of a histone deacetylase enzyme, thereby increasing the acetylation of histones. Histone deacetylase activity is sometimes inferred from the observation of increased histone acetylation, which does not necessarily distinguish between true HDACi activity, the enhancement of histone acetyl transferase activity or even the non-enzymatic acetylation of histones. Some HDACis are known to both inhibit histone deacetylases and enhance histone acetyl transferase activity, thereby increasing net histone acetylation by both mechanisms.

Histone methylation (HMe): The attachment of a methyl group to a lysine located on the amino-terminal tail of a histone. The shorthand code "H3K27Me" indicates that Lysine (K) 27 of histone 3 is methylated.

Metabolism: The entire set of chemical reactions that can occur within a living organism. This includes anabolism (the formation of more complex molecules from simple ones), catabolism (the breakdown of complex molecules from complex molecules to make simpler ones) and also simpler reactions, such as thiol-disulfide exchange reactions.

Metastable: Stable provided that it is subjected to no more than small disturbances, and capable of being so long-lived as to be stable for practical purposes.

Micronutrient: A chemical element or substance that is required by a living organism in minute amounts for normal growth.

Mitigate: To make less severe or less intense.

Non-coding RNA (ncRNA): Any RNA molecule that is produced by DNA transcription but does not code for a protein. ncRNAs have a variety of functions, resulting in a variety of function-specific names such as siRNA, microRNA (miRNA), long, non-coding RNA (lncRNA), etc.

Nucleosome: A structure formed from 8 histone proteins (2 each of H2A, H2B, H3, and H4 histones) on top of which DNA can be wound in order to provide chromatin compaction and thereby control the accessibility of genes for transcription.

Nutraceutical: A food containing health-giving food additives and having medicinal benefit.

Nutrigenomics: The scientific study of the interaction of nutrition and genes, especially with regard to the prevention or treatment of disease.

Prodrug: An inert compound that becomes active for its purpose only after it is transformed or metabolized by the body.

Prophylactic treatment: Preventative treatment in order to avoid the development of a disease or condition.

Therapeutic Window: The dosage range from the minimum beneficial dosage to the maximum tolerable dosage.

Treatment: The willful administration of a therapeutic agent with the intent of preventing or mitigating a disease or disorder.

2. References

Abildgaard, C. et al. Bioenergetic modulation with dichloroacetate reduces the growth of melanoma cells and potentiates their response to BRAFV600E inhibition. Journal of Translational Medicine 12:247 (2014).

Agnoletto, C. et al. Sodium dichloroacetate exhibits anti-leukemic activity in B-chronic lymphocytic leukemia (B-CLL) and synergizes with the p53 activator Nutlin-3. Oncotarget 5:4347 (2014).

Amir, R. E. et al. Rett syndrome is caused by mutations in X-linked MECP2, encoding methyl-CpG-binding protein 2. Nature Genetics 23:127 (1999).

Baicsi, R. et al. SIRT1 inhibition alleviates gene silencing in Fragile X mental retardation syndrome. PLoS Genetics 4:e1000017 (2008).

Bensaad, K. et al. TIGAR, a p53-inducible regulator of glycolysis and apoptosis. Cell 126:107 (2006).

Boffa, L. C. et al. Suppression of histone deacetylation in vivo and in vitro by sodium butyrate. The Journal of Biological Chemistry 253:3364 (1978).

Bonnet, S. et al. A mitochondria-K+ channel axis is suppressed in cancer and its normalization promotes apoptosis and inhibits cancer growth. Cancer Cell 11:37 (2007)

Buchovecky, C. M. et al. A suppressor screen in Mecp2 mutant mice implicates cholesterol metabolism in Rett syndrome. Nature Genetics 45:1013 (2013).

Cairns, R. et al. Metabolic targeting of hypoxia and HIF1 in solid tumors can enhance cytotoxic chemotherapy. Proceedings of the National Academy of Science 104:9445 (2007).

Caku, A. et al. Effect of lovastatin on behavior in children and adults with fragile X syndrome: an open-label study. American Journal of Medical Genetics 164A:2834 (20140.

Cattoretti, G. et al. Deregulated BCL6 expression recapitulates the pathogenesis of human diffuse large B cell lymphomas in mice. Cancer Cell 7:445 (2005).

Cernigla, G. J. et al. The PI3K/Akt Pathway Regulates Oxygen Metabolism via Pyruvate Dehydrogenase (PDH)-E1α Phosphorylation. Molecular Cancer Therapeutics 14:1928 (2015).

Cervoni, N. et al. Demethylase activity is directed by histone acetylation. The Journal of Biological Chemistry 276:40778 (2001).

Chapkin, R. S. et al. Mechanisms by which docosahexaenoic acid and related fatty acids reduce colon cancer risk and inflammatory disorders of the intestine. Chemistry and Physics of Lipids 153:14 (2008).

Chen, R. Z. et al. Deficiency of methyl-CpG binding protein-2 in CNS neurons results in a Rett-like phenotype in mice. Nature Genetics 27:327 (2001).

Chen, W. G. et al. Derepression of BDNF transcription involves calcium-dependent phosphorylation of MeCP2. Science 302:885 (2003).

Chow, J. C. et al. Silencing of the mammalian X chromosome. Annual Review of Genomics and Human Genetics 6:69 (2005).

Chow, J. C. et al. Promoter-associated RNA is required for RNA-directed transcriptional gene silencing in human cells. Proceedings of the National Academy of Science 104:10104 (2007).

CIREP (Cosmetic Ingredient Review Expert Panel); Final Report on the Safety Assessment of Triacetin. International Journal of Toxicity 22(Suppl. 2):1 (2003).

Clark, W. R. In Defense of Self: How the Immune System Really Works. Oxford University Press, Oxford, 2008.

Comerford, S. A. et al. Acetate dependence of tumors. Cell 159:1591 (2014).

Compagno, M. et al. Mutations of multiple genes cause deregulation of NF-kappaB in diffuse large B-cell lymphoma. Nature 459:717 (2009).

Cousens, L. S. et al. Different accessibilities in chromatin to histone acetylase. The Journal of Biological Chemistry 254:1716 (19790.

Csankovszki, G. et al. Synergism of Xist RNA, DNA methylation, and histone hypoacetylation in maintaining X chromosome inactivation. The Journal of Cell Biology 153:773 (2001).

Davidson, L. A. et al. Chemopreventive n-3 polyunsaturated fatty acids reprogram genetic signatures during colon cancer initiation and progression in the rat. Cancer Research 64:6797 (2004).

De Felice, C. et al. Systemic oxidative stress in classic Rett syndrome. Free Radical Biology & Medicine 47:440 (2009).

De Felice, C. et al. Partial rescue of Rett syndrome by ω-3 polyunsaturated fatty acids (PUFAs) oil. Genes & Nutrition 7:447 (2012).

De Felice, C. et al. Effects of ω-3 polyunsaturated fatty acids on plasma proteome in Rett syndrome. Mediators of Inflammation f2013:723269 (2013).

De Felice, C. et al. Oxidative brain damage in Mecp2-mutant murine models of Rett syndrome. Neurobiology of Disease 68:66 (2014).

De Mango, L. et al. Druggable glycolytic requirement for Hedgehog-dependent neuronal and medulloblastoma growth. Cell Cycle 13:3404 (2014).

Delaney, L. M. et al. Dichloroacetate affects proliferation but not survival of human colorectal cancer cells. Apoptosis 20:63 (2015).

Detich, N. et al. Valproate induces replication-independent active DNA demethylation. The Journal of Biological Chemistry 278:27586 (2003).

Deogracias, R. et al. Fingolimod, a sphingosine-1 phosphate receptor modulator, increases BDNF levels and improves symptoms of a mouse model of Rett syndrome. Proceedings of the National Academy of Science 109:14230 (2012).

Dinarello, C. A. et al. Histone deacetylase inhibitors for treating a spectrum of diseases not related to cancer. Molecular Medicine 17:333 (2011).

Duan, Y. et al. Antitumor activity of dichloroacetate on C6 glioma cell: in vitro and in vivo evaluation. OncoTargets and Therapy 6:189 (2013).

Dunbar, E. M. et al. Phase 1 trial of dichloroacetate (DCA) in adults with recurrent malignant brain tumors. Investigative New Drugs 32:452 (2014).

Fitzsimmons, P. N. et al. Kinetics and effects of dichloroacetic acid in rainbow trout. Aquatic Toxicology 94:186 (2009).

Flavin, D. F. Non-Hodgkin's Lymphoma Reversal with Dichloroacetate. Journal of Oncology, Volume 2010, Article ID 414726.

Fong, L. Y. et al. Alpha-difluoromethylornithine induction of apoptosis: a mechanism which reverses pre-established cell proliferation and cancer initiation in esophageal carcinogenesis in zinc-deficient rats. Cancer Epidemiology, Biomarkers & Prevention 10:191 (2001).

Fraga, M. F. et al. A mouse skin multistage carcinogenesis model reflects the aberrant DNA methylation patterns of human tumors. Cancer Research 64:5527 (2004).

Gang, B. P. et al. Targeting of two aspects of metabolism in breast cancer treatment. Cancer Biology and Therapy 15:1533 (2014).

Gibson, J. H. et al. X chromosome inactivation patterns in brain in Rett syndrome: implications for the disease phenotype. Brain & Development 27:266 (2005).

Gold, W. A. et al. MeCP2 deficiency is associated with reduced levels of tubulin acetylation and can be restored using HDAC6 inhibitors. Journal of Molecular Medicine 93:63 (2015).

Grillo, E. et al. Revealing the complexity of a monogenic disease: Rett syndrome exome sequencing. PLoS ONE 8:e56599 (2013).

Guy, J. et al. Reversal of neurological defects in a mouse model of Rett syndrome. Science 315:1143 (2007).

Hamilton, A. et al. A species of small antisense RNA in posttranscriptional silencing in plant genes. Science 286:950 (1999).

Hanberry, B. S. et al. High-dose vitamin B1 reduces proliferation in cancer cell lines analogous to dichloroacetate. Cancer Chemotherapy and Pharmacology 73:585 (2014).

Haugrid, A. B. et al. Dichloroacetate enhances apoptotic cell death via oxidative damage and attenuates lactate production in metformin-treated breast cancer cells. Breast Cancer Research and Treatment 147:539 (2014).

Hinnebusch, B. F. et al. The effects of short-chain fatty acids on human colon cancer cell phenotype are associated with histone hyperacetylation. Journal of Nutrition 132:1012 (2002).

Ho, N. et al. Pyruvate dehydrogenase kinase expression and metabolic changes following dichloroacetate exposure in anoxic human colorectal cancer cells. Experimental Cell Research 331:73 (2015).

Hollstein, M. et al. p53 mutations in human cancers. Science 252:49 (1991).

Hong, S. et al. Inhibition of S6K1 enhances dichloroacetate-induced cell death. Journal of Cancer Research and Clinical Oncology 141:1171 (2015).

Juan, L. et al. Histone deacetylases specifically down-regulate p53-dependent gene activation. The Journal of Biological Chemistry 275:20436 (2000).

Kailavasan, M. et al. NMR-based evaluation of the metabolic profile and response to dichloroacetate of human prostate cancer cells. NMR Biomedicine 27:610 (2013).

Kenji Lopez-Alt, J. Introducing Chicken Bouillabaisse; in Cooks Illustrated, November-December 2009.

Kline, D. D. et al. Exogenous brain-derived neurotrophic factor rescues synaptic dysfunction in Mecp2-null mice. The Journal of Neuroscience 30:5303 (2010).

Kolaja, K. L. et al. Dose dependence of phenobarbital promotion of preneoplastic hepatic lesions in F344 rats and B6C3F1 mice: effects on DNA synthesis and apoptosis. Carcinogenesis 17:947 (1996).

Kondo, T. et al. Vinegar intake reduces body weight, body fat mass, and serum triglyceride levels in obese Japanese subjects. Bioscience, Biotechnology and Biochemistry 73:1837 (2009).

Kotti, T. J. et al. Brain cholesterol turnover required for geranylgeraniol production and learning in mice. Proceedings of the National Academy of Science 103:3869 (2006).

Krajnc, N. et al. Severe respiratory dysrhythmia in Rett syndrome treated with topiramate. Journal of Child Neurology 29:NP118 (2013).

Kron, M. et al. Brain activity mapping in Mecp2 mutant mice reveals functional deficits in forebrain circuits, including key nodes in the default mode network, that are reversed with ketamine treatment. The Journal of Neuroscience 32:13860 (2012).

Kumar, A. et al. Novel molecular mechanisms of antitumor action of dichloroacetate against T cell lymphoma: Implication of altered glucose metabolism, pH homeostasis and cell survival regulation. Chemico-Biological Interactions 199:29 (2012).

Kumar, A. et al. Antitumor and chemosensitizing action of dichloroacetate implicates modulation of tumor microenvironment: a role of reorganized glucose metabolism, cell survival regulation and macrophage differentiation. Toxicology and Applied Pharmacology 273:196 (2013).

Kunio, M. et al. Comparison of Genomic and Epigenomic Expression in Monozygotic Twins Discordant for Rett Syndrome. PLoS ONE 8:e66729 (2013).

Lin, G. et al. Dichloroacetate induces autophagy in colorectal cancer cells and tumors. British Journal of Cancer 15:111 (2014).

Lin, Y. C. et al. Statins increase p21 through inhibition of histone deacetylase activity and release of promoter-associated HDAC1/2. Cancer Research 68:2375 (2008).

Liston, C. et al. Memory enhancement in early childhood. Nature 419:896 (2002).

Ma, W. et al. A pivotal role for p53: balancing aerobic respiration and glycolysis. Journal of Bioenergetics and Biomembranes 39:243 (2007).

Madhok, B. M. et al. Dichloroacetate induces apoptosis and cell-cycle arrest in colorectal cancer cells. British Journal of Cancer 102:1746 (2010).

Madiraju, P. et al. Mitochondrial acetylcarnitine provides acetyl groups for nuclear histone acetylation. Epigenetics 4:399 (2009).

Matoba, S. et al. p53 regulates mitochondrial respiration. Science 313:1650 (2006).

McCampbell, A. et al. Histone deacetylase inhibitors reduce polyglutamine toxicity. Proceedings of the National Academy of Science 98:15179 (201).

Mariadson, J. M. et al. Genetic reprogramming in pathways of colonic cell maturation induced by short chain fatty acids: comparison with trichostatin A, sulindac, and curcumin and implications for chemoprevention of colon cancer. Cancer Research 60:4561 (2000).

Michelakis, E. et al. Metabolic modulation of glioblastoma with dichloroacetate. Science Translational Medicine 2:31ra34 (2010).

Michelakis, E. Method of Treating Cancer using Dichloroacetate. U.S. Pat. No. 8,609,724 (2013).

McGowan, P. O. et al. Diet and the epigenetic (re)programming of phenotypic differences in behavior. Brain Research 1237:12 (2008).

Morris, K. V. RNA-directed transcriptional gene silencing and activation in human cells, Oligonucleotides 19:299 (2009).

Morris, K. V. Modulation of gene-specific epigenetic states and transcription by non-coding RNAs. Clinical Epigenetics 2:433 (2011).

Na, E. S. et al. A mouse model for MeCP2 duplication syndrome: MeCP2 overexpression impairs learning and memory and synaptic transmission. The Journal of Neuroscience 32:3109 (2012).

Na, E. S. et al. The Impact of MeCP2 Loss- or Gain-of-Function on Synaptic Plasticity. Neuropsychopharmacology Reviews 38:212 (2013).

Nashun, B. et al. Reprogramming of cell fate: epigenetic memory and the erasure of memories past. The EMBO Journal 34:1296 (2015).

Neul, J. L. et al. Specific mutations in methyl-CpG-binding protein 2 confer different severity in Rett syndrome. Neurology 70:1313 (2008).

Ookubo, M. et al. Antidepressants and mood stabilizers effects on histone deacetylase expression in C57BL/6 mice: Brain region specific changes. Journal of Psychiatric Research 47:1204 (2013).

Ohinata, T. S. et al. Skewed X chromosome inactivation failed to explain the normal phenotype of a carrier female with MECP2 mutation resulting in Rett syndrome. Clinical Genetics 73:257 (2008).

Orey, C. Fat Burning Vinegar, in The Healing Powers of Vinegar, Kensington Books, New York, 2006.

Paik, W. K. et al. Nonenzymatic acetylation of histones with acetyl-CoA. Biochimica et Biophysica Acta 213:513 (1970).

Park, M. J. et al. Anaplerotic triheptanoin diet enhances mitochondrial substrate use to remodel the metabolome and improve lifespan, motor function, and sociability in MeCP2-null mice. PLoS One 9:e109527 (2014).

Peleg, S. et al. Altered histone acetylation is associated with age-dependent memory impairment in mice. Science 328:753 (2010).

Pruitt, K. et el. Inhibition of SIRT1 reactivates silenced cancer genes without loss of promoter DNA hypermethylation. PLoS Genetics 2:e40 (2006).

Reus, G. Z. et al. Ketamine and imipramine in the nucleus accumbens regulate histone deacetylation induced by maternal deprivation and are critical for associated behaviors. Behavioral Brain Research 256:451 (2013).

Sandberg, G. et al. Effect of in vitro promoter methylation and CGG repeat expansion on FMR-1 expression. Nucleic Acids Research 25:2883 (1997).

Schaevitz, L. R. et al. Acetyl-L-carnitine improves behavior and dendritic morphology in a mouse model of Rett syndrome. PLoS One 7:e51586 (2012).

Shanbazian, M. D. et al. Insight into Rett syndrome: MeCP2 levels display tissue- and cell-specific differences and correlate with neuronal maturation. Human Molecular Genetics 11:115 (2002).

Shen, H. et al. Dual-targeting of aberrant glucose metabolism in glioblastoma. Journal of Experimental & Clinical Cancer Research 34:14 (2015).

Shroads, A. L. et al. Age-dependent kinetics and metabolism of dichloroacetate: possible relevance to toxicity. The Journal of Pharmacology and Experimental Therapeutics 324:1163 (2008).

Signorini, C. et al. Altered erythrocyte membrane fatty acid profile in typical Rett syndrome: effects of omega-3 polyunsaturated fatty acid supplementation. Prostaglandins, leukotrienes, and essential fatty acids 91:183 (2014).

Soragni, E. et al. Long intronic GAA*TTC repeats induce epigenetic changes and reporter gene silencing in a molecular model of Friedreich ataxia. Nucleic Acids Research 36:6056 (2008).

Stacpoole, P. W. et al. Chronic Toxicity of Dichloroacetate: Possible Relation to Thiamine Deficiency in Rats. Fundamental and Applied Toxicology 14:327 (1990).

Sun, L. Y. et al. Insulin-like growth factor-I stimulates histone H3 and H4 acetylation in the brain in vivo. Endochronology 147:5480 (2006).

Sun, R. C. et al. Reversal of the glycolytic phenotype by dichloroacetate inhibits metastatic breast cancer cell growth in vitro and in vivo. Breast Cancer Research and Treatment 120:253 (2009).

Suzuki, S. et al. Brain-derived neurotrophic factor regulates cholesterol metabolism for synapse development. The Journal of Neuroscience 27: 6417 (2007).

Szczesna, K. et al. Improvement of the Rett syndrome phenotype in a MeCP2 mouse model upon treatment with levodopa and a dopa-decarboxylase inhibitor. Neuropsychopharmacology 39:2846 (2014).

Tao, J. et al. Phosphorylation of MeCP2 at Serine 80 regulates its chromatin association and neurological function. Proceedings of the National Academy of Sciences 106:4882 (2009).

Tropea D. et al. Partial reversal of Rett Syndrome-like symptoms in MeCP2 mutant mice. Proceedings of the National Academy of Science 106:2029 (2009).

van der Graff, A. et al. Efficacy and safety of fluvastatin in children and adolescents with heterozygous familial hypercholesterolaemia. Acta Paediatrica 95:1461 (2006).

Ventura, A. et al, Restoration of p53 function leads to tumour regression in vivo. Nature 445:661 (2007).

Vater, I. et al. The mutational pattern of primary lymphoma of the central nervous system determined by whole-exome sequencing. Lerkemia 29:677 (2015).

Visco, C, et al. Comprehensive gene expression profiling and immunohistochemical studies support application of immunophenotypic algorithm for molecular subtype classification in diffuse large B-cell lymphoma: a report from the International DLBCL Rituximab-CHOP Consortium Program Study. Leukemia 26:2103 (2012).

Weaver, I. C. et al. Epigenetic programming by maternal behavior. Nature Neuroscience 7:847 (2004).

Weinberg, M. S. et al. Long non-coding RNA targeting and transcriptional de-repression. Nucleic Acid Therapeutics 1:9 (2013).

Weng, S. M. et al. Synaptic plasticity deficits in an experimental model of Rett syndrome: long-term potentiation saturation and its pharmacological reversal. Neuroscience 180:314 (2011).

Wolfe, A. J. The acetate switch. Microbiology and Molecular Biology Reviews 69:12 (20050.

Vecsler, M. et al. MeCP2 deficiency downregulates specific nuclear proteins that could be partially recovered by valproic acid in vitro. Epigenetics 5:61 (2010).

Vella, S. et al. Dichloroacetate inhibits neuroblastoma growth by specifically acting against malignant undifferentiated cells. International Journal of Cancer 130: 1484 (2012).

Yamaguchi, H. et al. p53 acetylation is crucial for its transcription-independent proapoptotic functions. The Journal of Biological Chemistry 284:11171 (2009).

Zhang, J. et al. Genetic heterogeneity of diffuse large B-cell lymphoma. Proceedings of the National Academy of Science 110:1398 (2013).

Zhaolan, Z. et al. Brain-specific phosphorylation of MeCP2 regulates activity-dependent Bdnf transcription, dendritic growth, and spine maturation. Neuron 52:255 (2006).

Zhou, X. et al. Dichloroacetate restores drug sensitivity in paclitaxel-resistant cells by inducing citric acid accumulation. Molecular Cancer 14:63 (2015).

3. Description of the Published Art 3.1 New Knowledge about Genetic Diseases

Modern methods greatly increase the amount of physiological detail which can be measured or observed, in some cases causing revisions to long-held beliefs. This is especially true now that genetic information is available for the entire coding regions of the human genome.

Diseases associated with gross genetic defects have been known for decades, but only a small minority of the population inherit any specific genetic defect which, in and of itself, produces a disease. Most genetic diseases are now believed to be associated with a combination of genetic alleles or mutations (none of which individually cause the disease), or the combination of one or more genetic factors with environmental factors (either environmental exposure or "lifestyle" choices).

Although appropriate lifestyle choices have long been recognized as being key to achieving and maintaining wellness (e.g. cessation of smoking, avoiding drug or alcohol abuse, adequate exercise, a proper diet, . . . ), for individuals these are frequently easier said than done.

Even though there is general agreement as to the importance of a proper diet, there are still disagreements about what a proper diet consists of. Major ongoing controversies regarding the benefits or risks of dietary choices include carbohydrates vs. fats, vegetarianism, veganism, vitamin supplements, added sugars, high fructose corn syrup, organic food, pesticides, non-GMO, etc.

Lost in the noise is the importance of micronutrients.

The emerging field of nutragenomics focuses on the interaction of nutrition and genes, especially with regard to the prevention or treatment of disease. The relationship goes both ways. Proper gene expression depends upon proper nutrition. But proper nutrition for an individual depends in part upon that individual's genome.

Twin studies provide a means for determining the interplay between genes and the environment in the development of specific diseases. Monozygotic (identical) twins share almost 100% of their genes, which means that many of their characteristics will be nearly the same, and any major differences are likely to be due to differences in environmental exposure or experience. But dizygotic (fraternal) twins share only about 50% of their genes.

The classical twin study design compares the degree of twin similarity for some characteristic, both for a set of monozygotic twins and a set of dizygotic twins. If the monozygotic twins are considerably more similar than the dizygotic twins (as is the case for most traits), this is strong evidence that genes play an important role for that trait. And if monozygotic twins show a strong divergence for a particular trait, this is evidence that the environment plays an important role for that trait.

3.2 Rett Syndrome, a Well-Studied Genetic Disease

Although Rett syndrome (RTT) is a rare disease (occurring in approximately 1 in 10,000 live female births), it is a devastating disease which typically produces severe mental and physical retardation. The affected girls typically have no verbal skills and about 50% of affected individuals cannot walk.

Infant development is normal until about 6 to 18 months of age, including the learning of basic skills such as purposeful hand use, development of gross motor skills such as crawling or walking, and early language development. After the onset of disease, learning progress essentially stops and these skills are progressively lost. Repetitive stereotyped hand movements, such as wringing and/or repeatedly putting hands into the mouth, also develop.

In 90% of the cases, the cause of Rett syndrome is mutation of the MeCP gene on the X chromosome, which codes for the MeCP2 (Methyl CpG binding Protein 2) protein. Approximately 95% of the time the mutation is de novo (e.g. a sporadic mutation from the father that originated during spermatogenesis), although about 5% of the time it is inherited from the mother.

There are strong motivations for trying to develop therapies for Rett syndrome:

1. The cause is well known.
2. The disease has been extensively researched.
3. There are multiple mouse models that replicate the disease.
4. There are a variety of treatments that have been tested (mostly using either mouse models in vivo or mouse cells in vitro) and have shown some beneficial results.

5. There is evidence (from the mouse models) that the disease may be reversible, even years after it developed.
6. The patients with Rett syndrome require almost continuous care (they can't feed themselves, they shouldn't be left in one position for too long, they cannot dress themselves, etc.), and their parents are desperate for an effective treatment to be developed.

3.2.1 the MeCP2 Gene is X-Linked

Although females have two copies of the MeCP2 gene (one on each X chromosome), males only have one copy. Females with RTT almost always have one defective copy of MeCP2 (mutated) and one good copy (wild type), but the disease causing allele is dominant. Because males only have one copy, if it is mutated the disease is more severe than in females, and for human males it is almost always lethal by the age of two years.

Due to X-inactivation, only one of the female's X chromosomes is fully active, resulting in females having nearly the same level of X chromosome gene products as males (known as "gene dosage"). Early in the development of the female fetus, each of its cells randomly inactivates either the maternal or the paternal X chromosome by epigenetically silencing (approximately ¾) of its genes (by hypermethylating the CpG islands in the promoter regions of each of these genes). Roughly half of these cells will have inactivated the maternal X chromosome, and the others will have inactivated the paternal X chromosome, although due to randomness the split may be somewhat skewed (e.g. 60/40). Because epigenetic programming is inherited when cells divide, all of the daughter cells derived from each of these cells will inactivate that same chromosome.

Because the fetus had multiple cells by the time x-inactivation occurs, different tissue samples from an individual can have different skews.

Because monozygotic twins can have different X-inactivation patterns (and skews), resulting in a different proportion of cells expressing defective MeCP2, the results of a study of two monozygotic twins with discordant Rett syndrome [Kunio, 2013] are interesting. Monozygotic (identical) twins have been widely used in genetic studies to determine the relative contributions of heredity and the environment in human diseases. In this case, although they have the same heredity, their X chromosome inactivation pattern is also part of their "nature", and therefore it was of interest to see if they had significantly different X-inactivation skews (otherwise, their difference in disease severity would be attributed to environmental effects).

From Kunio, 2013:

"Twin 1 (RS1), who has a milder phenotype, developed normally until 2.5 years of age; she was able to use a spoon, to run and jump, and to climb stairs. At age 2, she communicated using two-word sentences. At 2.5 years she started to lose learned words and the ability to communicate. . . . At 3 years and 5 months, she lost purposeful hand skills and started to exhibit stereotypical hand movements. . . . At age 12 years, she had generalized convulsions and her EEG showed epileptic discharges. Since then, an antiepileptic drug has been administered and her seizures are well controlled. At age 13 years, she could run and jump, was rather hyperactive and slimmer than twin 2, was able to reach for and grasp objects, liked to swim and to watch children's TV programs."

"Twin 2 (RS2), who has a more severe phenotype, . . . Her development during the first 6 months appeared normal but she soon started to lag. She was able to hold her head steady at 6 months, could roll over at 9 months, and could sit by herself at 9 months. She had marked hypertonia and never walked. At age 12 months, she spoke using simple words, such as "momma" and "dada", and could grasp a toy, but she lost these abilities later and started to exhibit stereotypical hand movements. . . . At 2 years and one month, she had afebrile seizures, and her EEG showed eleptiform spike discharges. At 6 years of age, an antiepileptic drug was administered. At age 7 years, she was unable to stand, walk, or communicate with others. At age 13 years she (still) could not stand and required a wheelchair."

. . .

"In the present study, we examined the genome, epigenome and expression patterns of MZ twins discordant for RTT. We found that (1) the twins shared the same de novo MeCP2 mutation; (2) the de novo mutation was of paternal origin (occurred in spermatogenesis); (3) XCI (X Chromosome inactivation) did not differ in various peripheral tissues between the twins; (4) no inter-twin difference was found in whole gene sequences; (5) there were no differences in DNA methylation of the MeCP2 promoter region, nor did MeCP2 expression differ between the twins; (6) the DNA methylation status of a number of loci varied between the twins; (7) this DNA methylation difference was confirmed by the effect on expression of three genes, which may contribute to clinical differences between the twins. These results indicate that epigenetic differences, but not genetic differences, appear to be associated with the discordance between these twins." [Kunio, 2013]

FIG. 4 of the paper [Kunio, 2013] dramatically illustrates the results of a genome wide analysis of DNA methylation in the twins. Over 60 genes are shown in a red vs. green color scheme, with most of the genes (~⅔) being more methylated (redder) for the more severely afflicted twin (RS2) and the other ⅓ being less methylated (greener). The epigenetic differences are truly profound, even though there was no difference found between their X-inactivation patterns.

Other studies comparing the X-inactivation patterns of monozygotic twins have also found no significant relationship between X-inactivation skewing and RTT disease severity, confirming that the discordance observed between twins cannot be explained by X-inactivation skewing. For example, in a study of two pairs of sisters with RTT, where each pair of sisters had the same MeCP2 mutation and balanced X-inactivation, one individual from each pair could not speak or walk, and had a profound intellectual deficit, while the other individual could speak and walk and had only moderate intellectual disability [Grillo, 2013].

Similarly, a study of a mother (healthy) in which the mutant allele was predominantly active (75% vs. 25% in peripheral leukocytes) and her daughter with the identical mutation who developed severe RTT concluded that the presence of non-random XCI in the peripheral blood cells did not provide an explanation for the normal phenotype of the carrier mother [Ohinata, 2008]. The daughter's symptoms were described as:

"Early motor development of the patient was normal; she was able to hold her head at 4 months and could sit unaided at 7 months. Development abnormalities were first noted at the age of 10 months when she showed inconsolable crying and stopped smiling. The parents also noted that her face lacked expression. At 11 months of age, she lost her ability to sit unaided and became less interested in her toys. Physical examination showed hypotonia, strabismus, and intention tremor of her upper limbs. . . . At 13 months of age, she developed her first seizures characterized by tonic movement of the upper limbs and loss of consciousness. At the time, electroencephalography and brain magnetic resonance did not reveal any abnormalities. Thus, she was diagnosed with Rett syndrome, which was further confirmed by a mutation on the MeCP2 gene. At this point, the parents requested genetic testing to assess the risk of having more affected children."

Skewed X chromosome inactivation in the brain was investigated in nine RTT brains (obtained from the Harvard Brain Tissue Resource Center) [Gibson, 2004]. Balanced XCI patterns were observed in all neuroanatomical regions examined. They concluded that blood is more likely to undergo skewing than neural tissues in RTT patients.

In mouse models of RTT, male mice survive birth and develop the RTT phenotype at an earlier age than female mice, so most experiments are performed using male mice.

In RTT patients, the level of expression of MeCP2 is typically normal (as measured by the mRNA level), even though any MeCP2 protein that is produced is defective. Interestingly, there is another disease (MeCP2 duplication syndrome) where the over expression of MeCP2 produces RTT-like symptoms in both humans [Na, 2013] and mice [Na, 2012].

3.3 What is Known about MeCP2 Function?

MeCP2 is a protein which was already known to bind to DNA at a methylated "CpG site", which is a location on the DNA where a cytosine nucleotide is immediately followed by a guanine nucleotide, and the cytosine has a methyl group attached to carbon #5 ("5-methyl Cytosine"). This can have the effect of inhibiting the transcription of the following gene. MeCP2 is found in all cells of the body, but its most important functions seem to be in neurons. The association between MeCP2 mutation and Rett syndrome was discovered in 1999 [Amir, 1999], which greatly increased interest in the (mis)functions of this protein.

By 2001 it was discovered that deficiency of MeCP2 in CNS neurons results in a Rett-like phenotype in mice [Chen, 2001]. From then on, most experimental research on RTT has used mouse models of the disease.

3.3.1 Early Research Focuses on BDNF

In 2003 it was discovered that MeCP2 can control the level of BDNF (the "Brain Derived Neurotrophic Factor" protein) [Chen, 2003]. BDNF is involved in promoting neurite growth and synapse formation (learning) and in their preservation (memory).

In 2007 it was shown that restoration of MeCP2 function in adult mice (by activating the transgene expression of a functional MeCP2 gene) partially reverses the disease [Guy, 2007]:

"Our study shows that RTT-like neurological defects due to the absence of the MeCP2 gene can be rectified by delayed restoration of that gene. The experiments do not suggest an immediate therapeutic approach to RTT, but they establish the principle of reversibility in a mouse model and, therefore, raise the possibility that neurological defects seen in this and related human disorders are not irrevocable."

In 2009, treatment of MeCP2 mutant mice with "Insulin-like Growth Factor 1" (IGF-1) partially rescued 9 separate measures of RTT symptoms in mice: "(i) lifespan, (ii) locomotor activity, (iii) respiratory function, (iv) heart rate, (v) brain weight, (vi) concentration of a postsynaptic density protein in the motor cortex, (vii) spine density on motor cortex neurons, and (ix) cortical circuit plasticity." [Tropea, 2009]. Perhaps what is most impressive is the number of separate measures in which they were able to show improvement. Their justification for IGF-1 treatment was "Like BDNF, IGF-1 is widely expressed in the CNS during normal development . . . , strongly promotes neuronal cell survival and synaptic maturation . . . , and facilitates the maturation of functional plasticity in the developing cortex."

In 2010 it was shown in a mouse model of RTT that Valproic acid treatment increased BDNF and also normalized (made more similar to wild type) the levels of various proteins in neuroblastoma cells [Vecsler, 2010]. Furthermore, exogenous BDNF was shown to normalize the synaptic function of mouse brainstem slices [Kline, 2010], and glatiramer acetate treatment was shown to increase BDNF in a mouse model of RTT [Ben-Zeev, 2011].

Although the above treatments may make it seem that treating RTT only requires increasing BDNF, there are a multitude of genes whose expression is affected in RTT. Just increasing BDNF only partially improves the RTT phenotype. Other treatments have been found that seem to be more effective.

Table 1 below attempts to list all of the pharmaceutical treatments that have shown beneficial results in animal models of RTT (and also the tests that have been performed in humans). The list is probably incomplete, but it should be representative.

TABLE 1

| # | Disease Model | Treatment | Outcome | First author, year |
|---|---|---|---|---|
| 1 | Human females | L-Carnitine | Improved Patient Well Being Index, no effect on Hand Apraxia Scale assessment | Ellaway, 1999 |
| 2 | MeCP2$^{1/ox}$ mice | Choline | ↑ Dark-cycle locomotor activity, ↑ Motor function | Nag, 2007 |
| 3 | MeCP2$^{tm1.1Jae}$ mice | Ampakine | Normalization of breathing, ↑ BDNF | Ogier, 2007 |
| 4 | MeCP2$^{tm1.1Bird}$ mice | Desipramine | ↓ Apneas, ↑ TH expressing neurons | Roux, 2007 |
| 5 | MecP2-null mice | IGF-1 | ↑ Lifespan, ↑ Normal breathing, ↑ Motor function | Trpoea, 2009 |
| 6 | MeCP2 knockdown in human SK-NSH cells | Valproic acid | Normalization of proteins in neuroblastima cells: ↑ MeCP2, ↑ BDNF, ↑ AcH3 | Vecsler, 2010 |
| 7 | MeCP2$^{tm1.1Jae}$ mice | Exogenous BDNF | Normalized synaptic function in brainstem slices | Kline, 2010 |
| 8 | MeCP2$^{tm1H2O}$ mice | Glatiramer acetate | ↑ BDNF | Ben-Zeev, 2011 |
| 9 | MeCP2$^{tm1.1Jae}$ mice | 7,8-dihydroxyflavone | ↑ Lifespan, ↑ Normal breathing, ↑ Motor function | Johnson, 2011 |
| 10 | MeCP2$^{-/y}$ mice | Fingolimod | ↑ Lifespan, ↓ Hind-limb clasping, ↑ Motor function | Deogracias, 2012 |

TABLE 1-continued

| # | Disease Model | Treatment | Outcome | First author, year |
|---|---|---|---|---|
| 11 | MeCP2[1lox] mice | Acetyl-L-Carnitine | ↑ Forepaw grip strength, ↑ Motor function | Schaevitz, 2012 |
| 12 | MeCP2[tm1.1Jae] mice | Ketamine | Improved PPI of the ASR (cognitive function) | Kron, 2012 |
| 13 | Human females | ω-3 PUFA | ↑ Hand use, ↑ Nonverbal communication, ↑ Motor function, Normalized breathing | De Felice, 2012 |
| 14 | MeCP2[tm1.1Bird/+] mice | Fluvastatin | Delayed symptoms, ↑ Lifespan, ↑ Motor function | Buchovecky, 2013 |
| 15 | Human females | Topiramate | ↓ Apneias | Krajnc, 2013 |
| 16 | Human females | ω-3 PUFA | Normalized 10 out of 16 Acute Phase Response plasma protein levels | De Felice, 2013 |
| 17 | MeCP2 KO mice | Triheptanoin | ↑ Lifespan, ↑ Social interaction, ↑ Motor function | Park, 2014 |
| 18 | MeCP2[tm1.1Jae] mice | Valproic acid | Improved neurological symptoms, ↑ Motility, Normalized gene expression in brain | Guo, 2014 |
| 19 | Human females | IGF-1 | ↓ Apneias | Khwaja, 2014 |
| 20 | MeCP2[tm1.1Bird] mice | Levodopa | ↑ Lifespan, ↓ Hind-limb clasping, ↑ Motor function, ↓ Tremor, ↑ TH expressing neurons | Szczesna, 2014 |
| 21 | Human females | ω-3 PUFA | ↓ Inflammation (isoprostanes), ↑ Bone density | Signorini, 2014 |
| 22 | MeCP2-mutated human fibroblasts | Tubastatin A | Protects mictotubules from depolymerization (and improves the transport of BDNF in neurons) | Gold, 2015 |
| 23 | Silenced MeCP2 in mouse neurons | Pentobarbatol | ↑ dendrite growth, ↑ Synaptic transmission (calcium spikes) | Ma, 2015 |

Abbreviations: ↑ increased, ↓ decreased

Although 4 of the 8 treatments that were tested up to 2011 (numbers 1-8 in the list) involved increased BDNF, the evidence from Chen, 2003 (above), which I described as "MeCP2 can control the level of BDNF" actually showed that MeCP2 normally depresses the expression of the BDNF gene, and only increases the BDNF protein level when there is excess calcium in the neuron (e.g. after the neuron has "fired"). MeCP2 is described as "a selective regulator of neuronal gene expression. Activity-dependent transcription underlies the ability of the nervous system to convert the effects of transient stimuli into long-term changes in brain function" (i.e. learning and memory)[Chen, 2003].

3.3.2 Later Research Investigates a Broad Range of Treatments

The 16 remaining treatments listed in Table 1 use 14 different pharmacological agents, and although they all show some benefit (otherwise they wouldn't be in the table), two stand out: (1) The three experiments using Omega-3 polyunsaturated fatty acids ("ω-3 PUFA") were conducted using human females with RTT, and showed definite benefits for the patients (improvements in hand use, nonverbal communication, motor function, and breathing) [De Felice, 2012] and in biomarkers for inflammation [De Felice, 2013; Signorini, 2014]. (2) The experiments with Fluvastatin treatment using mice which delayed disease symptom development and improved motor function and lifespan [Buchovecky, 2013].

3.3.2.1 Treatment with ω-3 PUFA

This research group had previously established that a variety of markers of oxidative stress are elevated in RTT patients [De Felice, 2009]. Oxidative stress markers included intraerythrocyte non-protein-bound iron (NPBI; i.e., free iron, plasma NPBI, $F_2$-isoprostanes ($F_2$-IsoPs, as free, esterified, and total forms), and protein carbonyls. Markers of oxidative stress were significantly increased in RTT subjects: intraerythrocyte NPBI (2.73 fold, "×2.73"), plasma NPBI (×6.0), free $F_2$-IsoP (×1.85), esterified $F_2$-IsoP (×1.69), total $F_2$-IsoP (×1.66), and protein carbonyls (×4.76).

Based upon this evidence of enhanced oxidative stress and lipid peroxidation in RTT patients, they tested the possible therapeutic effects ω-3 PUFAs on the clinical symptoms and oxidative stress biomarkers in the earliest stage of RTT. The treatment group (treated with fish oil, which is high in ω-3 PUFAs) and the control group each had 20 patients, and the study duration was 6 months. In the treatment group, significant improvements were observed for motor/independent sitting, ambulation, hands use, nonverbal communication, and respiratory dysfunction, while a non-significant trend was observed for language [De Felice, 2012]. Using the RTT Clinical Severity Score (CSS) [Neul, 2008] to evaluate the patients, the untreated group had their CSS increase from 37 to 39 (range 0-58), while the treatment group had their CSS improve from 37 down to 21. A short video clip made from parents' home movies is available at: link.springer.com/article/10.1007%2Fs12263-012-0285-7.

Secondary outcomes (measurements of oxidative stress) include a marked decrease in plasma $F_2$-dihomo-IsoPs (−86.3%), $F_2$-IsoPs (−55.15%), NPBI (−42.2%), $F_4$-NeuroPs (−40.3%), and intraerythrocyte−NPBI (−46.3%). No significant improvement in any of the examined oxidative stress markers was observed in the untreated group.

Another study by the same group measured the blood plasma proteome profile with untreated RTT, after treatment with ω-3 PUFAs as fish oil for 12 months, and healthy controls [De Felice, 2013]. Sixteen proteins were found to be significantly differentially expressed in the RTT patients (compared to controls). In untreated patients, 10 of the proteins upregulated in the range of +1.17 to +2.07 fold and 6 of the proteins were downregulated in the range of −1.32 to −2.56 fold (Table 1 of De Felice, 2014). After 12 months of treatment, the protein expressions of the RTT patients were normalized with the previously upregulated now being in the range of +1.26 to −1.03 fold, while the protein expressions that were downregulated now being in the range of +1.33 to +1.03 fold compared to controls (calculated from Table 1 of De Felice, 2013).

Recent work by the same group has confirmed that all mouse models for RTT that have been tested show evidence of oxidative stress and lipid peroxidation (increased plasma NPBI, $F_2$-IsoPs and $F_2$-dihomo-IsoPs). And brain-specific MeCP2 gene reactivation fully rescues brain oxidative stress, returning to the level of age-matched wild type litter-mates [De Felice, 2014].

3.3.2.2 Treatment with Fluvastatin

A genetic screen for suppressors of symptoms of RTT in a MeCP2 mouse model was used to try to identify pathways that are responsible for disease pathology. They raised 679 MeCP2$^{tm1.1Bird}$/Y mice most of which had severe enough neurological abnormalities that they had either already died or had to be euthanized by 6-16 weeks of age; however, some of the mice showed amelioration of one or more health assessment traits. Further selection followed by genetic mapping identified a nonsense mutation of the Sqle gene (encoding the enzyme squalene monooxidase) which is part of the pathway for cholesterol synthesis. [Buchovecky, 2003]

They then hypothesized that the heterozygous Sqle mutation ameliorates a previously unrecognized dysregulation of cholesterol metabolism in MeCP2-null mice. They reasoned that a pharmacologic inhibitor of cholesterol synthesis might produce an attenuation of symptoms comparable to that of the genetic inhibitor (mutated Sqle gene) in MeCP2-null mice.

Fluvastatin (or Lovastatin, which was also successfully tested) can cross the blood-brain barrier, and therefore is suitable for use in treating a neurological disorder. Fluvastatin treated MeCP2-null mice showed improved rotarod performance (motor function, 200 seconds time to fall versus 60 seconds for MeCP2-null controls) and increased longevity (no deaths during the 270 day experiment versus 30% mortality for the MeCP2-null controls). Lipid profiles (serum cholesterol, total liver lipids) were somewhat normalized by the Fluvastatin treatment (closer to the values for wild type controls).

Caveats are that they did not evaluate (or at least didn't report) the effects on other abnormalities known to be associated with RTT. Also the "combined health score" (limbclasping, tremors, and activity) [Guy, 2007] got worse with successive Fluvastatin treatments (from 5 to 10 treatments), especially when the dosage was increased, to the point where there was no significant benefit from the Fluvastatin treatment if the dosage was the 10× dose [Buchovecky, 2003, Supplementary FIG. 10].

The loss of effectiveness when the Fluvastatin dosage is increased may be due to the inhibition of synthesis of gerangygeranoil that occurs with statin treatment (which inhibits cholesterol synthesis at the HMGCR enzyme, see FIG. 2). But the synthesis of gerangygeranoil is probably increased in the Sqle mutant mouse, due to the loss of Sqle activity. Therefore, statin treatment diverges from the mutant Sqle mouse model in this respect, perhaps with great significance.

"Cholesterol turnover is also required to produce gerangygeranoil, a product of HMGCR upstream of SQLE that is essential for learning and synaptic plasticity, and is important for the interaction between neurons and astrocytes at the synapse." [Buchovecky, 2003]

The loss of effectiveness may also be due to cholesterol synthesis being essential for synapse development [Suzuki, 2007] as well as for gerangygeranoil synthesis [Kotti, 2006].

Perhaps the lower dose of Fluvastatin preserves enough cholesterol synthesis to allow synapses to be formed.

In summary, various treatments have shown benefits in mouse models of Rett syndrome. But except for treatment with ω-3 PUFAs, apparently there has not been a clear enough perception of benefit (or of safety) to induce clinicians (or their Institutional Review Boards) to move on to human clinical trials, even for treatments that have already been approved for use in clinical trials involving children (e.g. the successful treatment with Fluvastatin for children and adolescents with heterozygous familial hypercholesterolaemia [van der Graff, 2006]).

3.4 Further Evidence that RTT is an Epigenetic Disease 3.4.1 A Brief Introduction to Epigenetics There is more to genetics than the DNA sequence that determines the genes. Not only are genes themselves inherited, the expression patterns for the genes is inherited as well. This is true both for the individual child and also for the cells within the child, where daughter cells inherit their gene expression patterns whenever a cell divides.

Commonly, a daughter cell will inherit a gene expression pattern which is different from the gene expression pattern of its parent cell. The parent cell may be a pluripotent stem cell and its daughter cells may include tissue-specific stem cells. And their daughter cells may be further differentiated to perform their specific functions. All of these cells share the same DNA sequence, but their DNA has been epigenetically modified in order to restrict the genes that are expressed within each specific type of cell after differentiation.

For example, a bone marrow stem cell (e.g. a hemocytoblast) can have either a "common myeloid progenitor" cell or a "common lymphoid progenitor" cell as a daughter cell. The common myeloid progenitor cell can in turn have either a megakaryocite, an erythrocyte, a mast cell or a myeoblast as a daughter cell. Of these, only the erythrocyte and the mast cell are fully differentiated (the other cell types can have daughter cells that are more further differentiated).

One way that the gene expression of daughter cells is restricted is by the methylation of specific nucleotides in the DNA (the cytosines of CpG sites), especially at CpG islands within the promotor region for the genes. The addition of a methyl groups to cytosine nucleotides (cytosine methylation) has the effect of reducing gene expression and has been found in the cells of every vertebrate examined. When DNA is being copied for cell division, the methylation pattern is copied as well, so that (in the absence of differentiation) the gene expression pattern for the daughter cell will start out as that of its parent. Or the methylation pattern will change in a cell-specific way when producing a daughter cell that is differentiated from its parent.

During the life of a cell, the methylation pattern can change. There is constant "methylase" and "demethylase" enzyme activity, which tends to maintain the existing pattern, but can respond to intranuclear (and ultimately to extracellular) signaling as well. However, for any specific type of cell the methylation pattern of the DNA should remain relatively constant (especially in the "CpG islands" in the promotor regions for genes), because this is what keeps the cell-type constant. But even when the methylation pattern remains constant, there is continuous turnover of the methylation at individual CpG sites within methylated CpG islands. The methyltransferase enzymes (especially DNMT1) will remethylate a CpG within a methylated CpG island in order to keep the CpG island methylated as a whole, even in the presence of variations in the methylation of individual CpG sites within the CpG island.

Another way that the gene expression of cells is epigenetically controlled is by controlling the access of transcription factors to the DNA. Small lengths of DNA are wound on top of "nucleosome" structures that are composed of "histone" proteins. If a section of DNA is tightly wound on top of a nucleosome, it is unavailable to transcription factors and the expression of its associated gene will be limited. DNA that is free (not attached to nucleosomes, or at least temporarily released), is more available to transcription factors and its associated gene is more likely to be expressed.

Both the location of nucleosomes on the DNA and tightness of DNA attachment is controlled by specialized proteins that can modify the histones. In particular, there are "histone acetyltransferase" (HAT) enzymes that can attach acetyl groups to the "tails" of histones, with the effect of loosening the winding of DNA on the nucleosome. And there are "histone deacetylase" (HDAC) enzymes that can remove acetyl groups from the histone tails. And there are "histone deacetylase inhibitor" (HDACi) molecules that can prevent the HDAC proteins from deacetylating the histones, thereby keeping an acetylated histone acetylated and the DNA attached to its nucleosome accessible for transcription.

There are actually a wide variety of modifications that occur on histone tails (e.g. they can also be methylated, phosphorylated, or ubiquinated at various positions). Histone modifications occur more often than modifications to the DNA methylation pattern, and can fine-tune the operation of the cell. But there is some cross-talk in both ways between histone modifications and DNA methylation, which helps preserve the stability of the cell-type.

3.4.2 Shared Histone Modifications Across Various RTT Patients

Most studies of RTT involve only human females (or mouse males) that have a mutated MeCP2 gene. But one study involving humans included RTT patients whose MeCP2 genes were both functional [Kauffman, 2005]. Of the 17 patients with RTT, 11 had MeCP2 mutations ("RTTPos") and 7 did not ("RTTNeg"). There were also 10 gender-matched controls.

Among the patients with MeCP2 mutations, three had the R270X truncation mutation, two had the R168X truncation mutation, and one of each had the Del796 deletion, R255X truncation, V288X truncation, R306C missense, T158M missense, and R294X truncation mutations. A reasonably diverse set.

The presence (HAc+) or absence (HAc-) of histone acetylation was determined by immunochemistry in lymphocytes for histone H3 and for histone H4. Averages for the 3 groups (Control, RTTPos and RTTNeg) were as follows:

|  | H3Ac+ | H3Ac- | H3Ac+/H3Ac- |
| --- | --- | --- | --- |
| Control | 851.7 | 936.4 | 3.69 ± 2.14 |
| RTTPos | 1030.6 | 379.1 | 0.52 ± 0.21 |
| RTTNeg | 2045.7 | 863.5 | 0.44 ± 0.11 |
|  | H4Ac+ | H4Ac- | H4Ac+/H4Ac- |
| Control | 820.6 | 648.9 | 0.96 ± 0.33 |
| RTTPos | 266.4 | 422.4 | 3.01 ± 1.06 |
| RTTNeg | 476.8 | 584.8 | 2.39 ± 1.55 |

Amazingly, all of the Controls can be distinguished from all of the RTT patients by these simple measurements, regardless of the patient's type of MeCP2 mutation, or even when MeCP2 is not mutated at all. For example, the lowest H3Ac+/H3Ac- for any control was 1.55 (3.69-2.14) but the highest H3Ac+/H3Ac- for any patient was 0.73 (0.52+0.21). Similarly, the H4Ac+/H4Ac- values for the Controls were widely separated from the H4Ac+/H4Ac- of the patients.

In further experiments, they determined that for the specific lysine H3K9 the ratio of acetylation to non-acetylation for controls was 5.02 but for RTTPos it was 0.54 and for RTTNeg it was 0.32. Similarly, for the specific lysine H3K14, the ratio of acetylation to non-acetylation for controls was 2.90 but for RTTPos it was 0.82 and for RTTNeg it was 0.96.

In further experiments, they determined that for the specific lysine H3K4 the degree of methylation for controls was 0.145 but for RTTPos it was 0.023 and for RTTNeg it was 0.014. Similarly, for the specific lysine H3K9, the degree of methylation for controls was 0.538 but for RTTPos it was 0.054 and for RTTNeg it was 0.046.

It should be noted that H3K9Ac, H3K14Ac, H3K4Me and H3K9Me are all positively related to gene expression, so their relatively high values in Controls compared to patients indicates that lymphocyte genes are being expressed in Controls that are not being expressed in the RTT patients, regardless of the type of MeCP2 mutation or even whether MeCP2 is mutated at all.

This supports the observation by Kunio quoted above that even in twins with an identical MeCP2 mutation, "These results indicate that epigenetic differences, but not genetic differences, appear to be associated with the discordance between these twins."

In other words, RTT can be viewed to be primarily an epigenetic disease which has MeCP2 mutations as a significant risk factor.

SUMMARY OF THE INVENTION

4. Summary of the Invention

There are various diseases and disorders which have inappropriate gene expression in cells, which is largely under epigenetic control. For example: (1) cellular differentiation involves the silencing of genes whose expression is inappropriate for that specific type of cell, while enabling the expression of the genes that are appropriate to be (at least sometimes) expressed, (2) beyond the silencing of genes, the expression of genes in each cell can also be fine-tuned by epigenetic control, (3) because the epigenetic state of gene silencing in a cell is heritable, an inappropriate epigenetic pattern of gene silencing in one cell can be inherited as the default epigenetic pattern of gene silencing for its daughter cells.

Although most epigenetic markers are heritable, they remain changeable, and may even be changed as a result of dietary input. However, there is an inherent stability for every specific type of cell which causes the epigenetic pattern to tend towards a pattern that is appropriate for that type of cell.

In other words, ectopic (inappropriate for that location, for that type of cell) epigenetic markers are metastable (not permanently stable, but not necessarily changing any time soon), while genetic markers that are appropriate for that cell type are inherently stable (but may none the less be modifiable).

Particular types of cells may have multiple epigenetic patterns that are appropriate for that cell type, with the ability to switch between a set of alternative patterns. This can happen according to the developmental stage of the individual. Each of these patterns can be stable, requiring an external input to switch them to the next appropriate pattern.

The present invention uses dietary ingredients (e.g. in a nutraceutical or a dietary supplement) to modify the epigenetic pattern of some cells in the body so that they will transition to appropriate epigenetic patterns that alleviate a disease or disorder.

Specifically, dietary ingredients that provide bioavailable acetate can increase the acetylation of proteins (such as histone proteins) and other biomolecules with a net effect on gene expression profiles of cells, disrupting their dysfunctional epigenetic patterns and causing them to adopt more appropriate patterns for the treatment of these diseases and disorders.

In an aspect, the present disclosure encompasses a method of treating a genetic or epigenetic disease or disorder. The method comprises the administration to an animal a therapeutically effective dose of a composition containing acetate selected from the group of calcium acetate, magnesium acetate, sodium acetate, potassium acetate, ethylacetate, or any combination thereof, said composition forming acetate in the body and said acetate increasing the level of protein acetylation in the subject. The amount of acetate administered per day may be about 100 mg to about 15,000 mg of acetate per day. In various embodiments, the amount of acetate may also be about 100 mg to about 5000 mg per day, about 200 mg to about 2000 mg per day, or about 500 mg to about 1000 mg per day. In various other embodiments, the amount of acetate may be about 375 mg to about 15,000 mg per day, about 750 mg to about 7500 mg per day, about 750 mg to about 5000 mg per day, or about 750 mg to about 3000 mg per day. In certain embodiments, the composition is a nutraceutical or a dietary supplement.

In another aspect, the present disclosure encompasses a method for treating Rett Syndrome in a subject in need thereof. The method comprises administering to the subject about 100 mg to about 15,000 mg of acetate per day, wherein the acetate is selected from calcium acetate, magnesium acetate, sodium acetate, potassium acetate, ethylacetate, or any combination thereof. In various embodiments, the amount of acetate may also be about 100 mg to about 5000 mg per day, about 200 mg to about 2000 mg per day, or about 500 mg to about 1000 mg per day. In various other embodiments, the amount of acetate may be about 375 mg to about 15,000 mg per day, about 750 mg to about 7500 mg per day, about 750 mg to about 5000 mg per day, or about 750 mg to about 3000 mg per day. The daily amount of acetate may be formulated as a composition to be administered in one or doses. In certain embodiments, the composition may be a nutraceutical or a dietary supplement. Administration of the acetate may increase protein (including but not limited to histones) acetylation in blood lymphocytes as well as in other cell types, increase synaptic function, increase synaptic formation, increase expression of BDNF, improve memory, improves learning, and/or improve motor function. Methods for measuring these effects are known in the art.

In another aspect, the present disclosure encompasses a method for treating cancer in a subject in need thereof. The method comprises administering to the subject about 100 mg to about 15,000 mg of acetate per day, wherein the acetate is selected from calcium acetate, magnesium acetate, sodium acetate, potassium acetate, ethylacetate, or any combination thereof. In various embodiments, the amount of acetate may also be about 100 mg to about 5000 mg per day, about 200 mg to about 2000 mg per day, or about 500 mg to about 1000 mg per day. In various other embodiments, the amount of acetate may be about 375 mg to about 15,000 mg per day, about 750 mg to about 7500 mg per day, about 750 mg to about 5000 mg per day, or about 750 mg to about 3000 mg per day. The daily amount of acetate may be formulated as a composition to be administered in one or doses. In certain embodiments, the composition may be a nutraceutical or a dietary supplement. Administration of the acetate may increase protein acetylation (including, but not limited to, histone acetylation), inhibit proliferation of cancer cells, inhibit tumor growth, reduce a tumor's size, decrease methylation at CpG islands in cancerous cells in the subject, and/or increase expression of one or more tumor suppressor genes. Methods for measuring these effects are known in the art.

In another aspect, the present disclosure encompasses a method for treating a trinucleotide repeat disorder in a subject in need thereof. The method comprises administering to the subject about 100 mg to about 15,000 mg of acetate per day, wherein the acetate is selected from calcium acetate, magnesium acetate, sodium acetate, potassium acetate, ethylacetate, or any combination thereof. In various embodiments, the amount of acetate may also be about 100 mg to about 5000 mg per day, about 200 mg to about 2000 mg per day, or about 500 mg to about 1000 mg per day. In various other embodiments, the amount of acetate may be about 375 mg to about 15,000 mg per day, about 750 mg to about 7500 mg per day, about 750 mg to about 5000 mg per day, or about 750 mg to about 3000 mg per day. The daily amount of acetate may be formulated as a composition to be administered in one or doses. In certain embodiments, the composition may be a nutraceutical or a dietary supplement. Administration of the acetate may increase protein acetylation (including, but not limited to, histone acetylation), inhibit proliferation of cancer cells, inhibit tumor growth, reduce a tumor's size, and/or decrease methylation at CpG islands in the subject. Methods for measuring these effects are known in the art.

Other aspects and iterations of the invention are described more thoroughly below

BRIEF DESCRIPTION OF THE DRAWINGS

5. Brief Description of the Drawings

The application file contains at least one photograph executed in color. Copies of this patent application publication with color photographs will be provided by the Office upon request and payment of the necessary fee.

FIG. 1A-H shows various molecules of interest. (A) Acetyl group; (B) Acetylated lysine; (C) Acetyl-CoA; (D) Acetic Acid; (E) Butyrate; (F) ω-3 Fatty Acid; (G) Valproic Acid; (H) Triheptanoin.

FIG. 10A-F shows more molecules of interest. (A) Sodium Acetate; (B) Potassium Acetate; (C) Dichloroacetate; (D) Magnesium Acetate; (E) Calcium Acetate; (F) Glycerin Triacetate.

Figure 2:
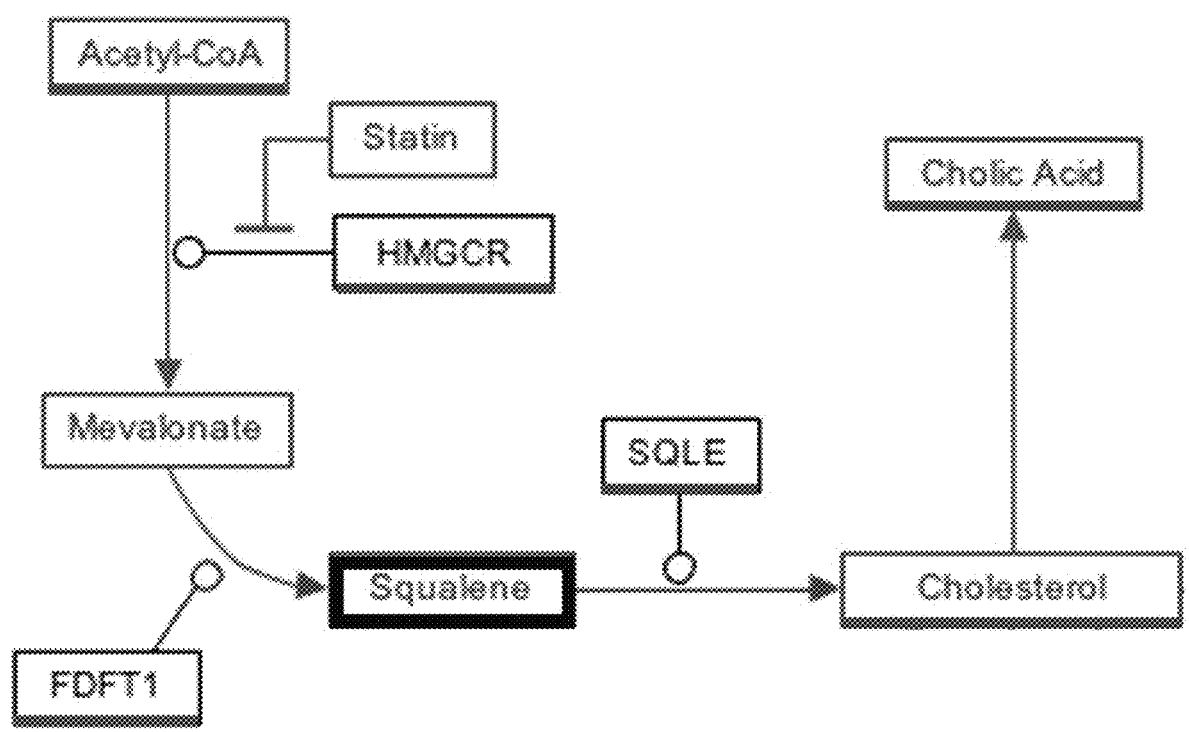
FIG. 2 (derived from "Squalene_pathway_map.png"; Wikipedia) shows the role of the SQLE enzyme in cholesterol synthesis.

DETAILED DESCRIPTION OF ILLUSTRATIVE EMBODIMENTS 6.1 Pharmacological Treatments for RTT Revisited Treatment with Valproic acid shows up twice in the listing of beneficial treatments (Table 1), with the benefits of: (1) normalizing protein levels, (2) increased MeCP2 expression (e.g. from the good gene), (3) increased BDNF, (4) increased histone H3 acetylation, (5) improved neurological symptoms, (6) improved motility, and (6) normalized gene expression in the brain. Valproic acid is well known as a histone deacetylase inhibitor (HDACi), which increases the acetylation of histones, and this is recognized as its principal pharmacological activity.

Other treatments listed in Table 1 which have HDACi activity as their principal pharmacological activity are Topiramate and Tubastatin A. I was curious which other of the treatments have known histone acetylation activity (in addition to whatever other activities they have). The results of this survey are listed in Table 2 below, which includes a brief description of the histone acetylation mechanism and a reference that provides more details. Clearly, the vast majority of beneficial pharmacological treatments have at least the side effect of increasing histone acetylation. (Even some of the other beneficial treatments may have histone acetylation as an undocumented side effect, but I wasn't able to find a reference to document it.) The list of treatments is diverse, but their methods of action may not be as diverse as it would otherwise seem.

TABLE 2

| # | Disease Model | Treatment | ↑ HAc ? | Histone acetylation | Author, year |
|---|---|---|---|---|---|
| 1 | Human females | L-Carnitine | Y | Increases Acetyl-CoA | Madiraju, 2009 |
| 2 | MeCP2$^{1/ox}$ mice | Choline | N | | |
| 3 | MeCP2$^{tm1.1Jae}$ mice | Ampakine | N | | |
| 4 | MeCP2$^{tm1.1Bird}$ mice | Desipramine | N | | |
| 5 | MecP2-null mice | IGF-1 | Y | Increases H3, H4 Histone acetylation in the brain | Sun, 2006 |
| 6 | MeCP2 knockdown in human SK-NSH cells | Valproic acid | Y | HDACi | Eyal, 2004 |
| 7 | MeCP2$^{tm1.1Jae}$ mice | Exogenous BDNF | N | | |
| 8 | MeCP2$^{tm1HzO}$ mice | Glatiramer acetate | Y | Contains acetate | |
| 9 | MeCP2$^{tm1.1Jae}$ mice | 7,8-dihydroxyflavone | N | | |
| 10 | MeCP2$^{-/y}$ mice | Fingolimod | Y | HDACi | Hait, 2014 |
| 11 | MeCP2$^{1/ox}$ mice | Acetyl-L-Carnitine | Y | Increases Acetyl-CoA | Madiraju, 2009 |
| 12 | MeCP2$^{tm1.1Jae}$ mice | Ketamine | Y | HDACi activity in the Nucleus Accumbens region of the brain | Reus, 2013 |
| 13 | Human females | ω-3 PUFA | Y | Increases the HDACi activity of butyrate | Xu, 2006 |
| 14 | MeCP2$^{tm1.1Bird/+}$ mice | Fluvastatin | Y | Inhibits HDAC activity and induces histone acetylation | Lin, 2008 |
| 15 | Human females | Topiramate | Y | HDACi | Eyal, 2004 |
| 16 | Human females | ω-3 PUFA | Y | Increases the HDACi activity of butyrate | Xu, 2006 |
| 17 | MeCP2 KO mice | Triheptanoin | Y | Metabolizes to Acetyl-CoA | Park, 2014 |
| 18 | MeCP2$^{tm1.1Jae}$ mice | Valproic acid | Y | HDACi | Eyal, 2004 |
| 19 | Human females | IGF-1 | Y | Increases H3, H4 Histone acetylation in the brain | Sun, 2006 |
| 20 | MeCP2$^{tm1.1Bird}$ mice | Levodopa | Y | Histone acetylation, via phosphorylation | Inden, 2012 |
| 21 | Human females | ω-3 PUFA | Y | Increases the HDACi activity of butyrate | Xu, 2006 |
| 22 | MeCP2-mutated human fibroblasts | Tubastatin A | Y | HDACi | Gold, 2015 |
| 23 | Silenced MeCP2 in mouse neurons | Pentobarbatol | N | | |

6.2 the Development of RTT Revisited.

Infants with RTT develop normally up to an age of 6 to 18 months (disease onset) including their ability to learn. This age corresponds to the developmental stage where the MeCP2 protein level in neurons increases in normal (non-RTT) infants and brain glucose metabolism increases [Shahbazian, 2002]. Infants with RTT may either develop a normal increase in MeCP2 (mutant, non-functional) protein, or the mutation (e.g. a deletion) may prevent the MeCP2 from being produced at all. In either case, disease symptoms first appear at the developmental stage where MeCP2 should start performing its function. Without functioning MeCP2, learning seems to stop, and previously learned skills are gradually lost.

> "[In RTT] the regression phase is best explained by a delayed onset of neuronal dysfunction." [Shahbazian, 2002]

Normal infants actually change the way that they learn at about this age (e.g. when they reach this developmental stage). According to Liston, 2002:

> "Infants of 6 months old can remember events for up to 24 hours, which extends to up to a month when they are 9 months old. . . . In humans, the brain undergoes important changes towards the end of the first year, including the growth and differentiation of dendrites in the hippocampus, which continue into the second year. These developmental processes should increase the efficiency of integration and registration of information in the neocortex, and in the prefrontal cortex in particular. . . .
> 
> [Their experiments show that before this developmental transition infants need repeated exposure to something in order to learn it (they learn slowly), but that after this transition they can remember something that has happened only once.]
> 
> . . . our results support the popular belief that at 9 months the hippocampus and regions of the frontal cortex are not yet fully mature. They also indicate that there is a neurobiological component to memory enhancement across the second year, contrary to early assumptions that this is entirely attributable to experience."

In other words, at this stage of development neurons change the way they work, and instead of using repetition to develop synaptic connections, they can turn on a "synapse formation machine" in response to a single experience.

It seems that for infants with RTT, at this stage of development, the old way of learning gets turned off and the new way gets turned on. But the new way doesn't work.

Interestingly, the same thing happens in RTT mice. For both humans and mice, there is an increase in total MeCP2 protein as neurons differentiate [Dragich, 2007], but the mouse models allow more detailed analysis because brain tissue samples can be analyzed for any age of mouse. There are two splice variants for the MeCP2 gene, MeCP2e1 and MeCP2e2. At about 21 days of age (week 3), the distribution profile changes with MeCP2e2 becoming predominantly localized to the dorsal thalamus and cortical layer V [Dragich, 2007], indicating that the neurons in these regions are further differentiated than neurons in other regions of the brain. This is when (at week 4) symptoms of RTT first become evident in the mice. See FIG. 3, "RTT Symptom Score", [from FIG. 1C of Weng, 2011].

6.3 Function of MeCP2 Revisited

The main function of MeCP2 in neurons is to produce "switchable on or off" chromatin condensation which when switched off can simultaneously enable the expression of a whole set of genes at one time. In effect, this turns on or off a "synapse formation machine". The MeCP2 protein has a binding site that is specific for methylated CpG (e.g. a DNA location) at one end of the protein and an "A:T hook" at the other end (e.g. it specifically binds to a DNA location that has a high density of A and T nucleotides). Along the length of MeCP2, it may be attached to the DNA (causing "DNA compaction" and preventing the expression of genes) or the MeCP2 can separate from that section of the DNA. Whether or not this stretch of DNA is attached to the MeCP2 depends upon the absence or presence of calcium, which enters the neuron when the neuron fires. [This is a simplified description of a multi-step process. For more details, see Tao, 2009]

In effect, when the neuron fires, this stretch of DNA becomes available for gene transcription. The BDNF gene is one of these genes, so the expression of BDNF (and hence the production of BDNF protein) gets switched on in response to calcium [Chen, 2003; Zhaolan, 2006].

In the absence of MeCP2 (and even in the presence of MeCP2), BNDF expression requires activation of its promoters. BDNF is a neurotrophin (promotes nerve growth, synapse formation, and synapse maintenance) which is produced by neurons, secreted from vesicles, and sensed by cells that have BDNF receptors on their surface. So BDNF does much of the signaling involved in the cooperative synapse formation between neurons, and is probably involved in early infant learning (from repetitive experience) as well as in MeCP2 dependent learning (after the associated developmental stage).

What may be needed is a way to turn back on the early method of learning, even though the RTT patient has gotten old enough that this mode of learning has been turned off.

6.4 Epigenetics Revisited

The mapping from genotype to phenotype for every cell in the body is controlled by epigenetics. We are gradually learning the mechanisms involved, which include at least: (1) DNA modification (CpG island methylation, CpG site methylation, chromatin condensation, histone attachment, histone positioning, MeCP2 attachment, RNA attachment, transcription factor attachment . . . ), (2) histone modification (acetylation, methylation, phosphorylation, ubiquination, . . . ), (3) various forms of RNA (including siRNA, non-coding RNA, long non-coding RNA, and micro RNA). Note that the production of any particular RNA from the DNA can be controlled by gene expression, controlled by pseudo gene expression, or the RNA may be produced merely because the "junk DNA" is being transcribed.

Although in general the phenotype of any individual cell remains stable, the epigenetic program for a cell can be modified in exceptional circumstances. For example, when a cell divides, the expression of specific transcription factors can produce different phenotypes for of each of the daughter cells.

> "During the differentiation process, the developmental capacity of totipotent cells in the early embryo is progressively lost as these undertake cell fate decisions. This process is driven by the expression of cross-antagonistic transcription factors (TF) promoting development towards one cell fate while repressing an alternative differentiation path. Cell fate decisions are fortified by progressive acquisition of epigenetic modifications at both the DNA and chromatin level. While cell identity is undeniably dictated by the expression profile guided by cell type-specific TFs, the robustness of the acquired transcriptional state is crucially dependent upon the configuration of the chromatin context in which these TFs operate. . . .

. . . In a model whereby TF cross-antagonism is the central mechanism by which cell fate is determined, cell fate transitions, such as those observed during de-differentiation and trans-differentiation events, are possible through ectopic expression of the required cell type instructive TFs." [Nashun, 2015]

With regards to RTT, it is clear that neurons have two "differentiations", one for "repeated experience" based learning and another for "one shot" learning from a single experience. What may be needed for RTT patients is a method for switching the differentiation state of the neuron back, in order to re-enable the "repeated experience" mode of learning for the patient. To do this we need to epigenetically transition the cell to its previous neuronal phenotype.

"Developmental progression from a totipotent to a differentiated cell is a gradual process accompanied by deposition of repressive histone marks and by increasing compaction." [Nashun, 2015]

But going back to a previous differentiation state involves making the histones less restrictive (which will naturally make the DNA less compact). In other words, we need to increase the histone acetylation. (It is not clear at this stage whether we can permanently change the state with one treatment, or whether we will need to continue the treatment for life. The assumption is that if we stop the treatment, the neuron could transition to the more "developed" phenotype. Therefore, we should expect to treat the RTT patient for life, and the treatment should have very low (or no) toxicity.)

6.5 Why Aren't Epigenetic Treatments Highly Toxic?

Epigenetic treatments are generally not highly toxic because there are multiple epigenetic feedback mechanisms to sustain the stability of the cellular phenotype. Although the expression of each individual gene is largely controlled by the combination of its own promoters' methylation and its histones' acetylation/methylation state, it also responds to the RNA that is transcribed by other genes (and pseudo genes) which tend to reinforce the persistence of the cellular phenotype.

In other words, if the expression of an individual gene becomes disturbed in a way that could change the cell's phenotype, it will tend to be corrected soon due to the combined effect of the pattern of the various RNAs that were already produced (based upon the existing phenotype), as described below. It is only those genes that do not change the cell's phenotype that are freely responsive to the signaling environment of the cell.

6.5.1 X-Inactivation Revisited

The stability of X-inactivation illustrates the role of RNA in overcoming perturbations to the cell's methylation/acetylation signaling. In an experimental system, the impact of separately perturbing each of the epigenetic aspects involved (methylation, acetylation, and Xist RNA synthesis) showed that none of these could, when individually manipulated, switch off the X-inactivation of the cell [Csankovszki, 2001]. Autofluorescence was used to detect X-inactivation and 100,000 to 500,000 cells were analyzed for each bulk sample.

The inactive X chromosome (Xi) expressed Xist, a nuclear untranslated RNA that coats that chromosome. Once an X chromosome is inactivated, the inactive state of the chromosome is clonally inherited through many rounds of cell division. To study the effect of deletion of Xist from Xi, a conditional allele of the gene Xist was introduced onto the chromosome (a "conditional mutant"). After X-inactivation was established, switching off Xist had minimal impact (only a few cells lost their X-inactivation, and only for a short duration because after another week in culture even these cells had spontaneously recovered their X-inactivation). Even with Xist expression continuously switched off for >2 months, allowing the cells to go through many rounds of cell division, the cells' X-inactivation persisted.

Because DNA methylation and hypoacetylation of core histones are believed to contribute to the inactivation of X-linked genes, they also did experiments to test the effects of 5-aza-2'-deoxycytidine (5-azadC) treatment (for DNA demethylation, a well-known use of 5-azadC) or Trichostatin A (TSA) treatment (TSA is a well-known HDACi).

After allowing conditionally mutant cells to go through several rounds of cell division, half of the cultures were treated with TSA (to inhibit histone deacetylase activity and thereby increase histone acetylation). This made no change in the X-inactivation of the cells, even if Xist was turned off.

The separate effect of DNA demethylation was tested in cultures treated with 5-azadC. A small number of cells lost their X-inactivation (19× as many compared to controls). Combining Xist deletion with DNA demethylation increased the number of cells that lost their X-inactivation (30× as many compared to controls).

Combining 5-azadC and TSA treatment (with Xist on) caused a small number of cells to lose their X-inactivation (60× as many compared to controls).

By comparison, a conditional Xist/Dnmt1 double mutant, when it had both mutations turned on, had an increase of 2500× in the number of cells that lost their X-inactivation relative to controls.

Their conclusion was that "Xist RNA, histone deacetylation, and DNA demethylation act synergistically to achieve extraordinary stability of X chromosome silencing". If any of the three mechanisms is left intact, "reactivation rates [were] comparable to mutation rates" [Csankovszki, 2001].

6.5.2 Ectopic Xist Gene Activation is not Stable

Another group has studied the effect of attempting to do X-inactivation in a human male cell line. They developed a transgenetic conditional cell line that allows Xist gene expression to be turned on at will (even though Xist expression would never normally be turned on in a male wild type cell). Turning on Xist produces X-inactivation in this cell line, but not to the same degree as is observed in female cells ("the size of the [inactivation region] was less that is observed for the inactive X chromosome in female somatic cells") [Chow, 2007].

They observed that although some of the epigenetic marks for gene silencing were present (e.g. histone 4 lysine 20 is methylated), and that these marks were Xist dependent. Turning off Xist resulted in gradual re-expression of genes that had been silenced (e.g. EGFP which coded for a green fluorescent protein). After 30 days, the epigenetic marks for this gene had returned to their pre-Xist levels. [Chow, 2007]

It is apparent that although X-inactivation is incredibly stable in cells where it is appropriate (e.g. in female cells), ectopic gene activation (activation where it is not appropriate) is relatively unstable. This is because only appropriate gene expression is supported by a cell phenotype dependent feedback network that resists gene expression that is inconsistent with the differentiation-dependent cell type. Every legitimate type of cell has a feedback network to preserve its phenotype (and to only allow it to adopt another phenotype if it receives the specific signals that induce its differentiation into an appropriate type of daughter cell).

6.5.3 Non-Coding RNAs Mediate Orchestral Regulation of the Cell

6.5.3.1 RNA-Mediated Transcriptional Gene Silencing

RNA interference (RNAi) is a process whereby a small double-stranded interfering RNA (siRNA) molecules functionally target and direct the degradation of a homology containing mRNA (this technique has been known since 1999) [Hamilton, 1999]. It has more recently been discovered that small single stranded non-coding RNAs can bind to DNA in a sequence dependent manner (using part of the length of the ncRNA strand) while recruiting an "epigenetic remodeling" protein complex to that DNA location (using another portion of the ncRNA strand), ultimately resulting in the epigenetic remodeling of the target site to a transcriptionally silent state [Morris, 2011].

Some micro RNAs (miRNAs, a form of small RNA) function to direct transcriptional gene silencing in human cells by causing the methylation of histone 3 lysines 9 and 27, leading to DNA CpG island methylation at the targeted promoter. These targeted epigenetic changes appear specifically at the RNA target site and are not found at distal un-targeted regions, suggesting a level of specificity [Morris, 2009].

"The current mechanistic understanding of [transcriptional gene silencing] is that within the first 24 hours following small RNA treatment there is a robust increase in Argonaute 1 [a protein involved in epigenetic remodeling] at the targeted promoter followed shortly thereafter by increasing concentrations of H3K9 dimethylation and H3K27 trimethylation . . . suggesting that small RNA guides an epigenetic remodeling complex to a particular target loci. When the small RNA targeting is sustained for 3-4 days, DNA methylation [at the CpG island] begins to appear and correlates with the observation of longterm stable gene silencing." [Morris, 2009]

Any gene, in addition to coding for its protein, can have non-coding RNA transcribed when it is activated by a specific promoter, and these ncRNA can silence another gene (or maybe a bunch of genes). And this downstream gene (when activated by a specific promoter) can express its own ncRNAs to silence other genes (or even to activate the original gene, see below). Because a gene can have several associated promoters, and the ncRNAs that it responds to (and the ncRNAs that it produces) can be based upon its epigenetic phenotype, a signaling network is formed that is cell-type specific and can serve to maintain its phenotypic identity.

There are also "pseudo genes" which do not code for any protein, but they have promotor regions that can cause the gene to express various ncRNAs to silence other genes [Weinberg, 2013].

An interesting example of this comes from the pseudogene Tsix (Xist spelled backwards, which turns out to be appropriate), which codes an untranslated RNA that is antisense and complementary for Xist, the RNA that is essential for the X-inactivation of one of the female X chromosomes [Chow, 2005]. When Tsix is expressed, the resulting RNA attaches to any Xist in the area, forming a double stranded RNA, and thereby inactivating the Xist RNA. Because Tsix RNA is formed locally to the active X-chromosome, this prevents the active X-chromosome from somehow becoming inactivated. This illustrates that although epigenetics in the form of CpG island methylation and histone acetylation is what mechanistically turns gene expression on an off for a particular type of cell, it is epigenetics in the form of the RNA expression network that keeps these factors stable whenever necessary for maintaining the differentiated phenotype of the cell.

To elaborate upon the point at hand, because turning on one gene can cause it to produce an ncRNA that targets and degrades a different ncRNA (see "RNA interference" above), it is possible to "silence a silencer", and thereby turn on a downstream gene that would otherwise be silenced.

"In fact, ncRNAs might be actively switching on and off genes in an orchestral regulation that governs the fidelity of the cell and functions in cellular adaptation." [Morris, 2011]

6.6 RTT Treatments that Increase Histone Acetylation Revisited

In the interest of brevity, only the Tubastatin A, Carnitine, Acetyl-L-Carnitine, Fluvastatin, and ω-3 PUFA based treatments will be discussed in detail here. For more information about how each of the other treatments can increase histone acetylation, consult its associated reference listed in Table 2.

Nonetheless, there is a remarkable structural relationship between the molecules associated with many of these treatments. FIG. 1 illustrates how the acetyl group (FIG. 1A) is present in various molecules of interest, either as a group (see the dotted line, which shows where the acetyl group attaches to the rest of the molecule) or as a potential metabolite (e.g. with deletion of the contents shown within the dotted boxes). The deletion of the contents of the dotted boxes shown is physiologically plausible given that the glycerol group gets removed early during the metabolism of triglycerides (forming 3 fatty acids) (FIG. 1H), Beta oxidation removes pairs of carbons within fatty acids (e.g. FIG. 1E, FIG. 1F, FIG. 1G, FIG. 1H), and Alpha oxidation removes the odd carbons within fatty acids (FIG. 1G, FIG. 1H). Enzymes are available for the formation of Acetyl-CoA from acetyl group donors. For example, acetate is readily incorporated into Acetyl-CoA (e.g. by the enzyme acetate thiokinase).

Histone acetyl transferase (HAT) enzymes use Acetyl-CoA as the acetyl group donor when acetylating histone proteins (i.e. forming acetyl lysine (FIG. 1B) at a lysine residue). And histone deacetylase (HDAC) enzymes can remove the acetyl group from a histone's acetyl lysine residue.

6.6.1 Acetylation is Increased by HDACi, Such as Tubastatin a

The level of histone acetylation is in part dependent upon the relative activity of the Histone Acetyl Transferase (HAT) enzymes compared to the activity of the Histone Deacetylase (HDAC) enzymes. The activity of HDAC enzymes can be decreased by HDAC inhibitors (HDACi) such as butyrate or especially by Tubastatin A.

Experiments using radiolabeled acetate (e.g. [I-$^{14}$C]acetate or [methyl-$^3$H]acetate) show that histones can become significantly acetylated within 15 minutes in response to acetate treatment. This may either be due to Acetyl-CoA formed from the radiolabeled acetate being followed by histone acetylation by the HAT enzyme [Boffa, 1978], or by non-enzymatic histone acetylation [Paik, 1970].

Figure 5:
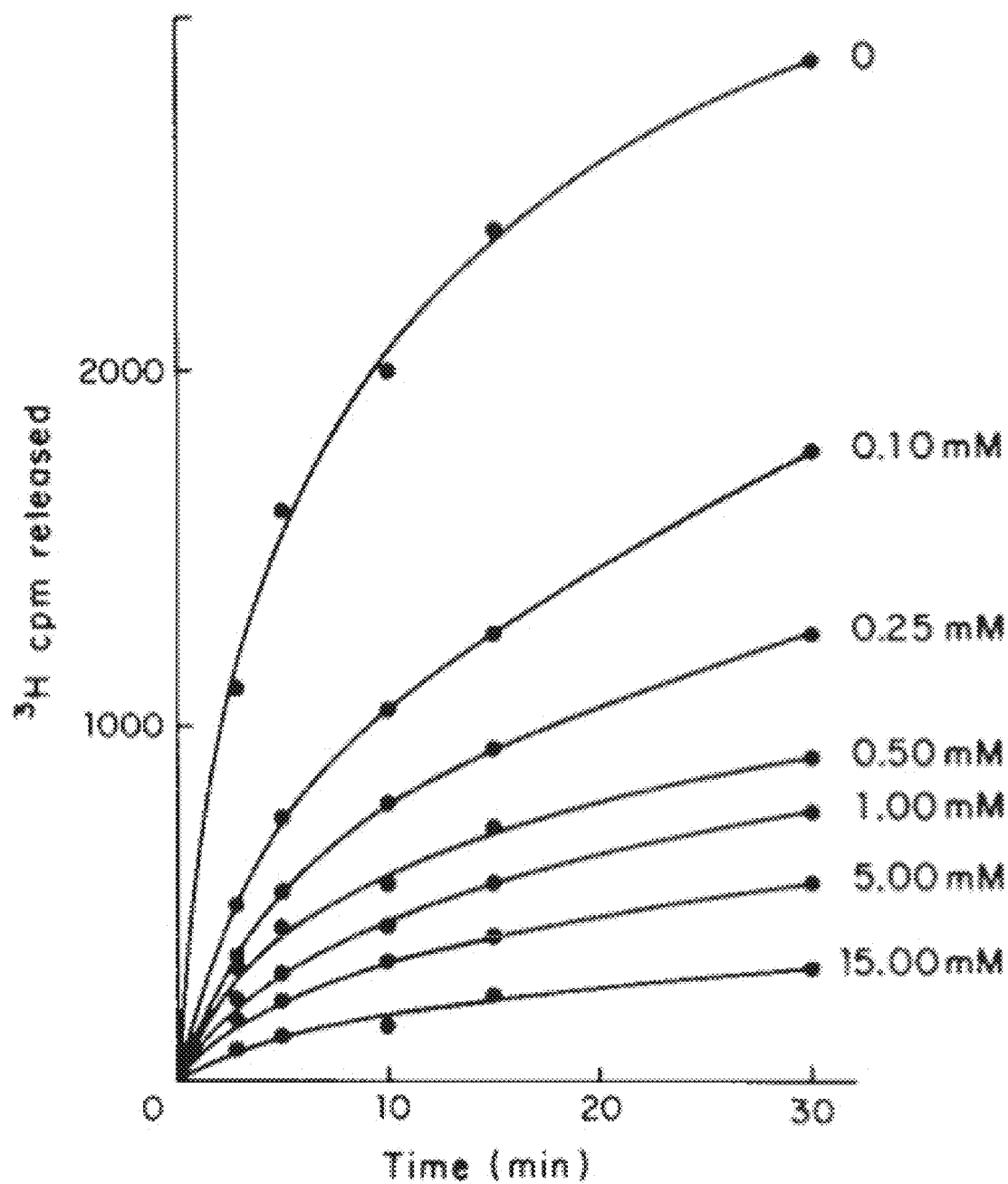
FIG. 5 (from Boffa, 1978) shows the inhibition of histone deacetylase enzyme activity by butyrate treatment.
Figure 6:
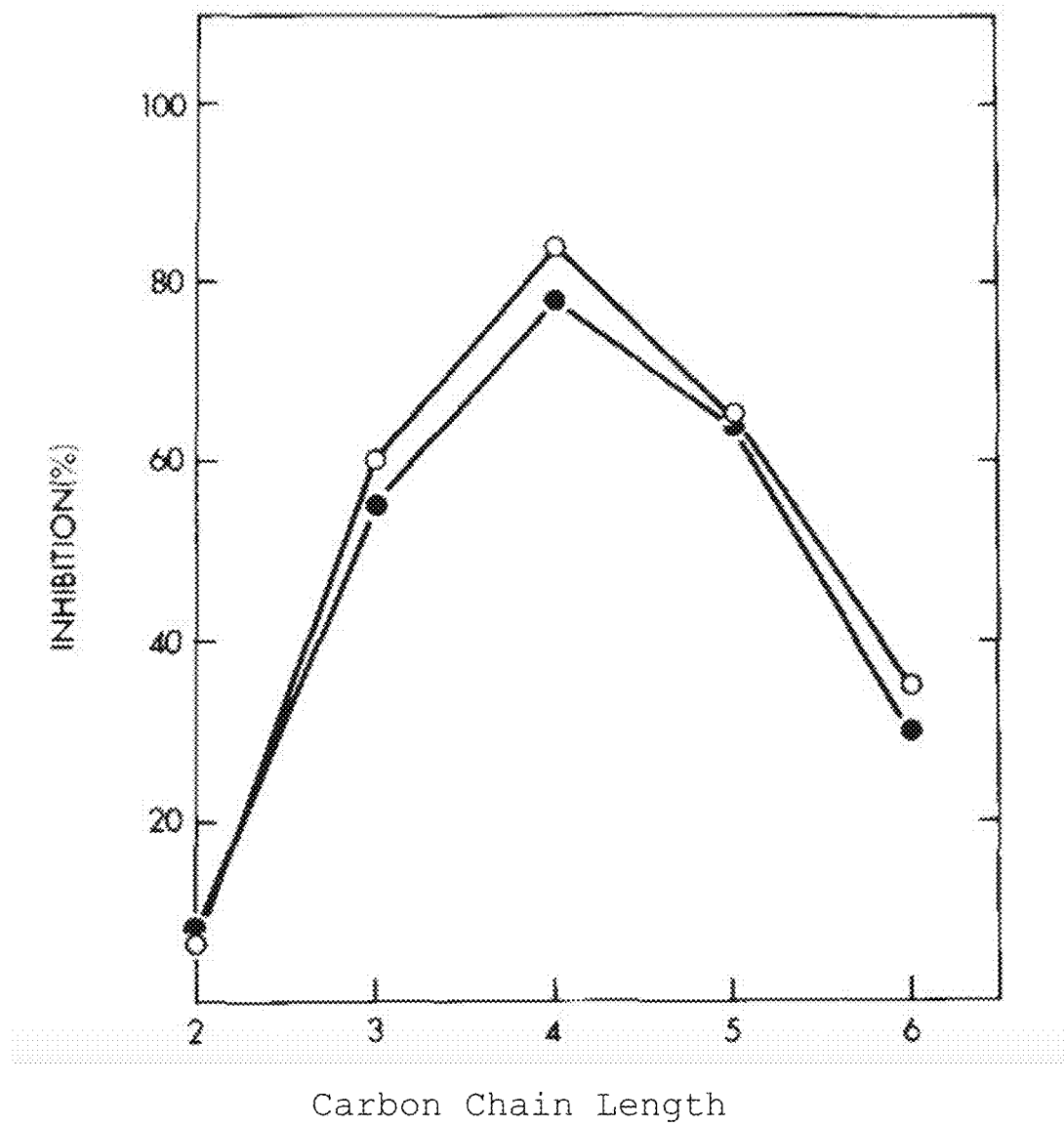
FIG. 6 (from Cousens, 1979) shows the HDACi activity of various short chain fatty acids.
Figure 7:
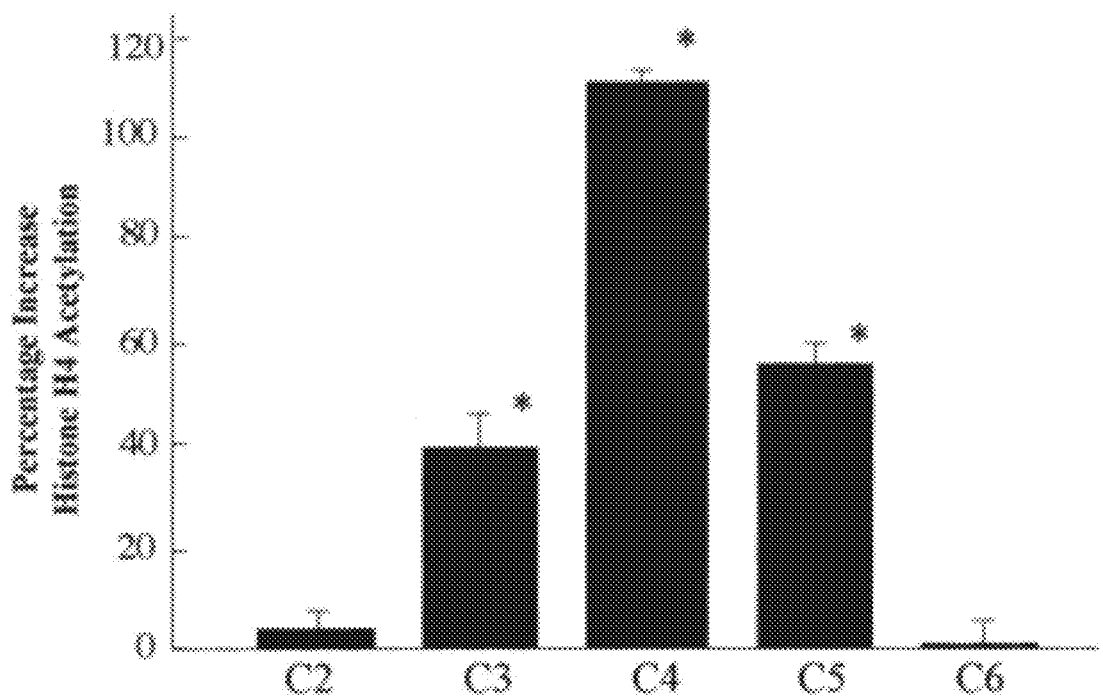
FIG. 7 (from Hinnebusch, 2002) shows the histone hyperacetylation from treatment with various short chain fatty acids.

Further experiments show that in the absence of an HDACi (such as butyrate, 4-carbon long fatty acid), the HDAC enzymes significantly remove the radiolabeled acetyl groups from purified nuclear histones (FIG. 5, from Boffa, 1978). Interestingly, although less active than butyrate, the short chain fatty acids of lengths 3 and 5 also have significant HDACi activity (FIG. 6, from Cousens, 1979), resulting in significantly increased histone acetylation (FIG. 7, from Hinnebusch, 2002). These short chain fatty acids could be products of fatty acid catabolism (or fatty acid synthesis), either by intestinal bacteria or by biological pathways such as β-oxidation or α-oxidation.

"Inhibition of deacetylases by n-butyrate would seem to be a general phenomenon among mammalian cells. . . . The relative lack of specificity for fatty acid chain length . . . coupled with the noncompetitive nature of inhibition . . . suggest that butyrate may be acting as a tight binding detergent in inhibiting these enzymes." [Cousens, 1979]

Figure 8:
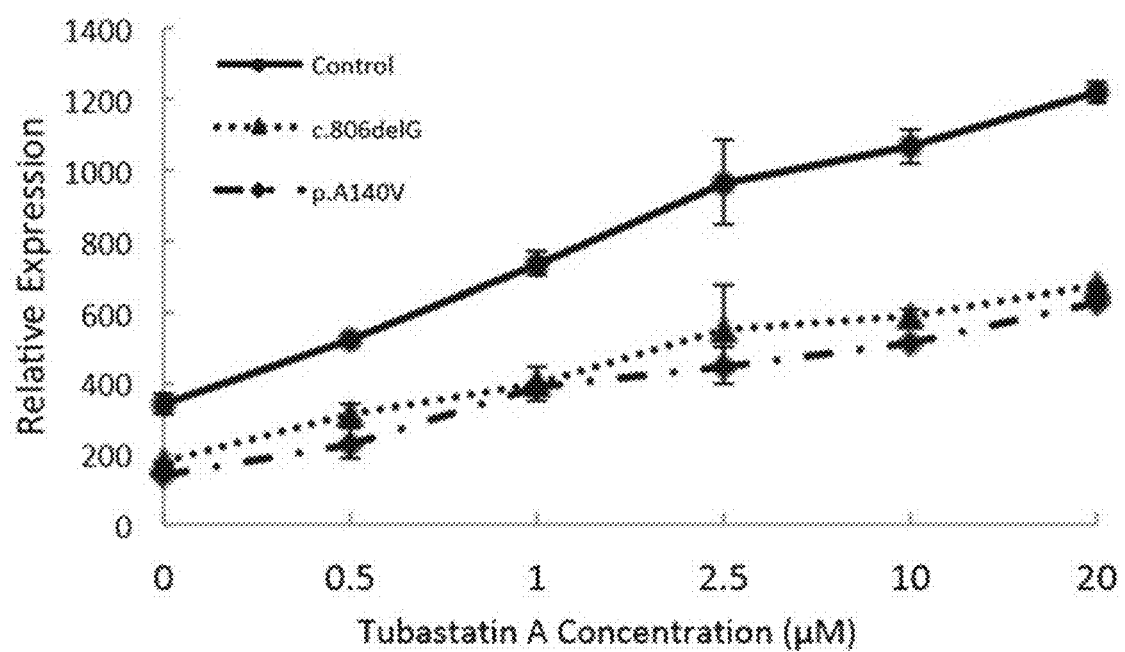
FIG. 8 (from Gold, 2015) shows the high HDACi activity of Tubastatin A.

In contrast to the high concentration of butyrate that is required for butyrate to significantly inhibit histone deacetylation (e.g. 5 mM, FIG. 5), Tubastatin A is a specific HDACi inhibitor in concentrations as low as 1 µM (e.g. 5000 times as active a butyrate) (FIG. 8, from Gold, 2015).

As shown in FIG. 8, treatment of fibroblast cells from RTT patients (c.806delG, p.Ala40Val in the figure) with 1 µM of Tubastatin A increased the expression of acetylated a-tubulin up to that of the normal control patient (Control in the figure, at 0 µM).

6.6.2 Acetyl-L-Carnitine Increases Acetyl-CoA in Neurons

Figure 4:
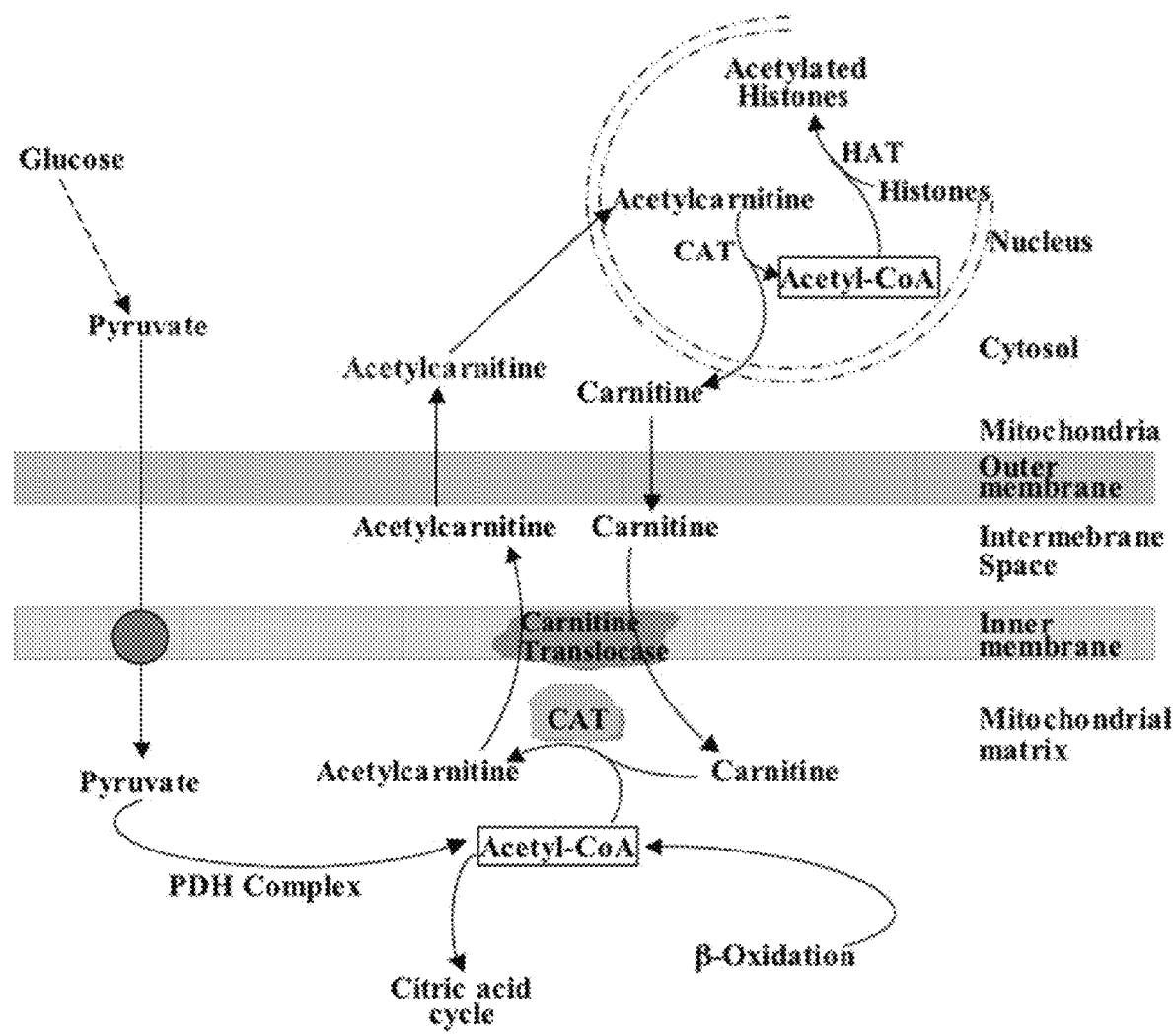
FIG. 4 (from Madiraju, 2009) shows that Acetylcarnitine can enter the cell nucleus and be converted to Acetyl-CoA.

The cell's nucleus needs a source of Acetyl-CoA for enzymatic histone acetylation to be possible. Acetyl-CoA is formed in mitochondria, using either pyruvate (e.g. from glucose metabolism) or as the product of β-Oxidation of fatty acids (FIG. 4, from Madiraju, 2009). Although this Acetyl-CoA cannot leave the mitochondria, it can transfer its acetyl group to a carnitine molecule (thanks to the enzyme Carnitine O-AcetylTransferase "CAT") to form Acetyl-L-Carnitine, which can leave the mitochondria. The nucleus can take up this Acetyl-L-Carnitine and then convert it to Acetyl-CoA using the CAT enzyme (running backwards). The increased Acetyl-CoA in the nucleus results in increased HAT activity and increased histone acetylation (FIG. 1 of Madiraju, 2009). Although they used L-carnitine for their experiments (like treatment #1 in Table 2), forming the Acetyl-L-Carnitine in mitochondria, treatment with Acetyl-L-Carnitine itself (like treatment #11 in Table 2) will have the same net effect.

In humans, there are three enzymes that can produce Acetyl-CoA from acetate. Two of these enzymes are located in the mitochondria, and therefore Carnitine is needed for the Acetyl-CoA to be translocated to the nucleus (where it can be used to acetylate histones). The third enzyme (ACSS2) is located in the cytosol and in the nucleus, and can provide the nucleus with Acetyl-CoA without requiring mitochondrial activity. [Comerford, 2014]

6.6.3 Fluvastatin Increases Acetyl-CoA in Neurons

As shown in FIG. 2, statins (including Fluvastatin and Lovastatin) inhibit the activity of the HMG-CoA synthase enzyme, the rate limiting step in cholesterol biosynthesis. This reduces the flow of Acetyl-CoA into this pathway, thereby increasing the amount of Acetyl-CoA that is available for other purposes, including histone acetylation.

6.6.4 ω-3 Polyunsaturated Fatty Acids Increase HDACi Activity

Although the mechanism is unclear, there is ample evidence that ω-3 polyunsaturated fatty acids work together with HDACi to unsilence ectopically silenced genes. Most of this research has involved colon cancer, and the HDACi is bacterially produced butyrate.

While not wanting to be bound by any particular theory, the applicant notes the following possible mechanism(s) of action:

1. ω-3 polyunsaturated fatty acids are known to affect the expression of hundreds of genes. A comparison of the gene expression profiles between rats fed ω-3 vs. ω-6 PUFAs for 10 weeks found 52 genes whose expression was significantly higher in the ω-3 fed group and 18 genes whose expression was significantly lower [Davidson, 2004]. But what caused the gene expression to change? One answer is that the expression of any one gene depends in part on the expression of other genes. Perhaps the direct effect of the ω-3 treatment is to increase gene expression (e.g. by histone deacetylation) of some genes, explaining how 52 of the genes increased their expression (and gene-to-gene interactions explaining how the other 18 genes decreased their expression). So gene-to-gene interactions can explain why 18 genes went down, but we still need an explanation for why the expression of 52 genes went up.

2. There are various known receptors that are known to be activated by ω-3 PUFAs (e.g. the peroxisome proliferator-activated receptors (PPARs). This is certainly the most obvious explanation, but it may not be the whole story.

Figure 9:
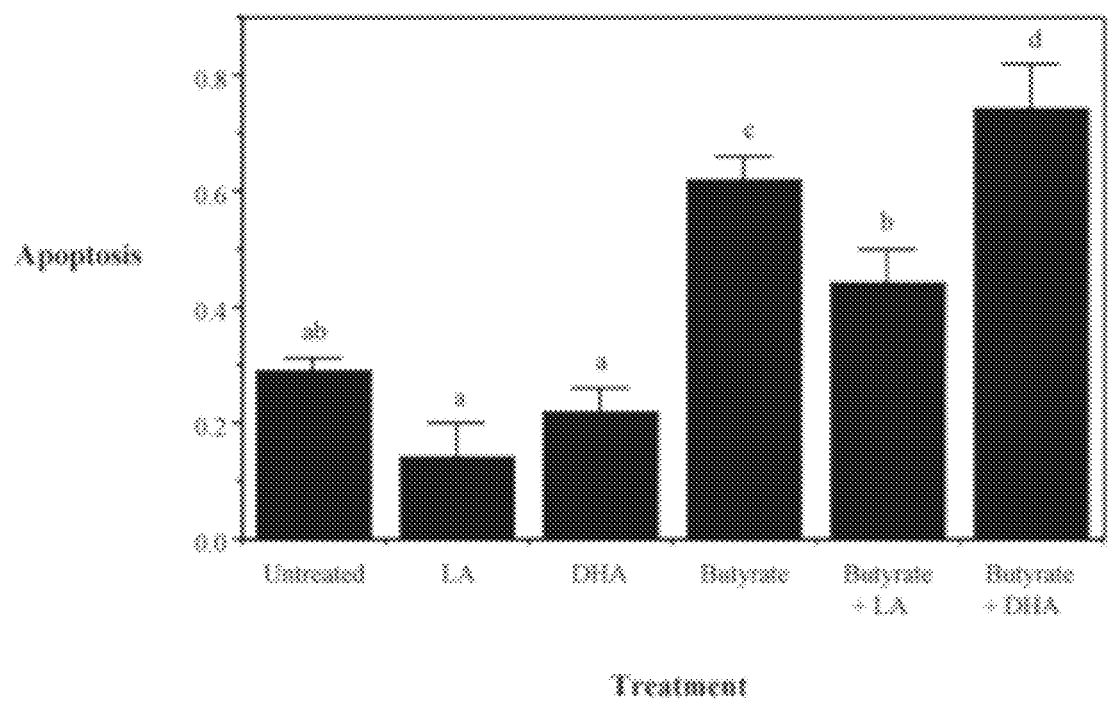
FIG. 9 (from Chapkin, 2008) Synergy between ω-3 and butyrate treatment.
Figure 11:
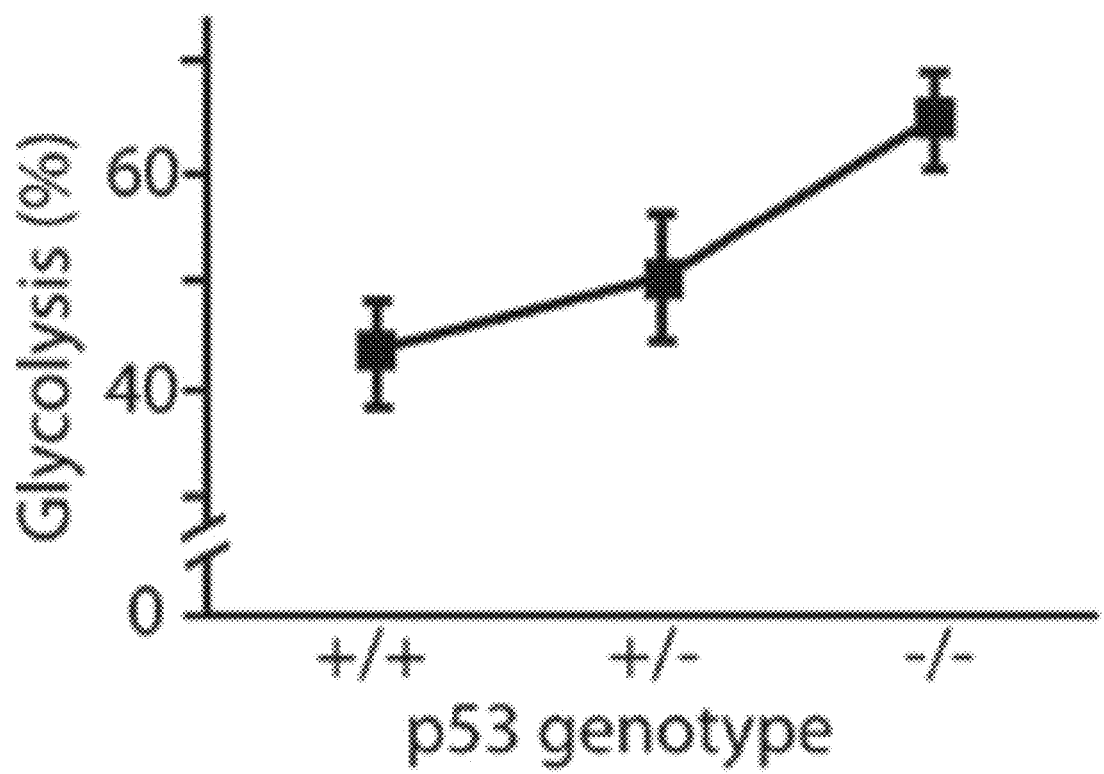
FIG. 11 (from Ma, 2007) shows that p53-null cells use glycolysis for ATP production.

3. Perhaps ω-3 treatment demethylates the promoter region of genes. This could also explain why the expression of 52 genes increased (and 18 decreased from gene-to-gene interactions). It is well established that the combination treatment of an HDACi plus a demethylation agent is more effective than either treatment alone (see the sections on X-inactivation above). The various studies on the effect of ω-3 and butyrate on colon cancer cell apoptosis points commonly describe a synergistic effect. But at least one study shows that their combined effect is roughly additive (and interestingly, if an ω-6 PUFA is used instead of an ω-3 PUFA, the effect is roughly subtractive, perhaps because excess ω-6 depletes ω-3 in tissues) (FIG. 9, from Chapkin, 2008).

4. Given that the figure from Chapkin shows a nearly additive effect, perhaps the ω-3 PUFA treatment produces HDACi activity. This could be due to something as simple as short chain fatty acids being one of the metabolites from PUFA catabolism (e.g. from β-oxidation, or α-oxidation, or from some other metabolic pathway).

Without wanting to be bound by any particular theory, the Applicant thinks that there is a combination of receptor activation (e.g. by PPAR receptors), gene-to-gene expression interactions, and HDACi activity due to short chain fatty acid metabolite(s) that may be formed during the metabolism of ω-3 PUFAs.

In any case, the observed synergy (or at least additivity) between ω-3 PUFA and HDACi treatments for increasing gene expression is sufficient to validate that HDACi treatment is beneficial for RTT, in the presence or absence of ω-3 PUFA treatment.

6.7 Examples of Dietary Compositions for RTT Treatment

Given the variety of beneficial pharmaceutical treatments for RTT shown above to increase histone acetylation, which one is the best for use in humans? Or, perhaps the best treatment isn't one of the above.

Given that it is likely that the treatment will need to be administered for life, ideally it would have a high degree of safety, good effectiveness, and a low degree of side effects.

The ω-3 PUFA treatment has a good potential for this, but the ideal dosage hasn't been determined yet, and there is a practical limit to how much fat should be given to the patient. Also, it isn't clear that ω-3 PUFA treatment is efficient at increasing histone acetylation (given that the mechanism for this hasn't been completely determined).

Acetate is known to be efficient at rapidly increasing histone acetylation (see the experiments listed above) [Boffa, 1978], [Paik, 1970]. Acetic Acid (vinegar, FIG. 1D) forms acetate in water, because the $H^+$ of the OH group separates from the molecule (giving vinegar its acidity).

Vinegar has been used medicinally for a very long time (e.g. in Babylonia in 5,000 BC.), and is still being researched. Surprisingly, no one seems to attribute the medicinal properties of vinegar to its acetate content. They look for something else: the potassium content of apple cider vinegar [Orey, 2006; page 20], the flavonoids of red wine vinegar [Orey, 2006; page 67], or the polyphenols of basalmic vinegar [Orey, 2006; page 101].

A recent study showed that vinegar intake (750 to 1500 mg of acetate per day) for 12 weeks reduces body weight, BMI, and body fat mass in obese Japanese subjects, with a dose-dependent response [Kondo, 2009]. This dosage is in the range recommended for various medicinal uses, which is typically 1 to 2 tablespoons of apple cider vinegar in a glass of water [Orey, 2006; page 141], which equates to 750 to 1500 mg of acetate for the normal 5% "acidity" of vinegar.

But vinegar is not for everyone. For one thing, there is the acid content, which can cause canker sores, heartburn, tooth damage, bladder pain, flare-ups of interstitial cystitis (bladder infection), and joint discomfort [Orey, 2006; pages 211-215]. And some people (most people?) don't like the taste of drinking this much vinegar at once (even when diluted by a full glass of water).

6.7.1 A Dietary Supplement

But for our purposes, it is not the acidity we are after (or the potassium, the flavonoids, or the polyphenols). It is the acetyl groups that come from the acetate. Instead of having the acetate attached to an $H^+$ (which is released when the acetate is dissolved in water), the acetate can be attached to another cation such as sodium, which will release a $Na^+$ when dissolved in water. Acidity no more.

But for our purposes, there is a better cation than sodium (which some people try to avoid). Magnesium is an essential micronutrient which is deficient in the modern (Western) diet, partially due to magnesium depletion of farming soil.

I made some "Magnesium ProAcetyl" capsules by:
1. Start with 250 ml "Heinz Distilled White Vinegar" (5%)
2. While mixing in a Kitchen Aid mixer, add "Freeda Vitamins Inc." supplement grade Magnesium Carbonate powder until the pH=7.0 (7 tablespoons=105 ml=35.7 g)
3. Mix a few minutes longer.
4. Pour the mixture into a non-stick baking tray (with the liquid spread across the area of the tray up to the sides of the tray).
5. Place the tray in an "Excalibur" Food Dryer and set the temperature to 63 degrees C. Run the food dryer overnight.
6. Remove the white, crumbly product from the tray using a wooden spoon.
7. Grind the crumbly product to a powder (use a mortar and pestle) to get 42 g of fine powder.
8. Fill 60 size "00" capsules with the powder (700 mg per capsule, of which ~600 mg is acetate).

The magnesium carbonate dissolves in water (or the water of vinegar) into $Mg^{2+}$ and carbonate ($CO_3^{2-}$). The carbonate reacts with 2 $H^+$ to make 2 $CO_2$ (which bubbles out from the mixture), leaving the $Mg^{2+}$ and 2 acetates to form the salt "magnesium acetate" when it dries.

I took these capsules, 2 a day with breakfast for a month, with no ill effects. Basically, they went down without notice.

6.7.2 Another Dietary Supplement

Because USP grade (suitable for use in food, dietary supplements, and cosmetics) calcium acetate is readily available commercially (e.g. from Spectrum Chemical Mfg. Corp, Gardena Calif., USA), there was no need for me to make my own powder. I put 500 mg each in size "0" "Calcium ProAcetyl" capsule, (~375 mg of acetate per capsule) and took these capsules for over a month, with no ill effects. They also go down without notice at breakfast.

Similar to the magnesium version, the calcium version dissolves into calcium ions and acetate ions in water.

6.7.3 a Nutraceutical Food (To my wife's chagrin) I mixed two capsules worth (1000 mg) of the calcium acetate powder into a serving of Chicken Bouillabaisse that she made as one of our favorite dinners [Kenji Lopez-Alt, 2009] to make "ProAcetyl Fortified Chicken Bouillabaisse". I didn't notice any change in the taste at all.

6.7.4 A Nutraceutical Beverage

I mixed one capsules worth (500 mg) of the calcium acetate powder into an 8 oz glass of "Simply Orange" juice (Simply Orange Juice Company, Apopka, Fla., USA) and kept it overnight in the refrigerator to make "ProAcetyl Fortified Orange Juice". It tasted like normal orange juice.

Other beverages that taste normal after the same mixing and aging process include "Simply Lemonade" juice (from the same manufacturer as the orange juice), "V8 100% Vegetable Juice" (Campbell Soup Company), and Canada Dry Ginger Ale" (Dr. Pepper/Seven Up, Inc.).

6.8 Examples of Use 6.8.1 Treatment of RTT

For treating RTT, it is just necessary to administer the appropriate amount of ProAcetyl compositions (capsules, food or beverages) to achieve the desired dosage amount.

Because many RTT patients cannot swallow capsules, either the nutraceutical food or the nutraceutical beverage (or both) should be used, at the choice of the mother.

6.8.2 Dosages

Based upon the medicinal use of vinegar (for treating various ailments) and for the use of Dichloroacetate for treating cancer (see below), the expectation is that 900 mg of acetate should produce a beneficial response. Of course, it would be appropriate to conduct a Phase I clinical trial to determine both the minimum effective dosage and the maximum tolerable dosage. Because of the very low toxicity of acetate (see below), it is expected that the "therapeutic window" will be very wide.

In the absence of a Phase I clinical trial, the most preferred dosage is 1500 mg of acetate per day. A less preferred dosage is 750 mg to 7500 mg of acetate per day. An even less preferred dosage is 375 mg to 15000 mg of acetate per day.

Because the practice in the art is to conduct a Phase I clinical trial to determine the acceptable dosage range for a pharmaceutical treatment, conducting such a clinical trial (or its equivalent) is not regarded within the art as undo experimentation.

6.9 Treatment with Acetate Prodrugs is Amazingly Nontoxic

Acetate in the form of acetic acid (FIG. 1D), sodium acetate (FIG. 10A), potassium acetate (FIG. 10B), calcium acetate (FIG. 10E), and glycerin triacetate (FIG. 10F) are all FDA approved food additives that are generally recognized as safe. Magnesium acetate is also FDA approved for use as a dietary supplement. All of these compounds readily produce acetate when consumed by mammals. (Note: the dotted lines in the figures show where the acetyl groups connect to the rest of the molecule.)

The most interesting of these (from an oral toxicity standpoint) is glycerin triacetate (also known as triacetin), which has been proposed for use as a major food source for astronauts during long-term space missions (where food needs to be synthesized on the space ship). One of these studies was done by the "Committee On Space Research" and published as "Current Research on Regenerative Systems" [Shapira, 1968]. They conclude that "animals can tolerate up to 20% triacetin" (as a percentage of total diet, replacing conventional carbohydrates).

More extensive toxicity information is provided in the "Final Report on the Safety Assessment of Triacetin" [CIREP, 2003]:

"Triacetin was affirmed as a generally recognized as safe (GRAS) food additive by the Food and Drug Administration (FDA). Triacetin was not toxic to animals in acute oral or dermal exposures . . . Triacetin was quickly metabolized into glycerol and acetic acid and these chemicals were not developmental toxins. . . . Rats were fed for 30 days a diet in which 28.5% of total calories were supplied by Triacetin. No overt signs of toxicity were observed." [CIREP, 2003]

As noted in the report, triacetin was quickly metabolized into glycerol and acetic acid (acetate ions), so the non-toxicity of the acetate from triacetin provides evidence that acetate from any other prodrug for acetate (e.g. any compound that metabolizes to form acetate) is also non-toxic (i.e. not toxic from the acetate that is formed).

6.10 Increased Histone Acetylation is Good for Your Memory Too

There are various medicinal benefits from treatment with acetyl groups (more about this in other sections below), but it is especially interesting that they improve memory and learning even for people who don't have Rett syndrome.

Altered histone acetylation is associated with age-dependent memory impairment in mice. Treatment with the HDACi drug Vorinostat (SAHA) improves memory for 16 month old mice [Peleg, 2010]. For humans, the dietary supplement Juvenon, which contains acetyl-L-carnitine (an acetyl group donor) is used to improve the memory performance of old people. Interestingly, Juvenon attributes the benefits of their supplement to acetyl-L-carnitine improving neurotransmitters, readily entering the nervous system, and increasing mitochondrial energy production. They do not attribute any of the benefits to the acetyl group itself.

It has been reported that histone deacetylase 2 [Penny, 2014], histone deacetylase 3 [Penny, 2014], and histone deacetylase 4 [Sando, 2012] have important roles for the long term potentiation (LTP) that is necessary for learning and memory. All three of these are responsive to treatments with HDACi drugs, with beneficial results from treatment with butyrate, valproic acid, Trichostatin A, and SAHA [Penny, 2014].

In particular, HDAC4-dependent signaling appears to be involved in a path supporting synaptic plasticity and memory that has distinctive features when compared to the activity of MeCP2. According to Sando, 2012 (references omitted):

"Similar to HDAC4, the nuclear function of MeCP2 is affected by the site-specific phosphorylation. None the less, MeCP2 associates with genomic DNA in a histone-like fashion, globally alters chromatin structure, and impacts virtually thousands of genes triggering a genome-wide response of chromatin to changes in neuronal activity. Furthermore, MeCP2 acts as both a transcriptional repressor and activator, and MeCP2 loss-of-function studies revealed a variety of phenotypes, including altered neuronal branching, excitatory synapse numbers, and reduced inhibitory synapse strength. Unlike MeCP2, HDAC4 appears to interact with sites sparsely distributed across the genome and influence a relatively restricted pool of genes."

Without wanting to be restricted to a particular theory, the applicant notes that there are multiple pathways for memory, learning, and un-learning that operate in parallel (and sequentially) in humans, including: (1) short term potentiation, (2) long term potentiation, (3) memory consolidation (e.g. during sleep), (4) memory revision (e.g. from recall, which can modify stored memories), and (5) un-learning (new experiences updating or replacing what had previously been learned). Perhaps with RTT, one of the learning pathway is lost (unfortunately), but an un-learning pathway that turns on at the same stage of development (e.g. for memory consolidation) remains active.

It would make sense for memory consolidation (seeing how a new experience fits in with past experiences and linking them together) to be turned-off in infancy, because there hasn't been enough experience to meaningfully form links. It is known that repeat experiences form the basis for early learning. But once enough has been learned (from repeat experiences) a single new experience can be put into context, either fitting in (and reinforcing) previous learning or contradicting (and therefor favoring unlearning) what has previously been learned. This new stage of development (being able to unlearn, based upon a single new experience) could be the fatal-flaw in the RTT brain.

But for everyone else, the beneficial treatment for RTT (increased histone acetylation) could improve our learning and memory, especially as we age.

6.11 Reversal of the Age Related Decrease in Histone Acetylation

It is known that the general level of histone acetylation decreases with age. It is also known that inflammation is increased when histone acetylation is decreases. It is also known that cancer cells have an abnormally low level of histone acetylation. What hasn't been appreciated in the past is the role of dietary acetyl groups as an essential micronutrient.

The paper "Histone Deacetylase Inhibitors for Treating a Spectrum of Diseases Not Related to Cancer [Dinarello, 2011] lists a variety of diseases and conditions, especially conditions that are caused by chronic inflammation, and this paper in hereby included by reference in its entirety.

6.12 Increased Histone Acetylation Improves Mood and Behavior

"In the rat, the adult offspring of mothers that exhibit increased levels of pup licking/grooming (i.e., High LG mothers) over the first week of life show increased hippocampal [glucocorticoid receptor] expression, enhanced glucocorticoid feedback sensitivity, decreased hypothalamic corticotropin releasing factor expression, and more modest . . . stress responses compared to animals reared by Low LG mothers. . . . These studies support an epigenetic mechanism, since the fostering mother and not the biological genetic mother define the stress response of its adult offspring. . . . A comprehensive analysis of the hippocampal transcriptome of the offspring of High and Low LG mothers revealed differences in a few hundred genes. This suggests a change in epigenetic programming in the brain of the offspring as a consequence of maternal care." [McGowan, 2008]

"This programming by maternal behavior is stable and long lasting, but . . . is reversible by agents that interfere with either the methylation or histone deacetylation machinery. Thus the maternal care model typifies the first principles of epigenetic programming, which are stability and relative plasticity." [McGowan, 2008]

"Trichostatin A induces replication-independent demethylation in cell culture. Trichostatin A induces histone acetylation by inhibiting HDACs and thus tilting the histone acetylation towards acetylation. We proposed that this open chromatin structure induced by the hyperacetylation facilitated the interaction of demethylases with methylated DNA and thus tilted the DNA methylation equilibrium toward demethylation (Cervoni and Szyf, 2001). We therefore addressed the question of whether the epigenetic programming early in life could be modulated during adulthood." [McGowan, 2008].

"Trichostatin A [treatment] of adult offspring of Low LG maternal care increased acetylation, reduced methylation, activated [the glucocorticoid receptor gene] to levels indistinguishable from adult offspring of High LG maternal care and reduced stress response to the levels of offspring of High LG (Weaver et al., 2004)." [McGowan, 2008]

In humans, childhood stress can affect the stress response and behavior of an adult. This is likely to involve epigenetic programming, similar to that which occurs experimentally in rats exposed to early-age stress. And this epigenetically programmed excessive stress response is likely to be reversible by treatments which increase histone acetylation and thereby reduce the methylation of the promoter for the human glucocorticoid receptor.

This is consistent with the observation that various mood stabilizing and antidepressant drugs are HDAC inhibitors, including valproic acid, lithium chloride, lamotrigine, carbamazepine, oxcarbazepine, levetriacetam, olanzapine, clozapine, clomipramine, citalopram, and duloxetine [Ookubo, 2013]. It seems that these drugs share the same mechanism of action (increased histone acetylation, leading to the reversal of ectopic CpG island methylation) that can be achieved with the claimed dietary supplements and nutraceuticals.

Therefore, much of the depression and mood abnormalities in modern society may be the result in part of a dietary deficiency (the lack of dietary acetyl groups) that can be readily corrected by the administration of the claimed dietary supplements and nutraceuticals.

6.13 Elimination of Pre-Cancerous Cells (Cancer Stem Cells)

Cancer is considered to be a multitude of diseases. Even a single type of cancer involves a multitude of mutations, with each individual patient's cancer having a different mix of mutations. And even a single tumor within an individual patient can have cells with different mixes of mutations, with some mutations in common (e.g. the mutations that occurred early in tumorigenesis, and therefore are present in the various strains of daughter cells) and other mutations varying due to different daughter cells acquiring different mutations as the tumor cells continue to divide.

What all cancers have in common is "genomic instability", with both a multitude of mutations within the tumor and the ability to continue to mutate rapidly (e.g. to become resistant to cancer treatment). In some cases, resistance to a cancer treatment can develop without requiring a new mutation, because a sub-population of the tumor cells may already have a resistance to the treatment and now have a selective advantage to favor their proliferation (as the tumor cells that are sensitive to the treatment die off). The development of resistance limits the effectiveness anti-cancer treatments.

Another problem is that most anti-cancer treatments selectively target rapidly dividing cells, killing the cells when they replicate (tumor cells and hair cells alike), but a tumor may also have cancer stem cells that replicate slowly, giving them the ability to survive (perhaps for years) until the cancer develops again.

6.13.1 Non-Hodgkin's Lymphoma Reversal with Dichloroacetate

"After being successfully treated with six treatments of Rituxan plus CHOP (cyclophosphamide, doxorubicin hydrochloride, vincristine, and prednisolone) regime over a period of three months in 2007, a positron emission tomography (PET) scan showed a complete remission of the Non-Hodgkin's Lymphoma. With no further treatments by August 2008, the PET showed his tumors returned in the nasopharynx and neck lymph glands which presented with a low grade fever of 99.8, sweating and fatigue." [Flavin, 2010]

"The Non-Hodgkin's Lymphoma patient refused conventional therapy, instead personally obtaining dichloroacetate (DCA) he began administering 900 mg daily at 10 mg/kg in August 2008, adding a daily 750 mg of thiamine to protect his nerves from toxicity. Four months later a PET scan showed complete remission (see FIG. 2 [of the original article]). He has remained tumor-free on the continued regime of DCA and thiamine since his last PET in May 2009. Monthly blood tests are showing that all of his parameters are normal." [Flavin, 2010]

Dichloroacetate has been used in medicine for over 30 years as an investigational drug to treat severe metabolic disorders as well as the treatment of congenital lactic acidosis in children. As a medicinal, DCA is generally well tolerated from dosages between 10 mg/kg and 50 mg/kg, although prolonged exposure is associated with peripheral neuropathy. Its activation of the pyruvate dehydrogenase enzyme of the mitochondria (due to its inhibition of pyruvate dehydrogenase kinase) decreases glycolysis and reactivated glucose oxidation, a favorable approach to ameliorate lactic acidosis [Flavin, 2010].

6.13.2 Dichloroacetate Treatment is Beneficial for Many Cancers

The use of dichloroacetate for the treatment of cancer was first disclosed in 2007, well before the patent was granted in 2013 [Michelakis, 2013]. But due to enthusiastic early and ongoing reports posted on the internet, patients have been self-treating their cancers for years (such as reported in the Case Report above [Falvin, 2009]).

This has encouraged various researchers to investigate the effect of DCA on the viability of various types of tumors (either in humans, in animal models, or using tumor cells in vitro): (1) non-small lung cancer [Bonnet, 2007]; (2) glioblastoma [Bonnet, 2007; Michelakis, 2010; Shen, 2015]; (3) breast cancer [Bonnet, 2007; Sun, 2009; Haugrud, 2014; Gang, 2014]; Hong, 2015]; (4) colorectal cancer [Cairns, 2007; Madhok, 2010; Lin, 2014; Delaney, 2014; Ho, 2015]; (5) neuroblastoma [Vella, 2011; Hanberry, 2014]; (6) T cell lymphoma [Kumar, 2012]; (7) C6 glioma [Duan, 2013]; (8) prostate cancer [Kailavasan, 2013]; (9) Dalton's lymphoma [Kumar, 2013; Kumar, 2015]; (10) pancreatic cancer [Cairns, 2007; Haugrud, 2014]; (11) melanoma [Abildgaard, 2014]; (12) B-chronic lymphoctic leukemia [Agnoletto, 2014]; (13) recurrent brain tumors [Dunbar, 2014]; (14) medulloblastoma [Di Mango, 2014]; (15) head and neck squamous cell carcinoma [Cernigia, 2015]; and (16) lung adenocarcinoma [Zhou, 2015].

Given that cancer is not a single disease, it may be surprising that dichloroacetate treatment has been found to be beneficial for so many types of cancers. But all types of cancers have something in common. If we could target genomic instability itself, turning the cancer's multiple mutations against it, we would have a broadly applicable method for combating cancer. Could dichloroacetate treatment be doing this? And if so, how?

In the interest of brevity, I will focus on the first published use of DCA to inhibit cancer growth [Bonnet, 2007], the patent that resulted from this work [Michelakis, 2013]. This work is representative of the studies that followed, and sets the context for how these studies were constructed and how their results were interpreted (so little is lost by not spending words on them). Then I will discuss the surprising results from a study which extends this work by showing that DCA also induces apoptosis in tumor stem cells. [Michelakis, 2010]

6.13.3 DCA Effectively Treats Various Tumor Cell Lines and Rats

"Although mitochondria are recognized as regulators of apoptosis [programmed cell death], their importance as targets for cancer therapy has not been adequately explored or clinically exploited. In 1930, Warburg suggested that mitochondrial dysfunction in cancer cells results in a characteristic phenotype, that is, aerobic glycolysis. Positron emission tomography (PET) has now confirmed that most malignant tumors have increased glucose uptake and metabolism. . . . This suggests that the metabolic phenotype in cancer is due to a potentially plastic mitochondrial remodeling that results in suppressed oxidative phosphorylation, enhanced glycolysis, and suppressed apoptosis." [Bonnet, 2007]

"Whether the metabolism of glucose will end with glycolysis in the cytoplasm (converting pyruvate to lactate) or continue with glucose oxidation in the mitochondria is controlled by a gate-keeping mitochondrial enzyme, pyruvate dehydrogenase (PDH). . . . PDH is inhibited by phosphorylation by PDH kinase (PDK). . . . In preliminary experiments, we compared several cancer with normal cell lines and found that cancer cells had more hyperpolarized mitochondria and were relatively deficient in Kv channels. If this metabolic-electrical remodeling is an adaptive response, then its reversal might increase apoptosis and inhibit cancer growth. We used dichloroacetate (DCA), a small, orally available small molecule and a well-known inhibitor of PDK." [Bonnet, 2007]

In summary, they use DCA to inhibit PDK, which prevents it from phosphorylizing PDH, causing the tumor cell to switch its energy metabolism from glycolysis in the cytoplasm (characteristic of tumor cells) to glucose oxidation in the mitochondria (characteristic of non-tumor cells). By shifting the location of this energy metabolism to the mitochondria, and thereby decreasing mitochondrial membrane hyperpolarization, they think that apoptosis becomes enabled, leading to the death of the tumor cells. Their experiments with "three human cancer cell lines: A549 (non-small-cell lung cancer), MO59K (glioblastoma), and MCF-7 (breast cancer)" and also with rats implanted subcutaneously with A549 tumor cells, appear to support their theory of action for DCA mediated tumor cell apoptosis.

The majority of the data presented in the patent appears to have come from this set of experiments with A549, MO59K and MCF-7 tumor cells, and A549 injected rats. But FIGS. 6 and 7 of the patent are new and interesting. FIG. 6 of the patent clearly shows their model, with DCA entering the mitochondria, and the mitochondria releasing "apoptosis inducing factor" (AIF) which enters the nucleus and also releasing Cytochrome C, which activates Caspases, thus triggering apoptosis.

FIG. 7 of the patent supports their conclusion that "DCA's effects are restricted to mitochondrial pathways." [Michelakis, 2013]

"In order to confirm that the effects of DCA are not nonspecific but are indeed metabolic and regulate apoptosis pathways, a gene chip and GO analysis of treated and non-treated cells were performed. We used a "subtraction" strategy to reveal relevant changes in tumor gene expression that were solely due to DCA. Studying both the A549 and glioblastoma cell lines (i.e. a very different tumor than the lung cancer, epithelial versus glial cells) and focusing on the changes that occurred in a similar pattern on response to DCA therapy revealed changes in gene expression due to DCA, rather than idiosyncratic tumor-specific gene changes." [Michelakis, 2013]

"The genes that were modified by DCA in parallel in A549 (lung) and M059K (glioblastoma) are listed and their expression levels were plotted in a heat map (FIG. 7. . . . Most of these genes were related to mitochondria and complex I . . . This gene chip analysis further supports the model described in FIG. 6." [Michelakis, 2013]

What is interesting is that although the model for DCA's mechanism of action taught by [Bonnet, 2007] and [Michelakis, 2013] as illustrated in FIG. 6 of the patent is well accepted (and repeated in their papers) by the various studies of DCA listed above, none of the authors have considered the implications (or even the cause) of the gene expression changes that are induced by DCA treatment of tumor cells (as shown in FIG. 7 of the patent).

6.13.4 DCA Preferentially Kills Cancer Stem Cells

"When GBM-SCs [glioblastoma multiforme stem cells] were allowed to differentiate into secondary GBM [glioblastoma multiforme] cell lines, the proportion of cells with GBM-SC markers decreased to a value similar to that of the primary cell lines (~10%). When allowed to differentiate in the presence of DCA (0.5 mM), however, the proportion of cells with GBM-SC markers was decreased even further to ~5%. Indeed, DCA induced apoptosis in GBM-SC in vitro as well as in GBM primary cell lines. Apoptosis was further increased in GBM-SCs by the combination of DCA plus TMZ [temolozolomide], providing a rationale for combination therapy. GBM-SC apoptosis took place in vivo in the post-DCA treatment tumors. [Michelakis, 2010]

"Our patients had primary GBMs and the mitochondrial remodeling was at least partially reversible with DCA, suggesting that is was not due to irreversible dysfunction. Furthermore, we show that putative GBM-SC may undergo the same metabolic and mitochondrial remodeling, but to an enhanced degree, because GBM-SC had the most hyperpolarized mitochondria both in vivo and in vitro. Reversal of this mitochondrial remodeling by DCA induced apoptosis in GBM-SC both in vitro and in vivo. Although the magnitude of apoptosis induction by DCA is not high (compared to cytotoxic agents), it is relatively selective, sparing noncancer cells, and because it involves GBM-SC, may result in a more sustained clinical effect." [Michelakis, 2010]

6.13.5 Rethinking the Warburg Effect

The above presented (and commonly accepted) model for the method of action of DCA is that by increasing PDH activity (due to PDK inhibition), the Warburg Effect is reversed, allowing the mitochondria to induce apoptosis. But other research shows that it is the tumor suppressor protein TP53 (Tumor Protein p53, coded by the p53 gene) that regulates mitochondrial respiration [Matoba, 2006; Ma, 2007] and that the restoration of TP53 function leads to the reversal of the Warburg effect and tumor regression [Ventura, 2007].

The expression of wild type p53 directly causes the expression of the SCO2 gene, producing mRNA for the SCO2 protein (Synthesis of Cytochrome c Oxidase 2) [Matoba, 2006]. The SCO2 protein is critical for regulating the cytochrome c oxidase (COX) complex, the major site of oxygen utilization in the eukaryotic cell. Disruption of the SCO2 gene in human cancer cells causes the metabolic switch toward glycolysis that is exhibited by TP53-deficient cells [Ma, 2007].

Functional p53 is also needed for the expression of the TIGAR gene (TP53-induced Glycolysis and Apoptosis Regulator) gene [Bensaad, 2006]. TIGAR decreases glycolysis by dephosphorylating fructose-2,6-biphosphate (Fru-$2,6$-$P_2$), an important allosteric effector (+) of the key glycolytic enzyme 6-phosphofructose-1-kinase (PFK-1) [Ma, 2007].

While TP53 is representative of the various tumor suppressor genes that are frequently mutated or suppressed in tumor cells, it provides us with an undeniable indicator of how prevalent the inactivation of these genes is in human cancers. If the Warburg effect is a "general property" of cancers, and it is specifically caused by TP53 inactivation, then these cancers must all have inactivated TP53.

6.13.6 Cancer Initiation, Progression, and Propagation

The development of cancer (i.e. carcinogenesis) has been shown to involve three stages: (1) initiation (a process in which normal cells are changed so that they are able to form tumors); (2) promotion (a process in which existing tumors are stimulated to further grow and change); and (3) progression (more rapid growth and invasiveness).

A classic animal model of this process involves treating a mouse with Diethylnitrosoamine (DEN) and then later on chronically feeding the mouse with Phenobarbital (PB) in the diet. Without the prior initiation with DEN, feeding PB is not carcinogenic [Kolaja, 1996]. Furthermore, repeated treatments with DEN do not produce a tumor (once is enough, but not sufficient without a promotor). Clearly, the initiator and the promotor have different roles in carcinogenesis.

The sequential process of carcinogenesis was studied in detail using a well-established model system of mouse carcinogenesis, the multistage skin tumor progression model [Fraga, 2004].

"In this model, beginning with normal mouse skin, sequential topical application of various mutagens, such as [ . . . ], and tumor promoting agents, such as [ . . . ], generate a spectrum of different stages of tumorigenesis ranging from premalignant papilloma to highly metastatic tumors with well-defined genetic lesions in H-ras or p53. We have examined the aberrant DNA methylation profile (by candidate gene as well as genomic DNA and RNA approaches) of all stages of mouse skin tumor progression, including normal mouse skin; nontumorigenic and tumorigenic keratinocytes . . . ; benign papilloma cells . . . ; tumorigenic squamous carcinoma cells representative of different degrees of differentiation, invasion, and metastasis . . . ; and highly anaplastic spindle carcinoma lines displaying metastatic behavior. Aberrantly methylated genes identified by the mouse study were confirmed in human neoplasms to evaluate the potential of this system to find clinically relevant genes with methylation-associated inactivation and also its ability to serve as a tool to improve understanding of the timing and hierarchy of epigenetic lesions in human cancer." [Fraga, 2004]

They tracked the methylation patterns of the CpG islands for 6 genes known to be hypermethylated in various human cancers. These genes were BRCA1, MLH1, MGMT, E-cadherin, Snail, and MLT1. They found that the first treatment ("initiation", using DMBA, a well-known tumor initiator) caused the MGMT, Snail, and MLT1 gene promoters to become hypermethylated, and that these genes were silenced. There was no change in the methylation status of the genes during the next 5 stages of tumor progression (sequentially treating the cells with various agents known to cause sequential tumor progression in this mouse model). But the methylation status changed when the cell phenotype transitioned from epithelial to spindle cell (i.e. spindle cell carcinoma had developed). The E-cadherin CpG island became hypermethylated and the Snail CpG island lost its hypermethylation.

These results clearly show that treatment with the "initiator" causes gene silencing (by CpG island hypermethylation), but the subsequent treatments (with "promoting" agents), do not tend to alter the methylation status (but they are probably causing DNA mutations, which weren't the subject of this study).

Note that when a gene has been silenced, there is no longer a selective advantage for it to mutate, but for genes that have not been silenced, mutation can provide a selective advantage during tumorigenesis. After tumor suppressor genes have been silenced, various cells within the tumor will have various mutations from each promoter treatment, and the cells with mutations that provide a growth or survival advantage will become the predominant types of cells in the tumor. An advanced tumor will have a variety of mutated genes, and a set of tumor suppressor genes that were silenced early on (and are probably not mutated).

Tumor suppressor genes (such as p53, the gene for TP53) are involved in detecting DNA damage, correcting the DNA damage, and preventing replication of the cell if the DNA damage can't be corrected. TP53 is involved with cell cycle control, receiving signals from proteins that detect various forms of DNA damage, inducing the genes for proteins that do DNA repair, pausing the cell cycle to wait for the DNA to be repaired, and killing the cell (by initiating apoptosis) if the DNA isn't repaired in time.

"The most common cancer-related change known at the gene level is p53 mutation. . . . The three most notable features of the p53 mutation spectra in human cancers are as follows: (i) transitions at CpG nucleotides [i.e. gene silencing by CpG island methylation] contribute heavily to the mutation frequency in many cancers; (ii) a mutation at codon 249 predominates in HCCs [hepatocellular carcinomas] in individuals from high-incidence regions [specifically Qidong, China]; and there is a high frequency of G to T transitions in lung cancer." [Hollstein, 1991]

Interestingly, although p53 is the most commonly mutated gene, the most common "mutation" of p53 is its epigenetic silencing (e.g. CpG island methylation). p53 can also be inactivated by a signaling pathway (see below). The high prevalence of p53 inactivation in cancer explains the Warburg effect, and it also provides a therapeutic target.

Figure 12:
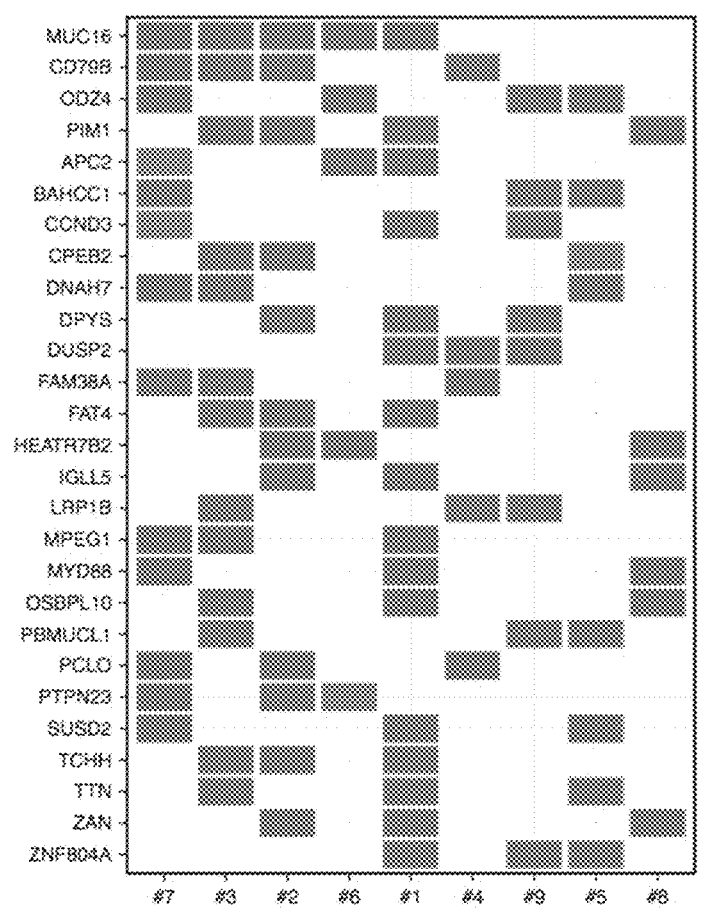
FIG. 12 (from eater, 2015) shows genes affected by mutation in PCNSL.
Figure 13:
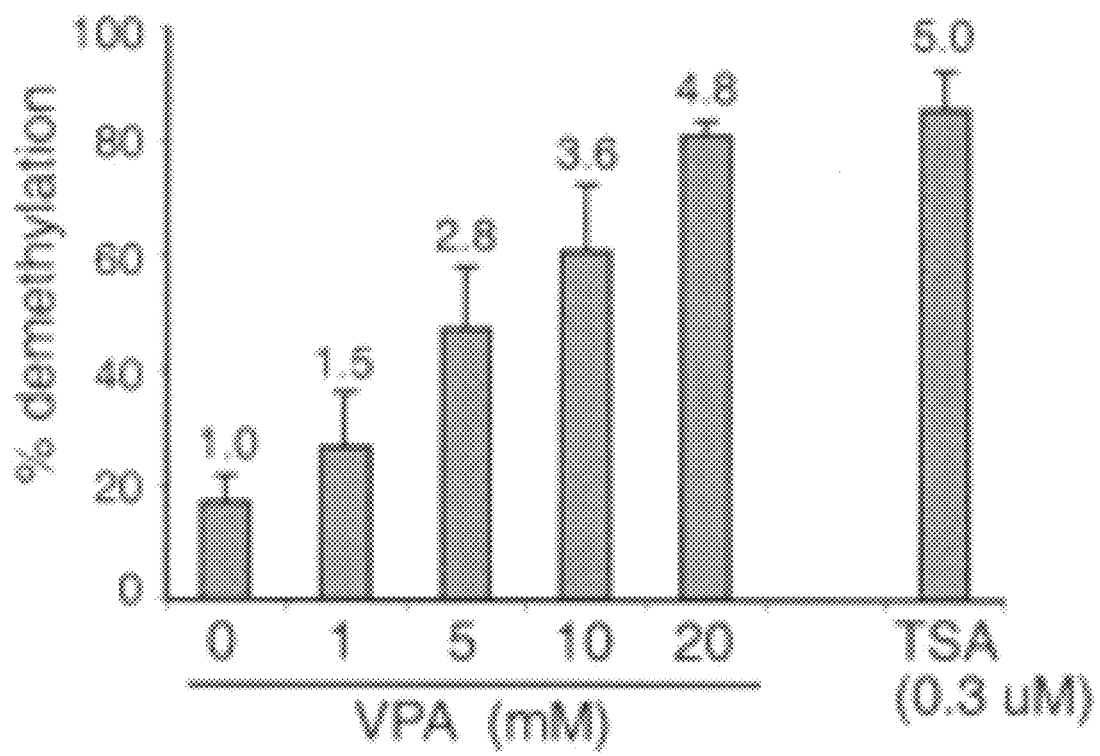
FIG. 13 (from Detich, 2003) shows that valproic acid demethylates CpG sites.

The gene mutations associated with Non-Hodgkin's Lymphoma in the brain (also known as Primary Central Nervous System Lymphoma, PCNSL) has been studied by at least two groups. Whole Exome Sequencing was performed for 9 patients, with 27 genetic mutations showing up in 3 or more patients (FIG. 12) [Vater, 2015]. Interestingly, p53 is not on the list.

Similarly, while the other group found 39 genes that were mutated in two or more of 9 PCNSL patients, p53 is not on the list (see table below). [Bruno, 2015]

Interestingly, DLBCL (and PCNSL) is divided into two subtypes with different prognoses and treatment strategies [Visco, 2012]. Each of these types inhibits p53 expression, each by a different pathway.

One type of DLBCL (named "germinal center" or GCB-DLBCL) is characterized by the expression of CD10 and of BCL-6. Germinal center B-cell lymphocytes are "immature" (i.e. only partially differentiated). B-cell lymphocytes are part of the adaptive immune system, with each B-cell being able to produce a large quantity of a specific antibody (originally produced from randomly rearranging endogenous Ig genes [Cattoretti, 2005]), that successfully targets

| Genes | Chromosome | Mutations | Patients | Functional prediction impact (FISM) | | | | | | |
|---|---|---|---|---|---|---|---|---|---|---|
| | | | | NA | ≥0.5 | ≥0.6 | ≥0.7 | ≥0.8 | ≥0.9 | =1 |
| PIM1 | 6 | 32 | 8 | 0 | 8 | 8 | 7 | 6 | 6 | 5 |
| IGLL5 | 22 | 12 | 6 | 6 | 0 | 0 | 0 | 0 | 0 | 0 |
| MYD88 | 3 | 2 | 5 | 5 | 0 | 0 | 0 | 0 | 0 | 0 |
| TBL1XR1 | 3 | 4 | 4 | 0 | 4 | 4 | 4 | 4 | 4 | 3 |
| CSMD3 | 8 | 4 | 4 | 0 | 4 | 4 | 4 | 3 | 3 | 1 |
| CD79B | 17 | 3 | 3 | 0 | 2 | 2 | 2 | 2 | 2 | 1 |
| HIST1H2AC | 6 | 8 | 3 | 0 | 3 | 3 | 3 | 3 | 1 | 1 |
| ETV6 | 12 | 5 | 3 | 0 | 3 | 3 | 2 | 2 | 1 | 1 |
| KLHL14 | 18 | 7 | 2 | 0 | 2 | 2 | 2 | 2 | 2 | 2 |
| IRF4 | 6 | 3 | 2 | 0 | 2 | 2 | 2 | 2 | 2 | 2 |
| PRKCD | 3 | 2 | 2 | 0 | 2 | 2 | 2 | 2 | 2 | 2 |
| ABCC8 | 11 | 2 | 2 | 0 | 2 | 2 | 2 | 2 | 2 | 1 |
| ZFHX4 | 8 | 2 | 2 | 0 | 2 | 2 | 2 | 2 | 2 | 1 |
| SALL3 | 18 | 2 | 2 | 0 | 2 | 2 | 2 | 1 | 1 | 1 |
| IRF2BP2 | 1 | 3 | 2 | 0 | 2 | 2 | 1 | 1 | 1 | 1 |
| CD37 | 19 | 2 | 2 | 0 | 2 | 2 | 1 | 1 | 1 | 1 |
| OSBPL10 | 3 | 7 | 2 | 0 | 2 | 2 | 2 | 2 | 2 | 0 |
| EBF1 | 5 | 3 | 2 | 0 | 2 | 2 | 2 | 2 | 2 | 0 |
| DST | 6 | 2 | 2 | 0 | 2 | 2 | 2 | 2 | 1 | 0 |
| MIF4GD | 17 | 2 | 2 | 0 | 2 | 2 | 2 | 2 | 1 | 0 |
| HIST1H1D | 6 | 3 | 2 | 0 | 2 | 2 | 2 | 1 | 1 | 0 |
| BTG1 | 12 | 2 | 2 | 0 | 2 | 2 | 2 | 1 | 1 | 0 |
| MEP1B | 18 | 2 | 2 | 0 | 2 | 2 | 2 | 1 | 1 | 0 |
| THBS4 | 5 | 2 | 2 | 0 | 2 | 2 | 2 | 1 | 1 | 0 |
| ADAMTS5 | 21 | 2 | 2 | 0 | 2 | 2 | 1 | 1 | 1 | 0 |
| HIST1H1E | 6 | 2 | 2 | 0 | 2 | 1 | 1 | 1 | 1 | 0 |
| MPEG1 | 11 | 3 | 2 | 1 | 1 | 1 | 1 | 1 | 1 | 0 |
| OBSCN | 1 | 2 | 2 | 0 | 2 | 2 | 2 | 2 | 0 | 0 |
| C10orf71 | 10 | 2 | 2 | 0 | 2 | 2 | 2 | 1 | 0 | 0 |
| HMCN1 | 1 | 2 | 2 | 0 | 2 | 2 | 2 | 1 | 0 | 0 |
| MYH4 | 17 | 2 | 2 | 0 | 2 | 2 | 1 | 1 | 0 | 0 |
| TBC1D4 | 13 | 2 | 2 | 0 | 2 | 1 | 1 | 1 | 0 | 0 |
| SLC2A12 | 6 | 2 | 2 | 0 | 2 | 2 | 1 | 0 | 0 | 0 |
| ETS1 | 11 | 2 | 2 | 0 | 2 | 2 | 0 | 0 | 0 | 0 |
| MUC16 | 19 | 2 | 2 | 2 | 0 | 0 | 0 | 0 | 0 | 0 |
| UNC80 | 2 | 2 | 2 | 2 | 0 | 0 | 0 | 0 | 0 | 0 |
| ACTG1 | 17 | 1 | 2 | 2 | 0 | 0 | 0 | 0 | 0 | 0 |

Clearly, all of these patients had multiple DNA mutations across a wide variety of genes (indicative of genetic instability), but no p53 mutation. If their TP53 protein was operative, the cells with multiple DNA mutations would all have undergone apoptosis long ago. It appears that their p53 gene has been silenced (or inactivated by a signaling pathway).

A larger exome sequencing study of 94 tumor samples from patients with Diffuse Large B-cell Lymphoma (DLBCL, similar to PCNSL but not located in the brain) found a total of 322 mutated "cancer genes", with p53 mutations in 13 of the patients [13.8%, Supplemental spreadsheet #3 of Zhang, 2013]. This shows that the vast majority of patients did not have p53 mutations (but their p53 was probably silenced or inactivated by a signaling pathway).

a specific pathogen. In order to produce the specific antibody, the B-cell modifies its own DNA, first by scrambling the codes for "V fragments", "J fragments" and "D fragments" that are in every B-cell's DNA, and then cutting and splicing its DNA to write the scrambled pattern into the coding region of a gene that it will express in order to product that specific antibody [Clark, 2008]. Because the B-cell (at this stage of development) will be cutting and splicing its own DNA, it turns off the tumor suppressor genes that detect cut DNA. Normally, when the cutting and splicing is completed, the tumor suppressor genes would be enabled again. But the key point is that, for this cell type, it is normal for these tumor suppressor genes to be turned off (at least for a while). In other words, this is consistent with the maturation process for a B-cell lymphocyte, and therefore is not suppressed (e.g. by the cell-type specific pattern of ncRNA expression which maintains the stability of the cellular phenotype).

In effect, the "BCL-6" positive version of DLBCL has a less-differentiated phenotype (which is legitimate for its cell-type) that turns-off p53 (and allows DNA mutations to proceed, without inducing apoptosis).

The other type of PCNSL is called "post-germinal center B cells" (post-GBC, also called "Activated B Cell-like" or ABC-DLBCL). This type of cell is more differentiated and doesn't allow the BCL-6 gene to be expressed. But it does allow NF-κB (nuclear factor kappa-light-chain-enhancer of activated B cells) to be expressed, which has its own pathway for inhibiting p53. NF-κB expression is the cell's "join the army" switch, turning on various aggressive pathways (e.g. generating reactive molecules such as nitric oxide, superoxide, hydrogen peroxide, peroxynitrite, . . . ) to fight nearby pathogens. In order to avoid death by friendly fire, NF-κB protein also inhibits p53 (preferring the chance of dying by necrosis to the almost sure possibility of self-damage).

In post-GBC lymphoma, the NF-κB protein is functional (e.g. its gene is not mutated) and its gene expression is dysregulated, for example by a mutation in the gene for a different protein which, through a signaling pathway, turns on the expression of the NF-κB gene. The involvement of other mutated proteins in NF-κB gene activation was investigated by Compagno, 2009:

"To investigate whether constitutive NF-κB activation in ABC-DLBCL represents a primary pathogenic event or reflects the intrinsic program of the tumor cell of origin, we screened for mutations the complete coding sequences of 31 NF-κB pathway genes in 14 samples. . . . This strategy identified a total of 48 sequence changes distributed in 6 different genes, including the NF-κB regulator TNFAIP/A20 and the positive regulators CARD11, TNGRSF11A/RANK, TRAF2, TRAF5, and MAP3K7/TAK1. Mutations were preferentially associated with the ABC-DLBCL phenotype, where 51.3% of the samples showed alteration in one or more gene, compared to 22.7% GCB-DLBCL. . . . Analysis of paired normal DNA, available from 8 samples, indicated the somatic origin of these events in at least one sample/gene" [In other words, the mutations were not inherited from a parent.] [Compagno, 2009]

Figure 3:
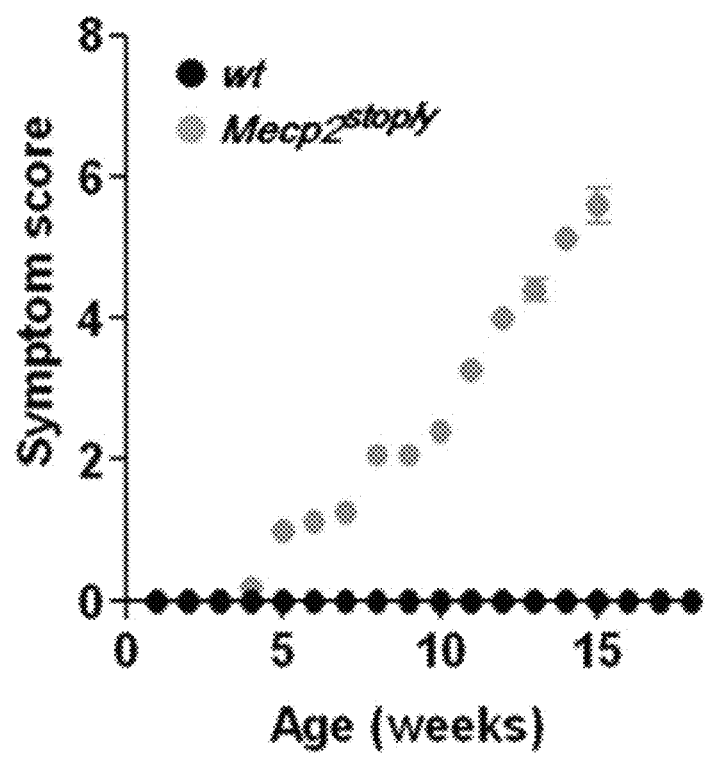
FIG. 3 (From Weng, 2011) shows how the RTT symptom score varies with age for MeCP2 null mice.

The gene expression profiles for these two types of PCNSL are incredibly different (see FIG. 3 of Visco, 2012).

An interesting set of experiments has shown that the simple treatment with a demethylating agent can eliminate developing tumors even before the cancer becomes apparent. In a rat model of esophageal carcinogenesis where NBMA (N-nitrosomethylbenzylamine) is used as the initiator and zinc-deficiency is used as the promotor, cancer typically develops in 15 weeks. But if the CpG demethylating agent DFMO (α-Difluromethylornithine, also known as Eflornithine) is administered in drinking water starting at week 5, the cancer is prevented. [Fong, 2001]

Immunohistochemical analysis shows that the DFMO treatment restored the expression of the p16 tumor suppressor gene, which had been silenced before the treatment and remained silenced in the control rats. Also, tissue samples from the DFMO treated rats show apoptosis of tumor cells and tumor shrinkage.

"The results from this study suggest that effective cancer prevention by DFMO under the present experimental condition entails: (a) prompt induction of apoptosis to remove damaged cells and, thus, reverse esophageal cell proliferation; and (b) sustained inhibition of cell proliferation to annul the continued effect of dietary zinc deficiency." [Fong, 2001]

6.13.7 Alternative Methods for Demethylating CpG Islands 6.13.7.1 5-aza-2'-deoxycytidine (5-azadC, Decitabine, Dacogen)

5-azadC treatment seems to be the most common method used for researchers for demethylating CpG islands in experiments. And it has been FDA approved as a drug (Decitabine, trade name Dacogen) for use in the treatment of myelodysplastic syndrome (MDS). It is a nucleoside analog for cytosine that is mutagenic because it can be incorporated in DNA. When incorporated in DNA, it is a suicidal inhibitor of DNA Methyltransferase enzymes (e.g DNMT1, DNMT3a, DNMT3b) because once they attach to the 5-azadC in the DNA, they become covalently bound and unavailable for any further DNMT activity. 5-azadC treatment has significant side effects.

6.13.7.2 Methotrexate

Methotrexate is an anti-folate drug that blocks the formation of S-Adenosyl methionine, the methyl donor that is necessary for DNMT activity. Without DNMT activity, CpG sites become demethylated. Methotrexate is one of the earliest developed chemotherapy drugs (1950) and is still extensively used. However, it has significant side effects and patients must be monitored (and dosage adjusted) in order to prevent complications from folate deficiency.

6.13.7.3 Histone Deacetylase Inhibitors Produce Demethylation

Although HDACi (or HAT histone acetyltransfer enzymes, or non-enzymatic histone acetylation) do not have direct demethylase activity, they interact with the MBD2 demethylase enzyme, allowing it to demethylate CpG sites more rapidly than the DNMT enzymes remethylate them. The result is eventual demethylation (e.g. within days, as in the RNA-mediated demethylation described in section 6.5.3.1 above).

"Valproic acid stimulates active demethylation of ectopically methylated . . . DNA." [Detich, 2003] For these experiments, cells were harvested 48 hours after treatment with valproic acid.

Figure 14:
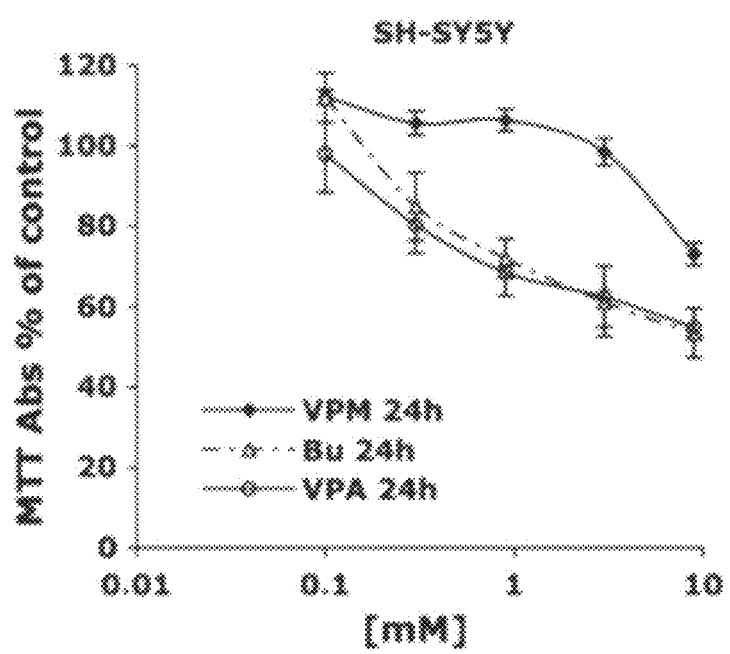
FIG. 14 (from condoreiii, 2008) shows cell viability after HDACi treatments.

The effect of valproic acid on restoration of p53 expression and subsequent apoptosis of neuroblastoma cells (after 24 hours) is shown in FIG. 14 (from Condorelli, 2008; VPA is valporic acid, VPM is a VPA analog, without HDACi activity, Bu is butyrate, MTT is an assay of cell viability). Note the similarity between the valproic acid and butyrate curves (nearly equal response to equal molarity treatment).

Without wanting to be bound to a particular theory, the applicant notes that it is not clear whether gene expression occurs when the histones become significantly acetylated (loosening the DNA and allowing its transcription) or waits until the CpG island has become demethylated (perhaps a day later). There are reports of HDACi induced gene expression without the CpG island being demethylated [Pruitt, 2006]. Perhaps a strong initial histone acetylation is sufficient for immediate gene expression and the CpG island demethylation (e.g. a day later) serves to re-enforce this. If so, increased histone acetylation may prove more effective than CpG island demethylation for the restoration of activity of tumor suppressor genes that were previously silenced.

The activity of TP53 as a transcription factor depends upon its ability to bind to DNA, which in turn depends upon the acetylation of lysines within the C-terminal 30 amino acids. Histone deacetylases (e.g. HDAC1, HDAC2, HDAC3, . . . ) reduce the activity of TP53, indicating that it is not sufficient to merely restore the expression of the p53 gene. HDACi treatment increases the acetylation of these lysines, restoring the activity of TP53 [Juan, 2000]. This argues that increased protein acetylation (e.g. from HDACi treatment) can be preferable to demethylation treatment for restoring TP53 function in tumor cells.

Various forms of mutated p53 which have lost their function as a transcription factor actually retain an ability to induce apoptosis through a transcription independent mechanism. The pro-apoptotic protein BAX is normally bound to the protein Ku70, but acetylated TP53 can cause the BAX to be released, allowing it to migrate to the mitochondria where it can induce apoptosis [Yamaguchi, 2009]. This additional method of action argues that increased protein acetylation (e.g. from HDACi treatment) can be preferable to demethylation treatment for restoring TP53 function in tumor cells, even for cells that have p53 mutations.

6.13.7.4 and Perhaps Dichloroacetate Produces CpG Demethylation

Michalakis reports that "the post-DCA treatment tumors from patients 2 to 4 showed increased activity of [ . . . TP53] (nuclear translocation), also confirmed by the increased activity and abundance of its downstream target p21. These effects on [TP53] or p21 can also explain . . . and are consistent with the antiproliferative, in addition to the proapoptotic, effects of DCA" [Michalakis, 2010].

This report leaves open whether the p53 gene became unsilenced by DCA treatment (consistent with the Warburg effect, as explained above in section 6.13.5) or existing TP53 protein is translocated to the nucleus. Given that almost all types of tumors have p53 expression inhibited (or p53 mutations, see section 6.13.6 above), it seems extremely unlikely that there was existing TP53 protein just waiting to enter the nucleus.

However, TP53 is known to require the acetylation of Lys-373 in order to bind to DNA, so perhaps they did actually observe increased translocation to the nucleus (due to increased TP53 acetylation). But if so, this implies that DCA has HDACi activity (which would explain its ability to reverse the Warburg effect, independent of the ability of DCA to inhibit the PDK enzyme). So the evidence seems to show that DCA treatment can lead to the activation of previously silenced genes and the demethylation of CpG islands.

Note: although (in the interest of brevity) this application has concentrated upon the tumor suppressor gene p53, there are other tumor suppressor genes, and other paths to apoptosis, that need to be silenced (or mutated, inhibited by a signaling pathway) for the badly DNA damaged tumor cell to avoid apoptosis. If any of these pathways is epigenetically silenced, but otherwise operational, the reversal of this silencing will result in the death of the tumor cell. Tumor suppressor genes which can invoke apoptosis include p53, p73, p21 and p16.

For example, the 13.8% of CNSL lymphoma patients who have p53 mutations (see above) probably still have a functional (but silenced or inhibited) p73, p21 or p16 gene.

6.13.8 What are the Metabolites of Dichloroacetate?

Using radiolabeled starting material, (producing radioactive DCA), it was determined that up to 50% of DCA is metabolized to carbon dioxide [Fitzsimmons, 2009] (exhaled in breath). The other major metabolites detectable in plasma and urine are Glyoxylate and Monochloroacetate (shown in bold in FIG. 15).

Figure 15:
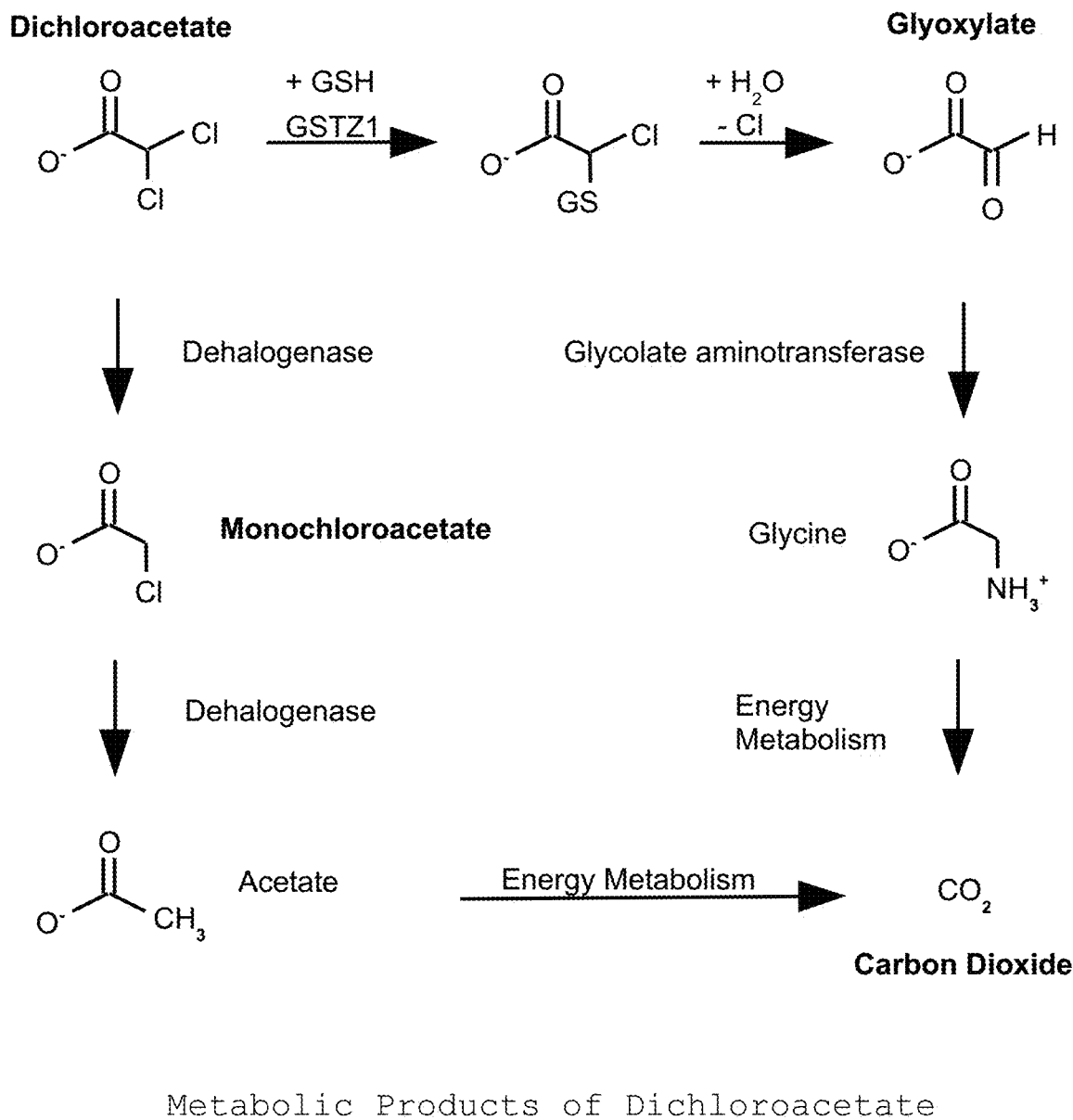
FIG. 15 Metabolic Products of Dichloroacetate.

As shown in FIG. 15, this is evidence for two major detoxification pathways, one based upon the zeta class glutathione transferase GST1Z (producing Glyoxylate), and the other based upon an unidentified dehalogenase (producing Monochloroacetate). The balance between these two pathways depends upon the activity of GST1Z, which varies with age and with genetic polymorphisms [Shroads, 2008].

Interestingly, one of the metabolites is acetate. It is not surprising that this acetate is readily metabolized (producing $CO_2$), given the efficiency of glycerine triacetate as a source of calories (see section 6.9 above).

6.13.8 DCA Toxicity

DCA inhibits the activity of the GST1Z enzyme, slowing the clearance of DCA and shifting the balance of its metabolic pathways towards the production of acetone, increasing the concentration of Monochloroacetate. Furthermore, the GST1Z enzyme is needed for other detoxification pathways, including the conversion of Maleylacetone to Fumarylacetone. The concentrations of both Maleylacetone and Monochloroacetate (from DCA administration) also rise with age. These molecules may be the cause of DCA induced peripheral neuropathy, the main toxicity of DCA.

DCA treatment also stimulates the activity of at least two enzymes that require thiamine as a cofactor. This can result in thiamine deficiency, which may be the cause of DCA induced peripheral neuropathy [Stacpoole, 1990]. This is why the Non-Hodgkins Lymphoma patient took thiamine along with his DCA (section 6.13.1 above).

6.13.9 Non-Hodgkin's Lymphoma Reversal with DCA Revisited

We know that for most patients with Non-Hodgkin's Lymphoma their p53 tumor suppressor gene is probably not mutated (see section 6.13.6 above), but is silenced. The genomic instability that is characteristic of cancer has assured that his tumor cells have multiple mutations, and would undergo apoptosis if their tumor suppressor genes hadn't been silenced. We also know that the reversal of this gene silencing (by the HDACi activity of the acetate from the DCA treatment) will allow these cells do what they should do (i.e. die via apoptosis). So the patient's miraculous cure (section 6.13.1) isn't a miracle after all.

6.13.10 Alternative "DCA-Like" Treatments for Cancer

The anti-cancer activity of DCA appears to be epigenetic in nature (see section 6.13.7.4 above). Given that one of the metabolites of DCA is acetate (a well-established HDACi, see section 6.6.2 above), it is clear that treatment with DCA will have an HDACi effect.

Other sources of acetate will also have this HDACi effect, and can avoid the toxicity of DCA (e.g. by not inhibiting GST1Z).

For treating cancer with a bioavailable source of acetate, it is just necessary to administer the appropriate amount of ProAcetyl compositions (capsules, food or beverages) to achieve the desired dosage amount.

Based upon the medicinal use of vinegar (for treating various ailments) and for the use of Dichloroacetate for treating cancer (section 6.13.1), the expectation is that 900 mg of acetate should produce a beneficial response. Of course, it would be appropriate to conduct a Phase I clinical trial to determine both the minimum effective dosage and the maximum tolerable dosage. Because of the very low toxicity of acetate (see below), it is expected that the "therapeutic window" will be very wide.

In the absence of a Phase I clinical trial, the most preferred dosage is 1500 mg of acetate per day. A less preferred dosage is 750 mg to 7500 mg of acetate per day. An even less preferred dosage is 375 mg to 15000 mg of acetate per day.

Because the practice in the art is to conduct a Phase I clinical trial to determine the acceptable dosage range for a pharmaceutical treatment, conducting such a clinical trial (or its equivalent) is not regarded within the art as undo experimentation.

6.14 Trinucleotide Repeat Disorders

6.14.1 Lovastatin Improves Behavior of Fragile X Patients

Treatment with lovastatin for 12 weeks improves the "Aberrant Behavior Checklist" score from ~50% to ~30% in adults and children with Fragile X syndrome (FXS, the most common inherited cause of mental disability) [Caku, 2014].

"In the majority of cases, FXS results from a [cytosine-guanine-guanine] (CGG) trinucleotide repeat expansion . . . associated with the methylation of its promoter. This epigenetic modification leads to transcriptional silencing of FMR1. Therefore, FXS is characterized by the absence or a reduced level of expression of the FMR1 protein, FMRP. . . . In general, the severity of cognitive dysfunction correlates with the magnitude of FMRP deficit: males being more profoundly affected than females." [Caku, 2014]

"In normal population this [CGG trinucleotide] repeat is composed of 5-55 repeats, allowing transcription and translation of the gene; within this size range the gene is transmitted stably over generations. When the repeat expands between 56 and 200 (premutation), the gene continues to transcribe (more) messenger RNA . . . Premutated alleles can expand to over 200 repeats (full mutation) when maternally transmitted, thus causing transcriptional repression of FMR1 through epigenetic modifications, namely: cytosine methylation of the expanded sequence and of the CpG island, deacetylation of histones 3 and 4, demethylation of lysine 4 on histone 3 (H3K4), methylation of lysine 9 on histone 3 (H3K9) and trimethylation of lysine 27 on histone 3 (H3K27) preventing transcription and resulting in the absence of FMRP protein." [Tabolacci, 2013]

This shows that the trinucleotide repeat ( . . . CGGCG-GCGGCGGCGGCGGCGG . . . ), which has a CpG in each of the repeating trinucleotides (shown in bold above), is acting like a classic CpG island, epigenetically. Indeed, DNA methyltransferases can recognize and methylate unusual DNA structures like trinucleotide CGG repeats in vitro [Sandberg, 1997].

Lovastatin treatment, by increasing the concentration of Acetyl-CoA (see section 3.3.2.2 above), is probably epigenetically unsilencing at least some of the FMR1 genes in these patients, allowing the production of more FMRP protein.

There is a rare class of FMR1 mutated carriers (with Unmethylated Full Mutations, "UFM") that are phenotypically normal males.

"The characterization of cell lines derived from these individuals has revealed that FMR1 promoter DNA is completely unmethylated (in both the CGG expansion and the FMR1 CpG island), transcription is increased (as in premutation carriers), FMRP levels are approximately 30-40% compared to normal (due to ribosome stalling on the expanded FMR1 mRNA). [Tabolacci, 2013]

This shows that if we can remove the ectopic methylation of the trinucleotide repeat, we can convert Fragile X patients to the UFM phenotype (i.e. cure the disease in that patient, without changing the underlying DNA mutation).

Figure 16:
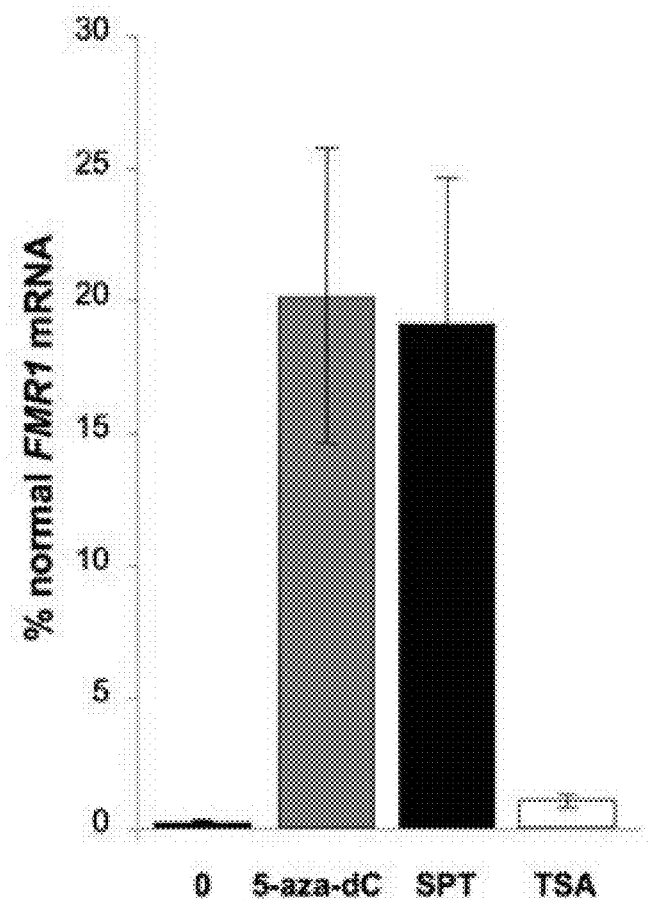
FIG. 16 (from Biacsi, 2008) shows gene reactivation from HDACi treatment.

Indeed, in Fragile X embryonic stem cells, where the repeat is still unmethylated, both FMR1 mRNA and FMRP are made [Baicsi, 2008]. Treatment with either the demethylating agent 5-aza-dC or with Splitomycin (SPT, a specific inhibitor Class III HDAC enzymes), but not Trichostatin A (a less specific HDACi) increased FMR1 mRNA to approximately 20% of normal control cells [FIG. 16 from Baicsi, 2008]. They note that treatment with 5-aza-dC is extremely toxic and requires DNA replication to be effective [Baicsi, 2008].

6.14.2 Other Trinucleotide Repeat Disorders

In Fragile XE mental retardation the repeated trinucleotide is CCG (instead of the CGG in Fragile X Syndrome), but his results in a CpG island just the same (with the CpG sights in bold below):

. . . CCGCCGCCGCCGCCGCCGCCGCCG . . .

In Friedreich ataxia, a fatal neuronal disease, the repeat sequence involves two trinucleotides (GAA and TTC) which also produces a CpG island:

. . . GAATTCGAATTCGAATTCGAATTCGAATTC-GAATTC . . .

Treatment with the HDACi SAHA (structurally similar to Trichostatin A) or Scriptaid increased FXN gene expression to >20% of normal control cells [Soragni, 2008].

Another large class of trinucleotide repeat diseases is the "Polyglutamine Diseases", where the repeating trinucleotide (CAG) codes for the amino acid glutamine. These diseases include Huntington's Disease (HD), Dentatorubropallidoluysian atrophy (DRPLA), Spinal and Bulbar Muscle Atrophy (SBMA), and Spinocerebellar ataxia Types 1, 2, 3, 6, 7, and 17 (ATXN1, ATXN2, ATXN3, CACNA1A, ATXN7, and TBP). For all of these diseases, the repeat sequence is within the androgen receptor (AR) gene itself:

. . . CAGCAGCAGCAGCAGCAGCAG . . .

In this case, the toxicity of the repeat sequence is not due to CpG sites in the DNA. It turns out that the transcription of this sequence produces polyglutamine, which forms inclusions which bind to the "CBP" Histone Acetyl Transferase (HAT) proteins and sequesters them. This caused a general hypoacetylation of histone H3, as has been observed in Huntington's Disease. "If sequestration of CBP and other histone acetylases leads to cell death by decreasing histone acetylation, then addition of deacetylase inhibitors would be expected to reduce cell loss. We tested the ability of various deacetylase inhibiters to reduce polyglutamine induced cell death" [McCampbell, 2001].

"In our assay, SAHA [a drug similar to Trichostatin A, TSA] was comparable to TSA in its ability to reduce cell death . . . We tested two other deacetylase inhibitors, sodium butyrate and PBA [phenylbutyric acid]. These compounds, while inducing histone acetylation, have broader effects on gene expression than TSA. Mariadason et al. [Mariadason, 2000] showed that sodium butyrate modifies roughly 10 times as many genes as TSA in cultured colon cells . . . . The reduction in cell death caused by these compounds is not attributable to a decrease in AR [the mutant protein] expression levels. Indeed, the expression of [the mutant protein] is slightly increased by the presence of SAHA, TSA, sodium butyrate, and PBA." [McCampbell, 2001]

"In 2003, there was a report that SAHA added to drinking water of R6/2 HD mice, the mouse model for this disease, resulted in a marked improvement in motor function. Transgenetic mice expression human Huntington with an expanded CAG/polyglutamine repeat develop a regressive syndrome with many of the characteristics of human Huntington disease. Indeed, SHA crosses the blood-brain barrier and increases histone acetylation in the brain. The administration of SAHA has consistently shown this therapeutic benefit in the mouse model; nevertheless, which HDAC is affected by SAHA to improve motor function in the R6/2 mouse model remains unclear.

6.15 What Makes Acetate Especially Efficient as an HDACi?

While now wanting to be bound by any particular theory, the applicant notes that in *E. coli*, the enzyme Acetate Kinase (AckA) converts acetate to Acetyl-phosphate (AcP), and the Acetyl-phosphate non-enzymatically acetylates a significant percentage of the lysine residues of the proteins in the cell. This occurs when the cell is in a nutrient-poor environment, switching the bacteria from its "exponential growth phase" (EP) to its "stationary phase" (SP). [Weinert, 2013]

> ". . . we compared acetylation between lysine acetylation in actively growing, exponential phase (EP) cells to acetylation in stationary phase (SP). Surprisingly, acetylation was dramatically and globally increased in SP cells. . . . Increased acetylation was nearly comprehensive (94% of sites were more than 2-fold elevated), and most sites were more than an order of magnitude increased in acetylation (median 11.7-fold). The large median increase indicates that more than half of the sites were less than 8.5% acetylated in EP cells." [Weinert, 2013]
>
> "In this work we identified more than 8,000 unique acetylation sites in *E. coli* and showed that most acetylation occurs at a low level and is affected by AcP concentration in a uniform manner. . . . This data established AcP as a critical regulator of acetylation in bacteria and suggest that AcP acts non-enzymatically to regulate acetylation levels. . . We found that [cells without the AckA enzyme] had a median ~14-fold higher level of acetylation than [cells that lack the enzyme that converts Acetyl-phosphate to Acetyl-CoA, decreasing the AcP level] at thousands of sites." [Weinert, 2013]

The existence of a non-enzymatic process for histone acetylation may explain why there is such a diversity of histone deacetylases (with a diversity of functions) and only a few, relatively nonspecific histone acetyl transferase enzymes. If histone acetylation is occurring non-enzymatically (hence, relatively uncontrolled) having the deacetylase enzymes (which can be part of specific signaling pathways) determine the acetylation/non-acetylation balance of specific sites would seem to be necessary.

If humans have an analogous pathway from acetate to Acetyl-phosphate, this would explain the ability of acetate from dichloroacetate to be more effective at inducing the re-expression of formally silenced tumor suppressor genes than the other HDACi (and demethylases) that have been tested as antitumor agents.

6.16 Revisiting the Warburg Effect (Again)

Without wanting to be bound by a particular theory, the applicant notes that the cellular switch between an "exponential growth phase" (EP) and a "stationary phase" (SP) is called the "Acetate Switch" [Wolfe, 2005]. The ability of cell to switch between these two modes, and its dependence upon the extracellular acetate concentration, developed first in eubacterial species (prokaryotes) and has been retained through evolution, including human cells [Wolfe, 2005].

The "exponential growth phase" is associated with a decrease in protein acetylation, including decreased histone acetylation. This serves as a global signaling mechanism within the cell for these proteins to be in "reproduction" mode. (The converse, increased acetylation in the stationary phase, signals to these proteins that they should be in non-growth mode.)

The Warburg Effect involves a cellular metabolic shift to glycolysis, which prevents pyruvate from entering the Krebs cycle, allowing ATP to be formed without producing Acetyl-CoA at the same time. This helps maintain the low level of acetylation that has been the signal for exponential reproduction, long before tumor suppressor genes (or apoptosis, or even mitochondria) ever existed. It seems that the main reason for the Warburg Effect is to prevent the formation of Acetyl-CoA, starving the cell of acetyl groups, and putting the tumor cell into exponential growth mode. And because this mode is controlled by the "acetate switch", extracellular acetate (which specifically controls the switch) can switch the tumor out of exponential growth mode.

In summary, acetate is a very efficient source of acetyl groups for enzymatic and non-enzymatic protein acetylation, including histone acetylation. Dietary sources of acetate can be used to treat a variety of genetic and epigenetic diseases and disorders. The low toxicity of dietary sources of acetate such as the FDA approved food additives calcium acetate, sodium acetate and potassium acetate provides a wide therapeutic window for treatments. Not that these are all simple, ionically bound salts that disassociate in water, yielding only acetate and the non-toxic ions of sodium, calcium and potassium. Similarly, the dietary supplement magnesium acetate yields only acetate and magnesium.

It is especially interesting that DCA preferentially kills cancer stem cells. There is an ongoing problem of disease recurrence after "successful" chemotherapy. Perhaps every patient, after completing chemotherapy or radiation, should also receive ProAcetyl treatment to clear out any cancer stem cells that survived the chemotherapy. This is a low toxicity treatment that can easily be added to conventional anti-cancer treatments. And the ability to clear cancer stem cells from the body could be used periodically (e.g. every year or to) in order to prevent cancers from developing.

What is claimed is:

1. A method for treating a cancer that has decreased tumor suppressor gene expression in a subject in need thereof, the method comprising administering to the subject about 375 mg to about 15,000 mg of acetate per day, wherein said acetate is provided as a composition comprising magnesium acetate, calcium acetate, or ethylacetate; and wherein administration of said composition increases expression of a tumor suppressor gene in cancerous cells.

2. The method of claim 1, wherein the amount of acetate per day is about 750 mg to about 7500 mg.

3. The method of claim 1, wherein the amount of acetate per day is about 750 mg to about 3000 mg.

4. The method of claim 1, wherein the amount of acetate per day is about 375 mg to about 2000 mg.

5. The method of claim 1, wherein said composition is a nutraceutical.

6. The method of claim 1, wherein said composition is a dietary supplement.

7. The method of claim 6, wherein said dietary supplement is in the form of a capsule.

8. The method of claim 1, wherein administration of said composition inhibits proliferation of cancer cells of said subject.

9. The method of claim 8, wherein said cancer cells are cancer stem cells.

10. The method of claim 1, wherein administration of said composition inhibits tumor growth or reduces a tumor's size.

11. The method of claim 1, wherein administration of said composition increases histone acetylation of tumor suppressor genes in cancerous cells in said subject.

12. The method of claim 1, wherein administration of said composition decreases methylation at CpG islands of tumor suppressor genes in cancerous cells in said subject.

13. The method of claim 1 where said tumor suppressor gene controls apoptosis.

14. The method of claim 13 where said tumor suppressor gene is the gene for p53, p73, p21 or p16.

15. The method of claim 14 where said tumor suppressor gene is the gene for p53.

16. The method of claim 15 where said gene for p53 is not mutated.

17. The method of claim 1 where said tumor suppressor gene is a DNA repair gene.

18. The method of claim 17 where said tumor suppressor gene is the gene for BRCA1, MLH1 or MGMT.

19. A method for treating a skin cancer that has decreased tumor suppressor gene expression in a subject in need thereof, the method comprising topically administrating a composition comprising ethylacetate; and wherein administration of said composition increases expression of a tumor suppressor gene in cancerous cells.

20. The method of claim 19 where said tumor suppressor gene controls apoptosis.

21. The method of claim 19 where said tumor suppressor gene is the gene for p53, p73, p21 or p16.

22. The method of claim 21 where said tumor suppressor gene is the gene for p53.

23. The method of claim 22 where said gene for p53 is not mutated.

24. The method of claim 19 where said tumor suppressor gene is a DNA repair gene.

25. The method of claim 24 where said tumor suppressor gene is the gene for BRCA1, MLH1 or MGMT.

* * * * *